United States Patent [19]

Cambier et al.

[11] Patent Number: 5,159,361
[45] Date of Patent: Oct. 27, 1992

[54] METHOD AND APPARATUS FOR OBTAINING THE TOPOGRAPHY OF AN OBJECT

[75] Inventors: James L. Cambier, Rome; Salvins J. Strods, Waterville, both of N.Y.

[73] Assignee: Par Technology Corporation, New Hartford, N.Y.

[21] Appl. No.: 562,481

[22] Filed: Aug. 3, 1990

Related U.S. Application Data

[63] Continuation-in-part of Ser. No. 321,252, Mar. 9, 1989, Pat. No. 4,995,716.

[51] Int. Cl.$^5$ ............................................. A61B 3/10
[52] U.S. Cl. .................................... 351/212; 351/247
[58] Field of Search ................ 351/212, 247; 356/395, 356/396

[56] References Cited

PUBLICATIONS

Joseph W. Warnicki, Paul G. Rehkopf, Diane Y. Curtin, Stephen A. Burns, Robert C. Arffa and John C. Stuart, "Corneal Topography Using Computer Analyzed Rasterstereographic Images," in *Applied Optics*, vol. 27, No. 6 (Mar. 15, 1988), pp. 1135–1140.

Thomas Olsen, "On the Calculation of Power from Curvature of the Cornea," *British Journal of Ophthalmology* (Feb. 1986), vol. 70, pp. 152–154.

Carsten Edmund and Erik Sjontoft, "The Central-Peripheral Radius of the Normal Corneal Curvature," *ACTA Ophthalmologica*, (Dec. 1985), vol. 63, pp. 670–677.

Joseph W. Warnicki and Paul G. Rehkopf, "Development of an Imaging System for Ophthalmic Photography," *Journal of Biological Photography*, vol. 53, No. 1 (Jan. 1985), pp. 9–18.

Stephen P. Klyce, "Computer-Assisted Corneal Topography," *Investigative Opthalmology and Visual Science*, vol. 25 (Dec. 1984), pp. 1426–1435.

Marco S. Caceci and William P. Cacheris, "Fitting Curves to Data," *Byte* (May, 1984) pp. 340–357.

J. James Rowsey, M.D.; A. E. Reynolds, Ph.D.; Randy Brown, "Corneal Topography," *Arch Ophthalmol*, vol. 99 (Jun. 1981), pp. 1093–1100.

M. S. Moreland, M.D.; C. A. Barce, B.A.; M. H. Pope, Ph.D.; "Moire Topography in Scoliosis: Pattern Recognition and Analysis," *Moire Fringe Topography and Spinal Deformity*, Pergamon Press, (1981), pp. 171–185.

(List continued on next page.)

*Primary Examiner*—Rodney B. Bovernick
*Attorney, Agent, or Firm*—Arnold B. Silverman; Suzanne Kikel

[57] ABSTRACT

A system, method, and apparatus for obtaining the corneal topography of an object using computer analyzed rasterstereographic images. The object may be non-transparent and diffusing, or it may be transparent and nondiffusing, such as a cornea. Rasterstereographic images of a cornea are produced by staining the cornea with a fluorescein solution which projects a light and dark line pattern onto the cornea through a grid. When obtaining the topography of a cornea, several different filters are used for producing and obtaining a grid image. An image processor uses unique software to store and analyze data extracted from the grid pattern. A video camera, an illuminator, the filters, and the grid may be mounted on a microscope. One embodiment uses a grid with vertical lines. Another embodiment uses a grid having intersecting horizontal and vertical lines for exhibiting surface details in a two-dimensional x-y plane. A computerized method and associated apparatus uses the data from the x-y plane to determine the projected grid intersection points (PGI) on the surface of the cornea by intersecting a light ray formed by the grid intersection (GI) points on the actual grid in the projected system with a light ray formed by the grid intersection (IPGI) points of the image in the camera system.

50 Claims, 27 Drawing Sheets

PUBLICATIONS

Marius C. VanWiik, "Accuracy of Moire Topography," *Moire Fringe Topography and Spinal Deformity*, Pergamon Press (1981), pp. 47–57.

J. D. Doss et al., "Method for Calculation of Corneal Profile and Power Distribution," *Arch Ophthalmol.*, 1261 (Jul. 1981).

T. Yatagai, M. Idesawa, H. Ohshima, and M. Suzuki; "Automatic Measurement of 3-D Shapes Using Scanning Moire Method," *Moire Fringe Topography and Spinal Deformity*, Pergamon Press (1981), pp. 249–257.

E. Hierholzer and W. Frobin, "Rasterstereographic Measurement and Curvature Analysis of the Body Surface of Patients with Spinal Deformities;" *Moire Fringe Topography and Spinal Deformity*, Pergamon Press (1981), pp. 267–276.

N. Ikeda, "Perspective Correction of the Moire Photograph," *Journal of the Biological Photographic Association*, vol. 47, No. 3 (Jul., 1979), pp. 107–110.

M. S. Karlan, M.D.; M. Madden, M.A.; and M. B. Habal, M.D.; "Biostereometric Analysis in Plastic and Reconstructive Surgery," *Plastic and Reconstructive Surgery*, vol. 62, No. 2 (Aug., 1978), pp. 235–239.

T. W. Smith, M.D., "Corneal Topography," *Documenta Opthalmologica* 43.2 (Jun. 1977), pp. 249–276.

S. Wittenberg and Wm. M. Ludlam, "Planar Reflected Imagery in Photokeratoscopy," *Journal of the Optical Society of America*, vol. 60, No. 7 (Jul., 1970), pp. 981–985.

H. Takasaki, "Moire Topography," *Applied Optics*, vol. 9, No. 6, (Jun., 1970), pp. 1467–1472.

Wm. M. Ludlam and S. Wittenberg, "Measurements of the Ocular Dioptric Elements Utilizing Photographic Methods," *American Journal of Optometry Publishing Association*, (Apr., 1966), pp. 249–267.

S. Wittenberg and Wm. W. Ludlam, "Derivation of a System for Analyzing the Corneal Surface from Photokeratoscopic Data," *Journal of the Optical Society of America*, vol. 56, No. 11, (Nov., 1966) pp. 1612–1615.

R. C. Arffa, M.D., J. W. Warnicki, B.A., and Paul G. Rehkopf, B.S "Corneal Topography Using Rasterstereography," *Refractive and Corneal Surgery*, vol. 5, Nov./Dec. 1989, pp. 414–417.

PRIOR ART  PRIOR ART

Contrast Algorithm
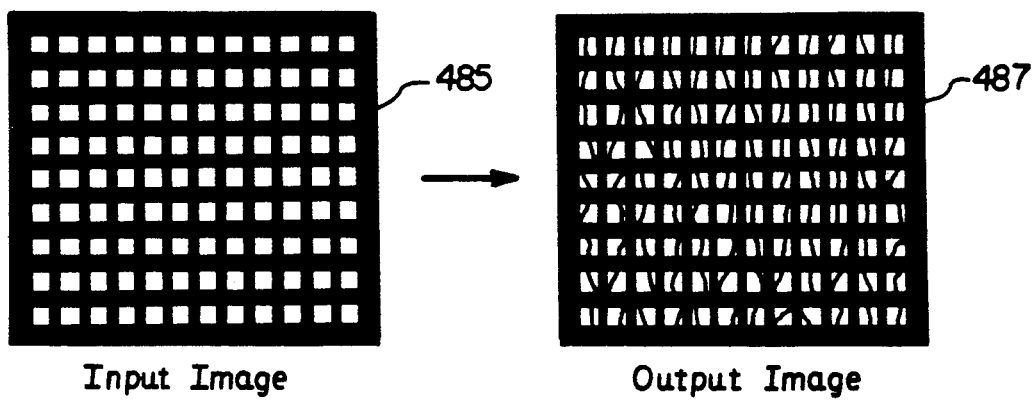
Input Image → Output Image
FIG. 26A
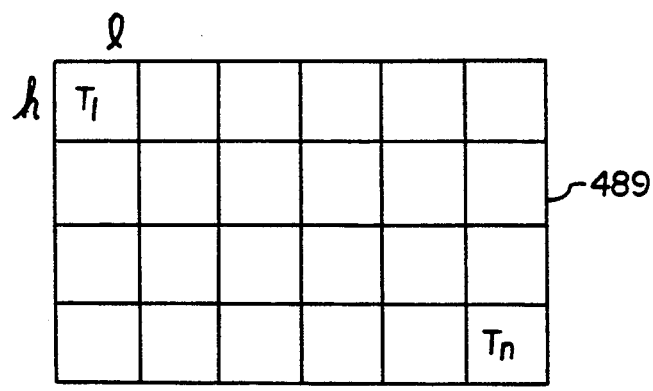
FIG. 26B
T = 75
Row 1   50  40  45  100  107  110  106  99  43  42  56
Row 2   D   D   D   B    B    B    B    B   D   D   D
Row 3   •   •   •   •    •    X    •    •   •   •   •
FIG. 26C Traceline Algorithm Find REFPT Algorithm

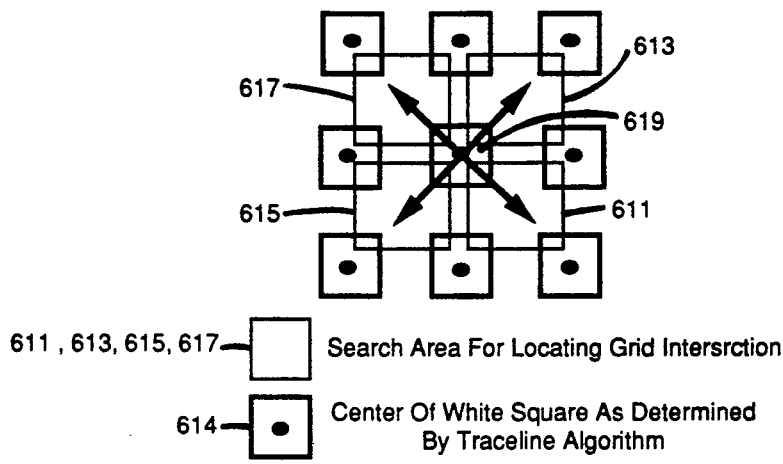
FIG. 32A
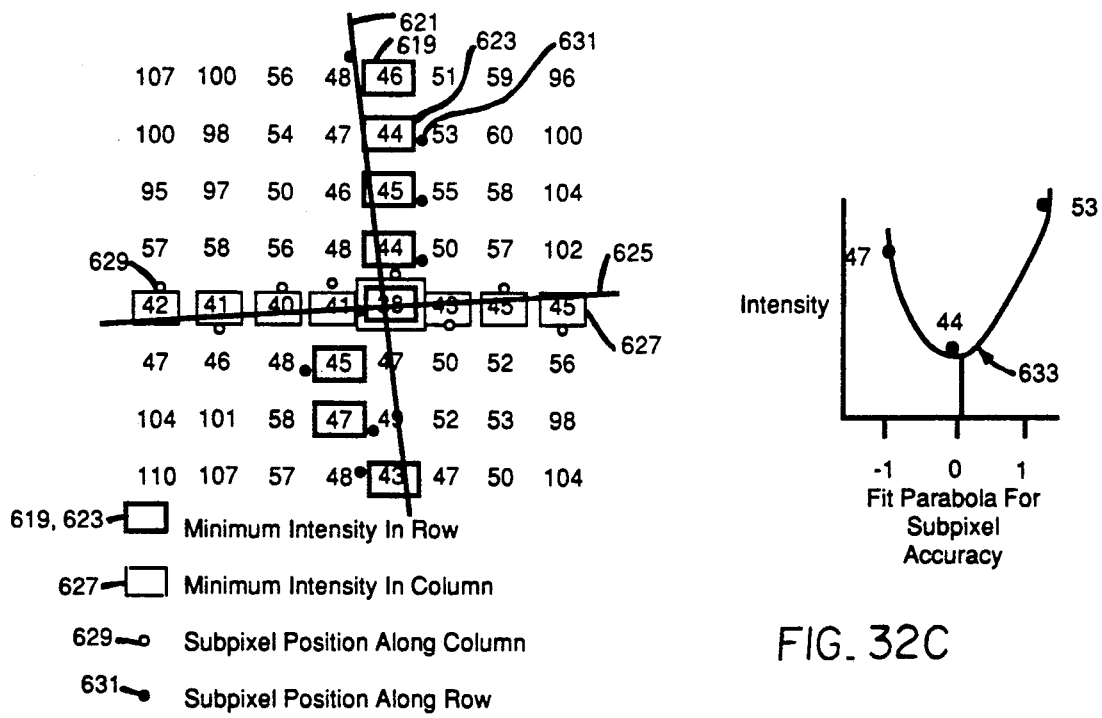
FIG. 32B
FIG. 32C

MAKESQ Algorithm

Division Of Input Grid Into Triangles

Determining If Point Is Inside Triangle

ABC Triangle Of Irregularly Spaced Input Points
D - Point On Evenly Spaced Output Grid
E - Intersection Of AD And BC D Is Inside △ ABC If
    1) D Is Between A And E Along $\overline{AD}$ And,
    2) E Is Between B And C Along $\overline{BC}$

METHOD AND APPARATUS FOR OBTAINING THE TOPOGRAPHY OF AN OBJECT

This is a continuation-in part application of application Ser. No. 07/321,252 filed on Mar. 9, 1989, now U.S. Pat. No. 4,995,716.

BACKGROUND OF THE INVENTION

1. Field of the Invention

This present invention relates to a system, method, and associated apparatus for enabling the use of rasterstereographical principles for determining the curvature and surface detail across the surface of an object by using a computer analyzed rasterstereographic technique. More specifically, a projected light and dark pattern on the object is picked up by a video camera and the image is digitized by an image processor which calculates the surface detail by evaluating the distortion of the grid lines.

2. Description of the Prior Art

In recent years there has been increased interest in both qualitative and quantitative measurements of an object by topography. Particularly this increased interest has been in regard to corneal topography especially relating to keratorefractive procedures. Since keratorefractive procedures correct the refractive error of the eye by altering the curvature of the corneal surface, topographic measurements of the corneal curvature are important in planning, performing, and assessing the effect of these procedures.

Corneal topography has been proven of value for numerous uses including predicting the result of radial keratotomy, evaluating the design of epikeratophakia for myopia, diagnosis and staging of keratoconus, and guiding suture removal after corneal transplantation.

There have been previously reported photographic methods based on the keratoscopic disk system. (See "Corneal Topography," J. J. Rowsey, et al., Arch. Ophthalmol., Vol. 99, 1093 [1981]). This keratoscopic system consists of a series of black and white concentric rings on a circular disk. When this disk is placed in front of the eye, the rings are reflected by the corneal surface and their position, size, and spacing in the reflected image are determined by the corneal shape.

Current commercial systems utilizing illuminated concentric circular rings surrounding a viewing port through which photographs are taken have been known. If the cornea is spherical, the rings appear round and regularly spaced. If the cornea is oval or astigmatic, the rings are oval and the spacing varies in different axes. This is known as the placido disk technique.

These techniques, while providing a visual representation of the corneal surface, do not provide quantitative information. Computer programs have been developed which calculate the corneal profile and the optical power distribution on the corneal surface from placido disk images. See "Method for Calculation of Corneal Profile and Power Distribution," J. D. Ross, et al., Arch Ophthalmol., 1261 (1981).

Computer analyzing techniques have been developed for deriving quantitative information about the corneal shape from keratoscope photographs and displaying the results both numerically and graphically in easily understood forms. See "Computer-Assisted Corneal Topography, High Resolution Graphic Presentation and Analysis of Keratoscopy," S. D. Klyce, et al., Investigative Ophthalmology and Visual Science, Vol. 25, 1426 (1984).

Placido disk techniques for recording and quantifying the corneal surface have inherent limitations which reduce their clinical usefulness.

There are three main factors which limit the usefulness of the placido disk system. These factors are as follows: 1) The most central portion of the cornea is not imaged. This is due in part to the fact that there is a hole in the central portion of the placido disk through which the optical system for this technique views the cornea. This viewing port is devoid of any lighted spots or rings, and therefore there can be no reflected images on the cornea in this area. 2) The diameter of the placido disk determines how much of the corneal surface is covered by the reflected images. The smaller the diameter, the smaller the area of the cornea. The larger the diameter, the larger the area of the cornea that will be covered extending more toward the limbus or periphery of the cornea. 3) The distance between the cornea and the placido disk system also determines how much of the cornea is covered. The farther away the disk is from the cornea, the less the corneal coverage will be. The closer the disk is to the cornea, the greater the corneal coverage will be.

Other limitations of the placido disk techniques are that they do not extend to the corneal limbus due in part to shadows being cast from the eye lashes, brow, and nose of the patient, nor do they work on corneas which do not have the necessary qualities to reflect an image of the disk due to conditions such as epithelial defects, scarring, or highly irregular shape.

Current computer methods being used to obtain quantitative measurements have been known to utilize photo graphic images acquired with the commercially available placido disk keratoscopes and are, therefore, subject to the same limitations discussed hereinbefore. In some such systems the data are entered into the computer by hand digitizing from these photographs, requiring a considerable amount of time, and the possible introduction of error during the digitization process.

While hand digitizing with some manually manipulated device is still being practiced, there is also known at least two systems for direct digitizing purposes, which systems have imaging cameras attached to the optics which, in turn, view through the central portion of the placido disk. These images are then taken directly into the computer for manipulation in calculating the corneal curvature and for determining the diopter powers.

These systems with direct digitization are still subject to the same problems as the placido disk systems having hand digitization. Although several attempts have been made to extend farther out into the limbus or periphery of the cornea, none of these systems have achieved this capability. These systems still inadequately handle corneas with very steep curvature or with a highly irregular surface.

It has been known to employ a rasterstereography method for measuring large body surfaces, curvature of the back, and reconstructive plastic surgery. Rasterstereography is an intermediate between stereography and moire topography, and is a method of obtaining contour or topographic information where one of the cameras in a stereogrammetric pair is replaced with a light source which projects a grid of vertical parallel lines onto a subject.

One type of rasterstereographic system employs an electronic camera with a linear sensor, an x-y translator for image shifting, and a light source or projector. The camera and translator are connected to an on-line computer which produces an image scan of the large surface. See "Rasterstereographic Measurement and Curvature Analysis of the Body Surface," E. Hierholzer, et al., Biol. Photogr., Vol. 51, 11 (Jan. 1, 1983).

It has been known to employ a Rhonchi ruling in moire technique, which is normally a technique used for measuring the topography of a solid, nontransparent object. In moire topography a light source illuminates the Rhonchi ruling to cast shadows on the object to be measured. These shadows and the lines of Rhonchi ruling when viewed by either the eye or a camera interfere to produce contour lines of the object. See "Biostereometric Analysis in Plastic and Reconstructive Surgery," M. S. Karlan, et al., Plastic and Reconstructive Surgery, Vol. 62, (1978).

It has been known to attempt to determine corneal topography including moire techniques. A drawback is the low reflectivity of the cornea in that the cornea is a transparent, nondiffusing member, which does not allow for a good image of the grid to be formed on it.

It has been known to employ a microscope with a reticule referred to as a toposcope which uses the moire technique. A reticule is a grid or scale that is a standard piece of equipment in the moire technique. A series of straight parallel lines is imaged on the object. In the eyepiece of the microscope there is a reticule with the same number of lines. The two patterns interfere to produce the contours. This instrument has been used to analyze contact lenses, but there is no evidence of using it to determine the contour of an eye. A drawback would be the low reflectivity of the cornea.

It has been known to use a fluorescein solution on the eye, and a contact lens to determine the topography of a cornea. The fluorescein solution is placed on the eye, followed by the placement of a contact lens. Blue-violet radiation produces a fluorescence pattern which gives an indication of the variable clearance between the known surface of the contact lens and the unknown cornea. For the measurements to be valid, the lens must be kept stationary, and, in practice, diagnostic contact lenses are used to verify 'K' readings in conjunction with refractive findings. See "Corneal Topography," T. W. Smith, M.D., Documenta Opthalmologica 43.2, pg. 262 (1977).

It has been known to determine corneal topography by stereographic techniques, in addition to holographic interferometric, and profile techniques. See "Corneal Topography," pg. 263 cited in the preceding paragraph.

As the cornea is a transparent member which is nondiffusing to light, a grid projected onto the cornea is not visible unless a diffusing material is used to provide a surface on which an image can be visualized. It has been known to spray talcum powder on anesthetized corneas to obtain stereo photographs of the cornea.

Stereophotography is traditionally used to obtain the topography of a solid, nontransparent light diffusing object that has some texture. Stereophotography may utilize two cameras which view an object of interest from two different angles relative to a fixed center line between them. Stereophotography can also be accomplished by taking two sequential images with one camera. This is accomplished by focusing the camera on a fixed point and taking an exposure. The camera is then moved laterally a fixed distance, again focusing on the same point previously used in the first image and another exposure is made.

The two stereo photos are analyzed and one of the images is chosen as a reference image. Some object of interest is chosen and the displacement of the object in the opposite stereo image can be measured. From this displacement and the angle between the two shots, an elevation of an object can be calculated.

As the stereophotography method is used on solid objects, it has not been known to adequately obtain the topography of a cornea in that sufficient topographic detail of the cornea cannot be extracted.

It has been known to use an image processing system with a video camera, flash unit, and computer and display units in the field of opthalmology where the eye images are handled electronically. However, most of the study in the ophthalmology field has been in evaluating the optic nerve, retina, and corneal surface defects, and not for determining the curvature and related topographic details of the cornea. See "Development of An Imaging System for Ophthalmic Photography," J. W. Warnicki, et al., J. Biol. Photog. 53, 9 (1985).

In the holographic interferometric technique, it is known to use a beam splitter to direct the laser beam in one direction toward a camera and in the other direction toward an object. See "Corneal Topography," pg. 264 cited hereinbefore.

In spite of these known systems, methods, and instruments, there remains a very real and substantial need for a system, method, and device which more accurately and quickly determine quantitatively and qualitatively the contour of both a light diffusing, nontransparent object and a light nondiffusing, transparent object, such as a cornea.

SUMMARY OF THE INVENTION

The present invention has met the above-described needs. A system, a method, and an apparatus of the present invention provide more accurate and easily obtainable means for determining the topography of an object, particularly that of a cornea as defined hereinafter.

The apparatus may provide a support means with built-in optical means and a beam splitter along a centerline of the support means. The apparatus and associated method may involve providing an illuminator/flash unit, a grid, a cobalt blue filter, and an infrared cutoff filter on one side of the support means, and a video camera, and a yellow barrier filter on the other side of the support means.

If the topography of a cornea is to be obtained, fluorescein solution is applied onto the tear film of the cornea so that the grid pattern created through the grid of a Rhonchi ruling becomes fluorescent when excited by light passing through the cobalt blue filter. The yellow barrier filter is employed to increase the contrast of the grid image by the video camera. When the topography of an object, other than that of a cornea is to be determined, the filters preferably are not used. The recorded image of the object is used to identify the central area of the lines of the grid pattern, to calculate the elevation of the lines of the grid pattern, and to display the elevational results in a contour plot representative of the topography of the object.

The apparatus preferably comprises a microscope with two beam splitters, a video camera, and optics along a centerline in line with a support for resting and placement of an object, which in the instance of the cornea is the head of a patient. A video camera and the yellow barrier filter are located at an angle relative to and along the centerline of the apparatus, and an illuminating source, a grid, and the cobalt blue and infrared cutoff filters are located in a line relative to each other and at an angle relative to the centerline opposite to that of the video camera. An image processor is employed to determine the topography of the object through the use of software which identifies, and calculates the elevation of the grid lines, and displays the results in a contour plot representing the topography of the object.

The system, method, and apparatus may be used for obtaining the topography of an object which is transparent and nondiffusing to light, such as a cornea, or which is nontransparent and diffusing to light.

It is a broad object of the invention to provide a system, an apparatus, and a method for quickly and efficiently determining the topography of an entire surface of an object, which object is transparent and nondiffusing to light, such as a cornea, or which is nontransparent and diffusing to light.

It is a further object of the present invention to provide a system, an apparatus, and a method for quickly and efficiently determining the topography of an entire cornea of a patient, which is a member of the animal kingdom, particularly a human.

It is a further object of the present invention to provide a system, a method, and an apparatus for achieving the preceding objective by obtaining information on curvature and surface detail across the full cornea surface including the central optical axis and the periphery beyond the limbus.

It is a further object of the invention to provide a system, a method, and an apparatus for effectively projecting a grid onto the object and shortening the computer time by digitizing a video image of the grid by an image processor which calculates surface detail by evaluating the distortion of the grid lines.

It is another object of the invention to provide such a system which attaches to an examination slit lamp microscope and which is compact, economical, providing valid clinical information regarding curvature and topography, particularly of a cornea, and which is easily operated by medical personnel.

It is yet another object of the invention to provide such a system which attaches to a microscope which is used in an operating room.

It is a further object of the invention to provide a system, an apparatus, and a method for quickly and efficiently determining the topography of an entire surface of an object and reproducing the results, and which system and apparatus are easy to operate, are inexpensive to buy and operate, and which system, apparatus and method are harmless to the object, especially a cornea, and are generally not unpleasant for the patient.

It is a further object of the invention to provide a system, a method and an apparatus for obtaining the topography of a cornea which enables a grid image to be reflected from the cornea.

It is a further object of the invention to provide a system, an apparatus, and a method whereby digital imaging processing techniques are used to find elevation information, from which, in turn, curvature information is extracted.

It is a further object of the invention to provide a system, an apparatus, and a method relative to the preceding objective whereby from the extracted data, an assessment of the shape of the object and the refractive power of the front surface of a cornea can be made.

A further object of the invention is to provide such a system which is compact, economical, and together with computer hardware and appropriate software is capable of making calculations in an operating room where time is of the essence.

It is therefore an object of the present invention to more effectively and efficiently obtain the topography of an object, such as a cornea, and to achieve this through a rasterstereographic technique.

It is a further object of the invention to project a grid image onto a transparent, nondiffusing object, such as a cornea rather than have the grid image reflected by the cornea, so that the projected image is not affected by surface defects and irregularities.

It is a further object of the invention to electronically acquire the image of an object, electronically digitize and analyze the imaging system, and display the data obtained from the analysis of these images in easily understood formats.

It is a further object of the invention to apply a digital image processing technique to the projected image in order to find the projected lines and to convert the lines into elevation information.

It is a further object of the invention to extract curvature information and in the instance where the cornea is being examined, diopter powers from the curvature information.

It is a still further object of the invention to use the elevation and curvature information to obtain an intuitive and quantitative assessment of the shape and refractive power of the front surface of the cornea.

A further object is to utilize computer processing techniques including a main program with a number of subroutines including an edge determining subroutine, a line segment constructing subroutine, a matrix building subroutine, an elevation computing subroutine, and a curvature computing subroutine.

It is a further object of the invention to adapt a Zeiss or a Topcon exam slit lamp microscope, which may generally have been used in stereophotographic techniques for obtaining the topography of a cornea, to a rasterstereographic method for obtaining the topography of a cornea.

A still further object of the invention is to adapt a Zeiss or a Topcon exam slit lamp microscope to a raster stereographic method for obtaining the topography of any object.

It is a further object of the invention to provide in a rasterstereographic technique a cornea surface with a grid image projected thereon.

It is a further object to achieve the immediately preceding objective by applying a fluorescein solution onto the surface of the eye.

It is a further object of the invention to provide a grid whose projected pattern will provide an output having two-dimensions.

It is further object of the invention to provide a grid with intersecting horizontal and vertical lines resulting in exhibiting details on the cornea in two dimensions in order for the distorted positions of the lines to be detected in a two dimensional x-y plane.

It is further object of the invention to provide a computerized method and an apparatus thereof for determining the location of both the grid intersection (GI) points of the projection grid and the imaged projection grid intersection (IPGI) points in the image, mathematically constructing from the data obtained for the determination of the location of the GI and IPGI points, a first and second light ray respectively, and determining the location of the projected grid intersection (PGI) points on the surface of the cornea by intersecting the first light ray for the GI points with the second light ray for the IPGI points.

A still further object is to provide a computerized method and an associated apparatus which from the data obtained in determining the position of the PGI points of the previous object to determine the topography of the cornea.

These and other objects of this invention will be more fully understood from the following description of the invention on reference to the illustrations appended hereto.

BRIEF DESCRIPTION OF THE DRAWINGS

FIGS. 18-22 are software logic flow diagrams of a calibration procedure of the second embodiment;

FIGS. 26a-c, 28, 30, 32a-c and 36a-b are representations for the results for the software flow diagrams of FIGS. 25, 27, 29, 31, and 35, respectively.

DESCRIPTION OF THE PREFERRED EMBODIMENTS

The invention may be used to obtain through raster-stereographical techniques the topography of an object which is nontransparent and diffusing to light or which is transparent and nondiffusing to light, such as a cornea. The invention has particular application but is not limited as a clinical tool for the evaluation of topographic abnormalities of the corneal surface of a patient being a member of the animal kingdom, particularly a human. The invention will be described in terms of obtaining the topography of the cornea of a human, but is not limited thereto, and may be employed to determine the surface features or surface contour of an external body portion. The invention may also be used in dentistry, particularly in surgery, and also in plastic surgery practices.

Eyes that are emmetropic and eyes with keratoconus and severe astigmatism can be detected, analyzed, and corrected through surgery and contact lenses The invention can be easily used in an examination room or in an operating room.

As used herein, "limbus" is the border or edge of the cornea or clear optical zone and the sclera portion of the eye. The sclera is the white, fibrous outer envelope of tissue surrounding the cornea.

As used herein, "cornea" is the transparent anterior portion of the outer fibrous tunic of the eye, a uniformly thick, nearly circular convex structure covering the lens.

As used herein, a pixel is an individual picture element constituting a matrix used in a digital computer system for the resolution of images.

As used herein, the term "search window" applies to a size dimension which denotes how far from a reference line a search for a line segment will take place. Increasing or decreasing a "search window" means to look within a larger or smaller area about the reference line, respectively.

As used herein, the term "projection space" applies to that area on which the lines are projected, e.g., the cornea.

As used herein, the term "image space" applies to the several lines as they appear in the computer image As used herein, the term "fiducial mark" means a mark projected onto the measured surface.

As used herein, the term "viewing optics" or "imaging optics" are the set of optics through which the camera views the cornea.

As used herein, the term "projection optics" are the set of optics through which the lines are projected onto the cornea or onto the measured surface.

As used herein, the term "diopter" is defined as a unit of curvature and/or of power of lenses, refracting surfaces, and other optical systems.

Figures 1A, 1B:
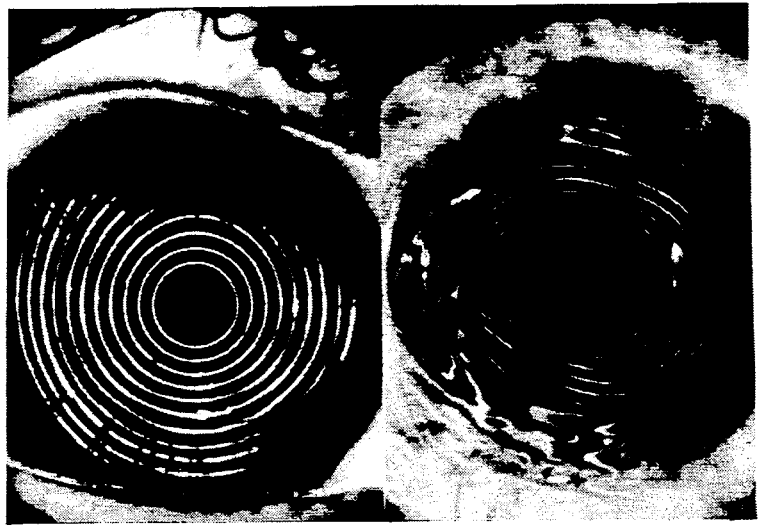
FIG. 1a is an illustration of a normal spherical cornea with a placido disk used in the prior art.
FIG. 1b is an illustration of a corneal transplant patient with astigmatic central cornea using the placido disk technique of the prior art.

FIG. 1a and FIG. 1b show the results of obtaining the corneal topography by the prior art practice of using the placido disk techniques. As stated hereinbefore, this technique has a placido disk consisting of a series of black and white concentric rings on a circular disk. The disk is placed in front of the eye, and the several rings are reflected by the cornea surface, and their position, size, and spacing in the reflected image are determined by the corneal shape. If the cornea is spherical, the rings appear to be round and regularly shaped as shown particularly in FIG. 1a. If the cornea is oval or astigmatic, the rings appear as being oval and the spacing between the rings varies along the different axes as shown in FIG. 1b. From these photographs it can be seen that much information is not available around the peripheral edges of the white rings in that a shadow is cast by the patient's eyelash, brow or nose.

A First Preferred Embodiment

FIGS. 2-13 illustrate a first preferred embodiment the present invention. In the invention, a grid is projected onto the cornea surface and is imaged as particularly illustrated in FIG. 2. It is preferred that the present invention employ a vertical grid which projects a light and dark line pattern onto the cornea. The image of the projected light and dark line pattern on the cornea is in FIG. 2, where one such light line is indicated at 6 and one such dark line is indicated at 8. As can be seen, the projected image covers the full cornea including the central optical zone and the limbus, which is the border of the edge of the cornea between the optical zone and the sclera portion of the eye.

Figure 2:
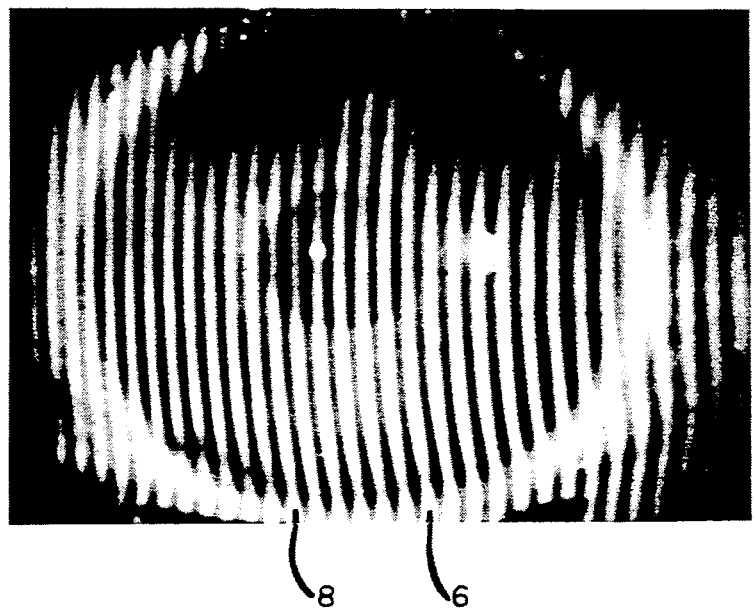
FIG. 2 is an illustration of an image of a vertical grid projected onto the eye obtained by the present invention.
Figure 3:
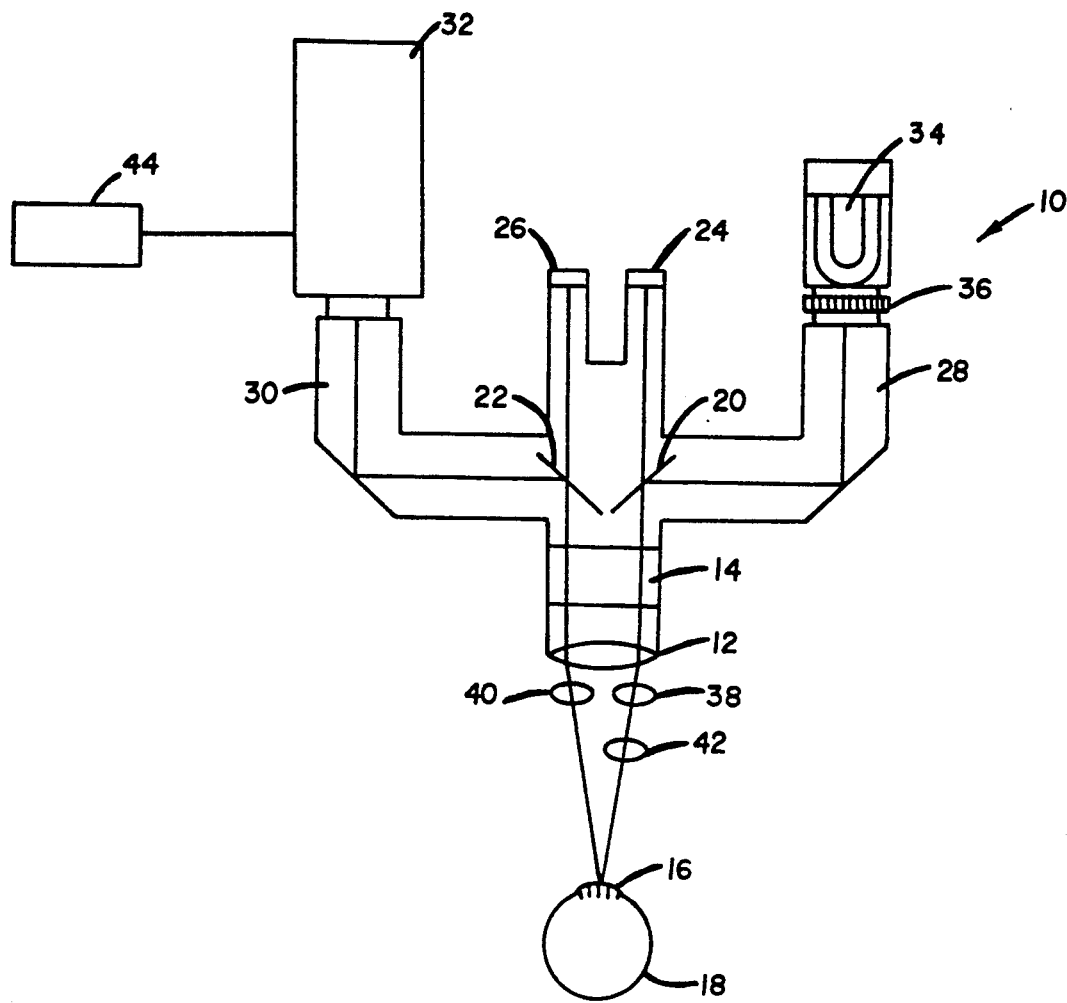
FIG. 3 is a schematic diagram of a microscope with beam splitter and projection system employed in the present invention.

The projected vertical grid which is imaged in FIG. 2 may be obtained through the employment of an apparatus 10 of the invention, which is shown schematically in FIG. 3.

In FIG. 3, preferably, apparatus 10 of the present invention employs an optical system. This optical system consists of an objective lens system 12 associated with a variable magnification turret 14. In lens system 12, one lens is concave and the other lens is convex. These lenses are used to magnify the cornea. The patient preferably places his or her head in a support (not shown) of the apparatus 10 of FIG. 3 so that the cornea 16 of the eye 18 is in line with the optical system. Also in line with the cornea 16 and the objective lens system 12 are two beam splitters shown schematically by a slanted hard line at 20 and 22, and two oculars shown at 24 and 26 for viewing of the cornea 16 by the operator of apparatus 10.

Preferably, apparatus 10 of FIG. 3 is a Zeiss or Topcon stereo photo microscope with a slit lamp system, or a similar system thereto which microscope has been modified to support the components of the invention. Two cine elbows indicated at 28 and 30 are mounted to the main body portion of apparatus 10 containing the beam splitters 20 and 22. These elbows 28 and 30 are shown to the right and left respectively in FIG. 3. Preferably, elbow 30 contains the slit lamp of a typical microscope which preferably is a Zeiss Model SL-6 or a Topcon model SL-6E presently used in stereobiomicrography Attached to elbow 30 is a video camera 32 which preferably is adapted to produce black and white images. Attached to elbow 28 is a coaxial illuminator/flash unit or projection system 34.

The Zeiss microscope, which has generally been used in a general examination of the eye, is modified by the addition of elbows 28 and 30 to support both video camera 32 and projection system 34. Mounted in front of unit 34 is a grid 36, which is a type of grating consisting only of vertical lines.

In still referring to FIG. 3, preferably, grid 36 is a well-known Rhonchi ruling with a one-to-one ratio of width and space. This grid 36 is mounted along the grid projected plane of the optical system of apparatus 10 in order to focus on the cornea at a desired point. Interposed between grid 36 and cornea 16 along an optical grid projection pathway is a filter 38. This filter 38 preferably is a cobalt blue excitation filter which preferably is a Zeiss SE40 filter. Along an optical imaging pathway interposed between video camera 32 and the cornea 16 is a yellow barrier filter 40, which preferably is a Zeiss SB50 filter. An infrared cutoff filter 42, which preferably is a Kodak filter, is interposed between grid 36 and the cornea 16 along the grid projection optical pathway.

Filters 38, 40, and 42 are held in apparatus 10 through holders (not shown) which are adapted to be easily mounted on the body of apparatus 10 for keeping the filters clean, and for preventing the scatter of light illuminated by illuminator/flash unit 34. Video camera 32 is connected to an image processor unit 44 which includes a computer. The computer electronically digitizes the projected image on the cornea by the grid 36, and stores and analyzes the data obtained therefrom, more of which is discussed further herein. Processor unit 44 is preferably a PAR CTS 100 unit provided by PAR Technology Corporation of New Hartford, N.Y.

In order to obtain a rasterstereographic image of the cornea, the operator focuses the optical system of apparatus 10. Preferably, ocular 26 is brought into focus by the operator. The illumination device on the slit lamp which is normally used for projecting a slit onto the cornea during examination generally is not used in the invention. The illuminator/flash unit 34 through cine elbow 28, the beam splitters 22 and 23, and the optical system provide the illumination required for focusing the objective lens system 12 onto the cornea 16. When the objective lens system 12 is at the proper focus distance, as observed by the operator through the viewing optics, the operator of apparatus 10 triggers the illuminator/flash unit 34 which follows the same pathway through the left viewing optics of the optical system of apparatus 10. The intensity of illuminator/flash unit 34 provides sufficient intensity to produce an image of the grid 36 projected onto the surface of the cornea 16.

As the surface of cornea 16 is transparent and non-diffusing the projected grid would under ordinary circumstances not be visible on the cornea. In order to provide a fluorescing surface on the eye to allow the projected grid to be visible, the invention employs a sodium fluorescein solution which is applied to the external corneal surface to stain the tear film of the eye. A sodium fluorescein solution which is commercially available and may be employed is known as Fluress, provided by Barnes Hind which contains 0.25 percent sodium fluorescein. The light from the flash of unit 34 passes through the cobalt blue filter 38 and the infrared cutoff filter 42.

As discussed hereinbefore, the cobalt blue filter 38 causes the fluorescein solution in the tear film on the surface of the eye to fluoresce in an alternating light and dark pattern which is produced by grid 36, and the infrared cutoff filter 42 shields the patient from the infrared transmissions of the flash tube unit 34, which unit 34 may be driven by approximately 400 volts.

This alternating light and dark line pattern is viewed by the video camera 32 through the yellow barrier filter 40 which as discussed hereinbefore, is used to increase the contrast of this alternating grid pattern. An example of this pattern is shown in FIG. 2. This image is automatically and electronically digitized and the data is stored and analyzed by image processor unit 44, through a procedure which is explained further with reference to FIGS. 4–13.

The apparatus 10 of the invention can be used in either an operating room or in an examination room. In the case where it is used in an operating room, preferably the objective lens 12 will have a focal length of approximately 175 millimeters. In referring again to FIG. 3, the angle formed by the plane along the centerline of the apparatus 10 and the projected optical pathway in which grid 36 and projection system 34 is located preferably will be about 6 degrees. This same angle will exist on the left side of apparatus 10 between the centerline and the imaging optical pathway where video camera 32 is located. Preferably the projection system 34 is spaced 100 millimeters away from cornea 16.

If the instrument 10 is to be used in an examination room, then preferably objective lens 12 will have a focal length of 100 millimeters. This shorter focal length objective will cause the angle between the centerline of apparatus 10 and the projected optical pathway and the angle between the centerline of apparatus 10 and the imaged optical pathway to become wider, i.e., the angle will become greater than the 6 degree angle existing when a 175 millimeter objective lens 12 is used.

If apparatus 10 of FIG. 3 is to be used to determine the topography of a solid object or a nontransparent object which is diffusing to light, then filters 38, 40, and 42 should not be used. Also, it is not necessary to apply the fluorescein solution to the object.

A feature of the present invention involves applying digital image processing techniques to the projected image of FIG. 2 to find the projected lines and to convert these lines into elevational information. Curvature information for the cornea is then extracted from the elevational information.

By using the elevation and curvature information the operator can obtain an intuitive and quantitative assessment of the shape and refractive power of the front surface of the cornea, or of the object under examination.

1 Computer Analysis

The computer analysis is discussed with reference to a cornea, however, here again, the procedure and results can quite easily be applied to any object under examination by apparatus 10, such as external body portions of both humans and other animals.

With regard to FIG. 2, the position and spacing of the vertical lines on cornea 16 provide the necessary information for determining the corneal topography. The computer of image processing unit 44 through an appropriate program is used to calculate the corneal surface elevation trigonometrically by comparing the horizontal displacement of the grid lines projected onto the cornea to the position of the vertical grid lines when projected onto a two-dimensional flat plane.

From these data, a two-dimensional matrix of elevation points is created. The number of data points in a horizontal direction is equal to the number of actual projected grid lines. The number of data points in a vertical direction for each grid line is limited only by the resolution of the system of video camera 32.

In order to limit the computer processing time, a vertical scaling proportional to a horizontal scaling is used. Preferably, surface elevations are calculated on a full cornea and the sclera. As discussed hereinbefore, the sclera is the white, fibrous outer envelope of tissue surrounding the cornea. In FIG. 2, it is apparent that the cornea covering the pupil and the iris is completely represented with the sclera surrounding the cornea around its periphery which is substantially darkened in FIG. 2. The grid lines of FIG. 2 vary in shape and intensity.

In the example of FIG. 2, in accordance with the invention the cornea was made opaque by topically applying the fluorescein solution onto the outer surface of the cornea, and the grid 36, through the cobalt blue filter 38, was projected onto the eye 18.

When performing elevational calculations on the full cornea and sclera, the spacing between horizontal points for the two-dimensional matrix is approximately 0.4 millimeters. If desired, a higher magnification can be used, reducing this distance to 0.1 millimeters. The resultant matrix size then is approximately 45 horizontal data points by 60 vertical data points for a total greater than 2500 elevation points across the surface of the cornea.

Figure 4:
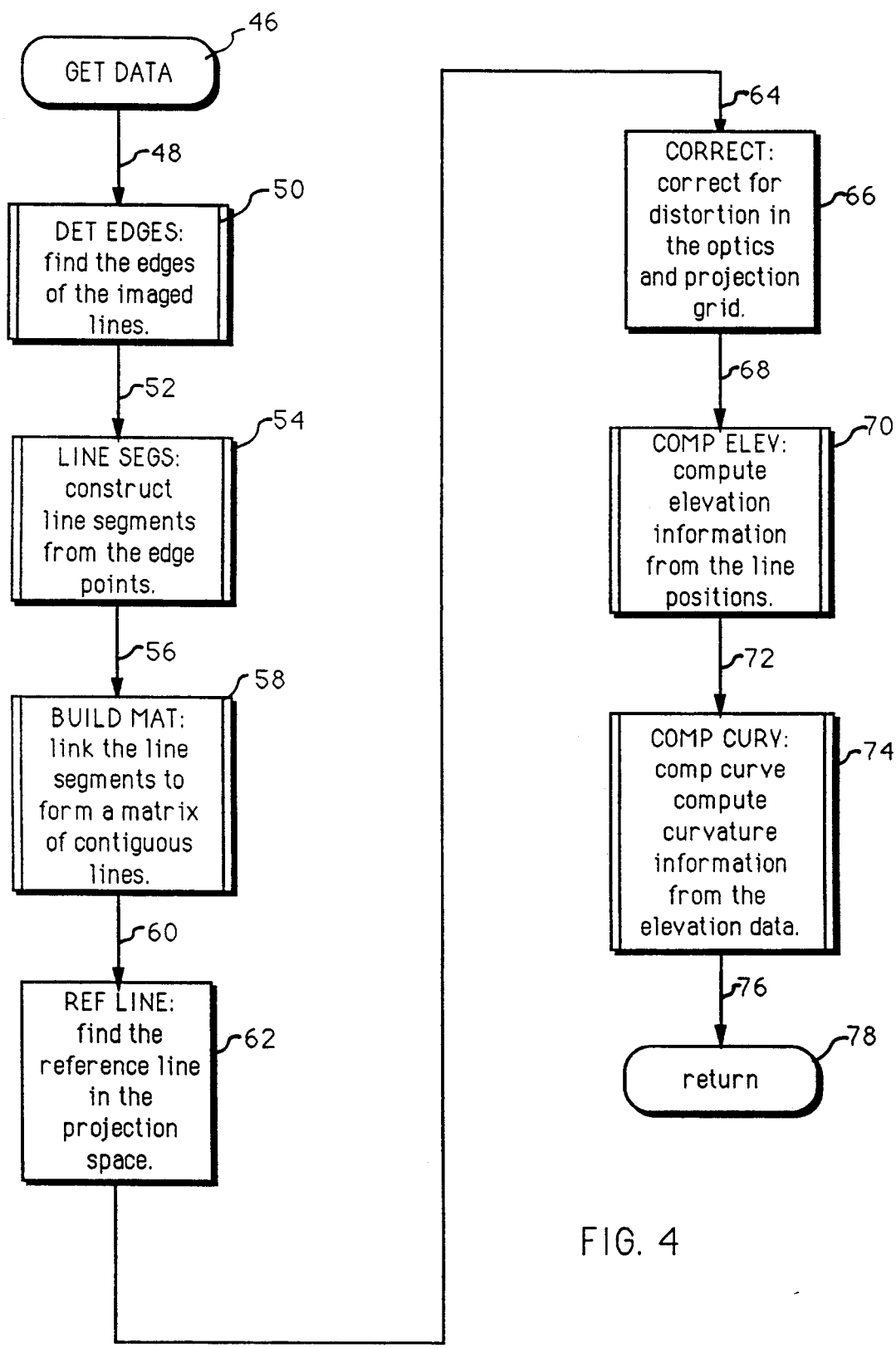
FIG. 4 is a logic flow diagram of the main program for digitizing the image on the cornea of FIG. 2 by a computer.

The software for the image processing unit 44 is illustrated in terms of flow diagrams in FIGS. 4–8. The main software program for determining the topography of the surface of a cornea is illustrated in FIG. 4, and is written in terms of subroutines, the flow diagrams for which are shown in FIGS. 5–8. These computer programs have been developed a) to identify the grid lines, b) to calculate the elevation points from which curvature information is derived, which has been discussed to some length hereinbefore, and c) to display the results.

Referring more specifically to FIG. 4, the main software program of processing unit 44 of FIG. 3 sets forth several directives for performing steps a), b), and c) in the preceding paragraph. The first step is to obtain the data of, for instance, the imaged grid lines on the cornea of FIG. 2. This step of obtaining this data is indicated at 46. The imaged grid lines are those that appear in the computer image.

Once the data is obtained, the processing unit 44, as indicated at 48, employs the first subroutine indicated at 50 and identified as "DET EDGES". As is apparent, this subroutine finds the edges of the imaged grid lines on the cornea From this the main program moves down as indicated at 52 to the next subroutine indicated at 54, and entitled "LINE SEGS". This subroutine is designed to construct a line segment from the edge points found in the subroutine "DET EDGES".

Once all the line segments are constructed the main program moves down as indicated at 56 to the subroutine en "BUILD MAT" indicated at 58. This subroutine is designed to link the line segments together to form a matrix of contiguous lines. After the elevation of the imaged grid lines are computed, two additional steps indicated by numbers 60, 62, 64, and 66 are performed by processing unit 44. The first step indicated at 62 is referred to as "REF LINE". This step finds the reference line in the projection space. A correction for the distortion in the optics and in the projection grid lines is found by the step indicated at 66 and is referred to as "CORRECT".

These two steps lead as indicated at 68 to the next subroutine entitled "COMP ELEV". This subroutine is designed to compute the elevation of the imaged grid lines from the line positions found by the previous subroutine. This subroutine "COMP ELEV" is followed as indicated at 72 by the subroutine indicated at 74 entitled "COMP CUR".

This "COMP CUR" subroutine is designed to compute the curvature information of the cornea from the elevation data obtained in the subroutine "COMP ELEV".

The subroutine for computing the curvature is not disclosed herein but is indicated as being a preferred step in the invention. The method preferably used in the invention for calculating the radius of curvature is the simplex computer algorithm to best fit an arc to the elevation points. This simplex algorithm is well-known in the computer industry where software is readily available.

Once the curvature is determined, the main program of FIG. 4 is exited, and the processing unit 44 through a display device (not shown) visualizes the results of the algorithm of FIG. 4, as shown for instance in FIGS. 10, 11, 12, and 13, more of which is to be discussed hereinafter along with more details of the several subroutines of FIGS. 5, 6, 7, and 8.

a) Identifying the Grid Lines

A further description of the several subroutines of the algorithm of FIG. 4 will now be given.

Referring again to FIG. 5, the first subroutine "DET EDGES" is called up by the main program to determine the edges of the imaged lines. At this time the lines of the vertical grid 36 projected onto the cornea are visible in the digitized image.

Figure 5:
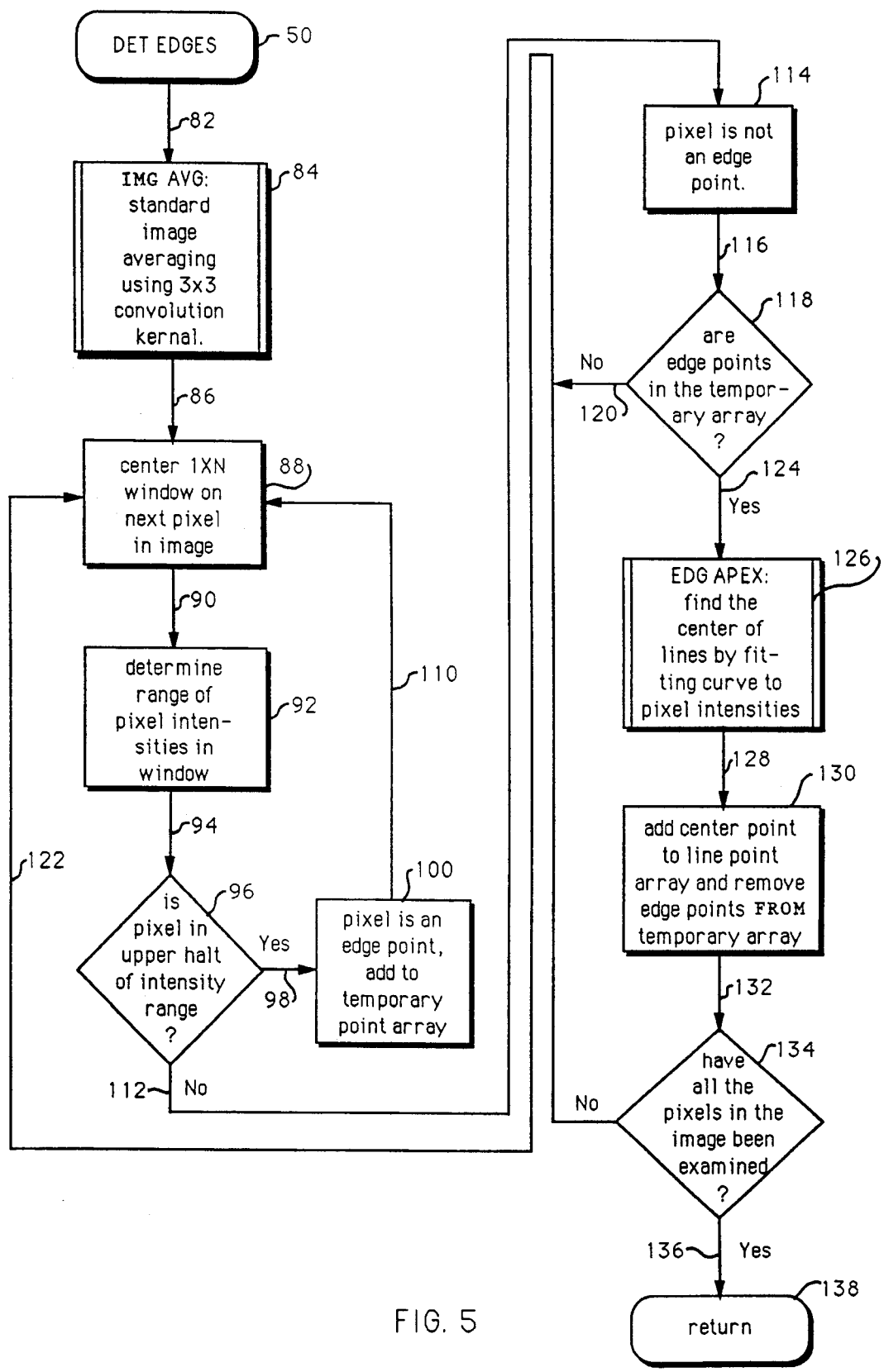
FIGS. 5, 6, 7, and 8 are logic flow diagrams of subroutines utilized in the main program of FIG. 4, including respectively a determination of the edges subroutine; a construction of the line segments subroutine, a forming of a matrix subroutine; and a computation of the elevation in formation subroutine.

This subroutine of FIG. 5 is designed to attempt to find the edges of the projected lines of every third row of the image. This algorithm of FIG. 5 uses the wavelike distribution of pixel intensities related to the light to dark transition of the lines to find the near exact center of each line.

The subroutine of FIG. 5 illustrates the several steps involved in accomplishing this. The first step as indicated at 82 and 84 is to use a $3 \times 3$ convolution kernel to perform a standard image averaging on the whole image. The second step as indicated at 86 and 88 is to center a $1 \times N$ window on a pixel in the image. The third step as indicated at 90 and 92 is to determine the range of the pixel intensities in the window. This is accomplished by looking at the numeric pixel intensities of the pixels in the window for the lowest and the highest values. These values mark the range. As indicated at 94 and 96 the next step is to determine if the pixel is in the upper half of the intensity range.

If the answer is "yes" as indicated at 98 and 100 then the pixel is considered to be an edge point. This edge point is added to a temporary point array. As indicated at 110, from the step in block 100, the subroutine goes back to block 88 where these steps are repeated for the next pixel in the image. If the pixel under study is not in the upper half of the intensity range, then as indicated at 112 and 114 the pixel is not considered to be an edge point.

The next step is to ask whether there are any edge points in the temporary array. This is indicated at 116 and 118 If the answer is "no," then as indicated at 120 and 122 the subroutine returns to block 88 to examine the next pixel in the image. If the answer is "yes," then as indicated at 124 and 126 the program proceeds to the step entitled "EDG APEX".

This algorithm in FIG. 5 finds the center of the line formed by the points in the temporary array by fitting a curve to the pixel intensities of the edge points. As numbers 128 and 130 indicate the center point is added to the line point array, and the edge points are removed from the temporary array. The final step is indicated at 132 and 134 where it is determined as to whether all the pixels in the image have been examined.

If the answer is "no," then the program returns to the appropriate location of block 88 whereby the next pixel in the image is examined. If "yes," the subroutine program returns to block 54 of the main program of FIG. 4 as indicated at 136 and 138.

Figure 6:
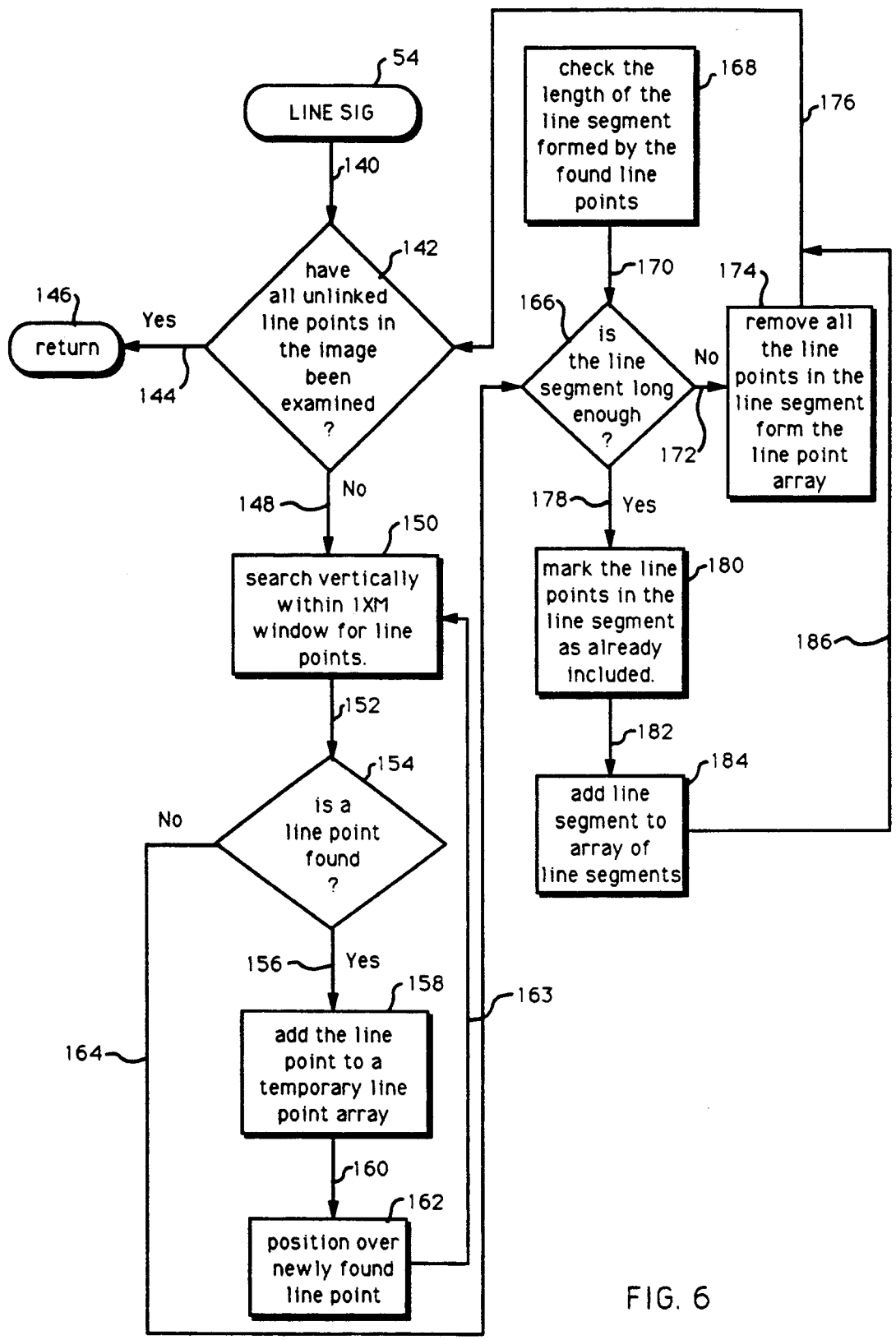

The flow diagram of the subroutine of FIG. 6 is identified as "LINE SEG", and is used to construct line segments from the line points. This portion of the main program is activated when all the line points of the lines of every third row of the image have been found by the subroutine of FIG. 5.

This algorithm of FIG. 6 attempts to link the several line points to form a series of continuous line segments. In order to account for possible noise from not being included, restrictions are applied when linking the line points.

A root line point is found. When searching for other line points which are linked to a root line point, a search window is specified in which the search is made. This limits the possibility of incorrect line points being linked to form a line segment. Once the line segments are found, a length restriction is applied to discard those line segments which may have been inadvertently created. Referring specifically to FIG. 6, the flow diagram of this subroutine illustrates the several steps involved in forming the line segment forming operation.

The first step as indicated at 140 and 142 is to ask whether all the unlinked line points in the image have been examined as specifically shown in block 142. If "yes," then the subroutine returns to the main program of FIG. 4 as indicated by numbers 144 and 146. If "no," a further search is made vertically within a $1 \times M$ window for neighboring line points as indicated at 148 and 150. The question "Is a line point found?" is asked as indicated at 152 and 154. If a line point is found, the line point is added to a temporary line point array as indicated at 156 and 158.

The next step from the step at 158 is to position the $1 \times M$ search window over the newly found line point and to find other line points linked to the newly found or root line point by a continuous search as indicated at 160 and 162. From 162, the subroutine by line 163 returns to block 150. If no line point is found by the step at 154, then as indicated at 164 the question is asked at 166 as to whether the line segment is long enough.

As indicated at 168 and 170 the algorithm of FIG. 6 is designed to check the length of the line segment formed by the found line points followed by asking the question indicated at 166. If "no," then all the line points in the line segment are removed from the line point array as indicated at 172 and 174, and the subroutine returns to 142 to the beginning of this loop as indicated at 176. If "yes," then as indicated at 178 and 180 the line points in the line segment are marked as being included.

As indicated at 182 and 184 of FIG. 6, one of the final steps is to add the line segment to the array of line segments. From this step, the algorithm returns as indicated at 186 to the beginning of the subroutine at 142. If certain conditions are met, this algorithm is completed and the operation is returned to the main program of FIG. 4.

Figure 7:
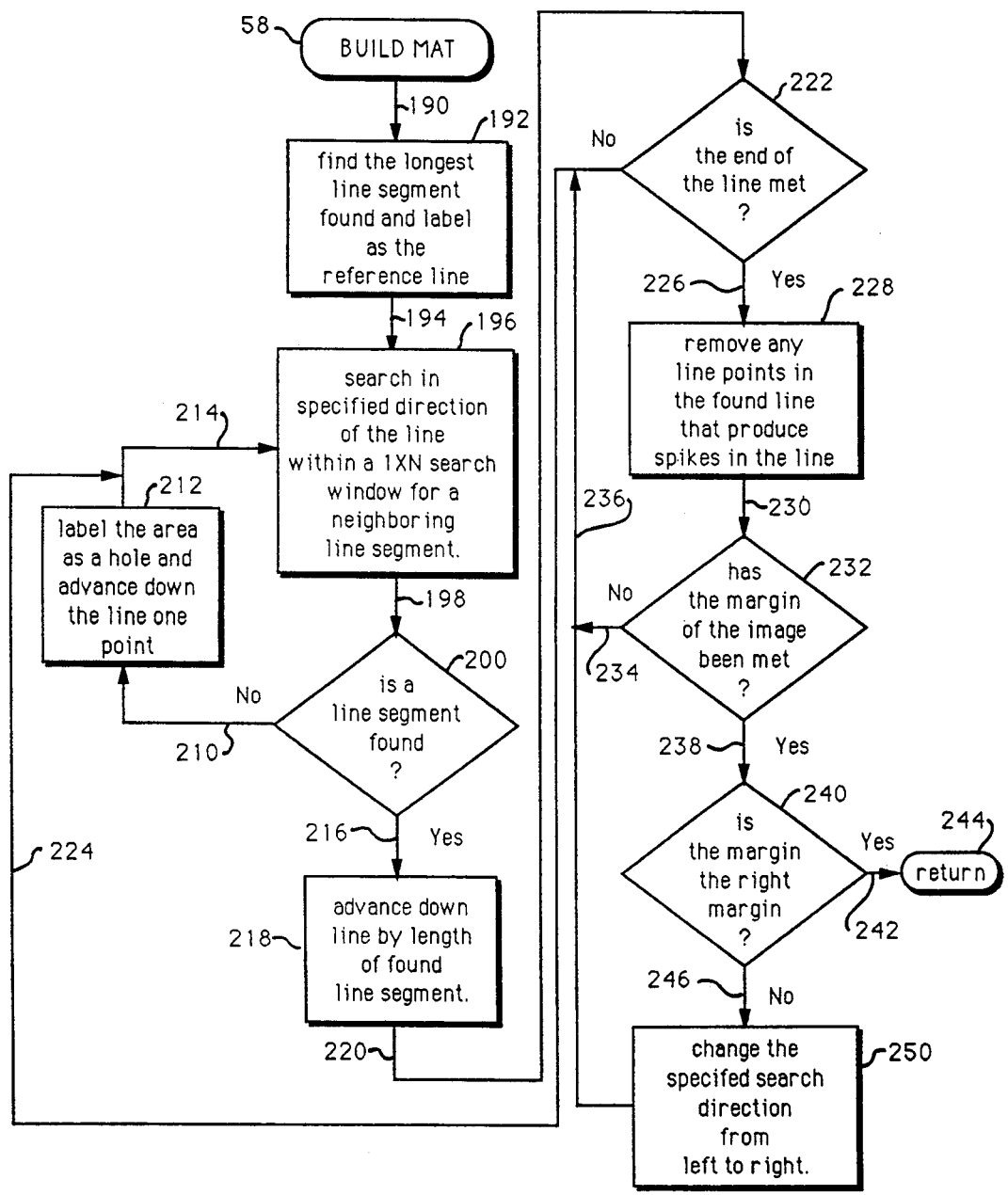

Once continuous line segments are formed by the subroutine of FIG. 6, the next step is to link the line segments to form a matrix of contiguous lines. The subroutine of FIG. 7 illustrates the several steps for performing this operation. These contiguous lines are referenced relative to each other in order to determine their position on the cornea.

This process involves first finding the longest line determined in the "Line Seg" subroutine of FIG. 6. This line is used as a reference line. The subroutine of FIG. 7 entitled "Build Mat" then looks horizontally to find the next vertical line segment. The search is for each line point in the reference line segment constrained within a search window. If a line segment is not found within the allowed range then there is no data next to the reference line at this line point position. The search continues for every line point in the reference line. Once all the line points in the reference line have been searched, a second test for line point validity is applied. The average spacing between the reference line and the newly found line is computed. This is done by finding the difference between the average horizontal positions of all the line points in the reference line and the average horizontal position of a line point in the new line. Any line points in the newly found line which are farther than 1.5 times the average spacing commonly referenced to as "spikes" are excluded from the new line.

This procedure for the reference line is then repeated for the newly found line which then becomes the reference line. The search window is also changed from the previous dimension to 1.5 times the average spacing which has just been computed.

The search window is a size dimension which denotes how far from the reference line a search for a line segment will take place. Increasing or decreasing the search window means to look within a larger or smaller area about the reference line respectively.

The final output of the subroutine of FIG. 7 is a two-dimensional array of image positions denoting the points of the located lines.

The subroutine of FIG. 7 continues to reference line segments starting at the first reference line and proceeding to the left side of the image until the left side of the image is reached. The subroutine then returns to the original reference line and repeats the same process but this time moving to the right side of the image. When the right side of the image is reached, all the line segments have either been linked to form continuous lines or have been discarded.

The several steps involved for the final output are shown in the algorithm of FIG. 7. The first step is to find the longest line segment and to label it as the reference line as indicated at 190 and 192. The next step is to make a search in a specified direction within a 1×N dimension search window for a neighboring line segment as indicated at 194 and 196. From this, the next step as indicated at 198 and 200 is to ask whether a line segment is found.

If "no," then as indicated at 210 and 212 in FIG. 7 the area is regarded as an empty space, and the search is advanced to the next point in the reference line from 212. From 212, the algorithm returns to the step of 196 as indicated at 214. If "yes," then as indicated at 216 and 218 the search is advanced down the line equivalent to the length of the found line segment.

The next step is to then ask whether the end of the reference line is met as indicated at 220 and 222. If "no", the subroutine returns as indicated by 224 to the beginning of the main loop of this subroutine to continue the search by the step at 196. If "yes," the next step is to remove any line points in the found line that produce "spikes" or deviations from the found line as indicated at 226 and 228.

The next question as indicated at 230 and 232 in FIG. 7 is to ask whether the margin of the image has been met. If "no," then as indicated at 234 the subroutine by way of line 236 returns to the beginning of the main loop to continue the search by the step at 196. If "yes," the next step is to ask if the margin is the appropriate one as indicated at 238 and 240. If the answer is "yes," the subroutine as indicated at 242 and 244 returns to the main program of FIG. 4. If the answer is "no," the directive is given to change the specified search direction from left to right as indicated at 246 and 250, and the subroutine is returned as indicated by line 236 to the beginning of the main loop to continue the search by the step at 196.

Figure 8:
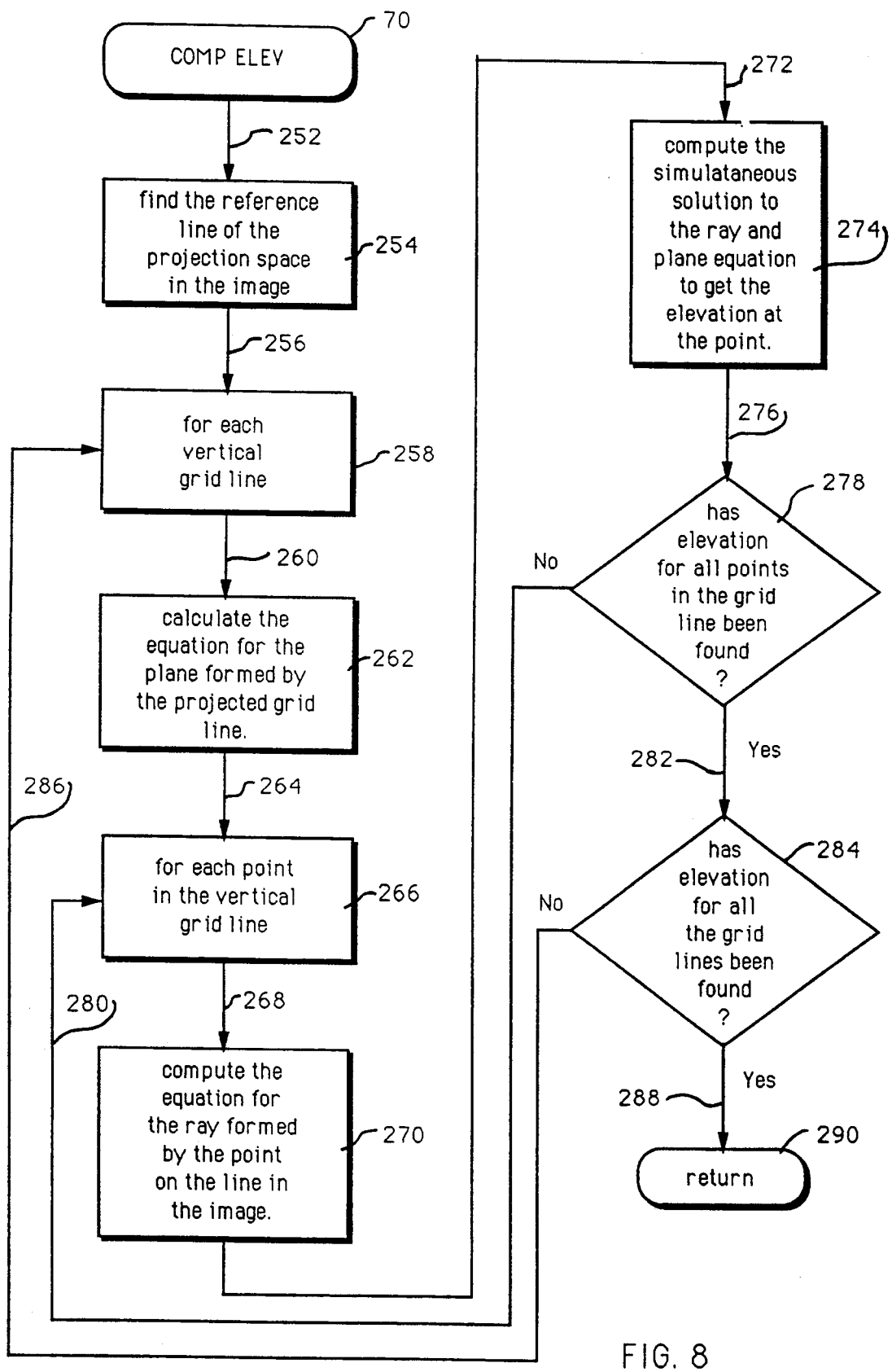

Steps 62 and 66 of the main program of FIG. 4 indicate the two additional processes which are preferably completed before the subroutine of FIG. 8 is employed.

As Step 62 indicates, the next process is to find the reference line found in the "BUILD MAT" subroutine in the projection space. To clarify this, once all the lines have been located in the image space which as mentioned hereinbefore are those lines as they appear in the computer, their location within the projection space is determined. The projection space as defined is the cornea onto where the lines are projected.

This preceding step is done in order to calculate the correct elevation and to perform correction for distortion. The system locates a fiducial mark which is regarded as a standard of reference on one of the lines. The position of this line in the projection space is known and from this known position all the remaining lines are referenced to the projection space.

A fiducial mark is formed by introducing a 'break' in one of the lines in the grid used to form the projected lines. If the lines are focused properly onto the cornea, the break in the line will appear at a specific set location in the image. The "BUILD MAT" subroutine of FIG. 7 will check this known location against the location of holes that have been found. If no hole has been found at this location the lines were not focused properly. The operator of apparatus 10 is informed of this and he or she must take another picture to process.

Since this fiducial mark position is known at optimum focus on the cornea, it is also known at optimum focus on a flat plane. Since all lines are referenced to each other, and, in turn the fiducial mark, the actual displacement of each line from its actual position on a flat plane can be determined.

The step in No. 66 provides for a correction for any distortion in the optic system and in the projected grid 36 of apparatus 10. Since the optics and the grid 36 are not ideal, there will be inevitably some distortion and imperfections in the system. In order to assure accuracy, this must be corrected.

These corrections are obtained by analyzing a known flat surface during a calibration procedure. The deviations from the flat surface are recorded and later applied to the lines projected onto the corneal surface. In the calibration procedure the grid spacing on the flat surface or plane is a known constant; any elevation or depression from this plane deviates the grid line according to the following Equation No. 1:

$$Deviation\ of\ Grid = (Lines\ shifted \times SP) - HD,$$

where the lines shifted is the number of grid lines which are either positive or negative from the reference line to the line to be measured, SP is the grid spacing constant as projected onto the flat plane, and HD is the horizontal distance measured along a horizontal of the flat plane from the reference point to the point on the line to be measured.

b) Calculating the Elevation Points and Computing Curvature Information

Once the lines and their locations within the projection space are known, the elevation information is determined according to the subroutine of FIG. 8 having the heading "COMP ELEV". The operation of this subroutine involves knowing the geometry of the optical system and the video camera 32 used in the imaging procedure performed by apparatus 10 of the invention.

One of the important steps for computing the elevation of the points is to determine the equation of the plane formed by the grid line.

The equation of the plane formed by the grid line is determined by a calibration step. This step involves projecting the lines onto a flat surface. The lines are then detected and referenced as stated hereinbefore. For each vertical line two points on the line are used. One point is from the upper half of the line and the other point is from the lower half of the line. By knowing the focal length of the optics (focal length of a standard C-mount adaptor is 35 millimeters), the distance between the stereo optical pathways and the focal length of the objective lens 12 of the optical system to a 'ray' for each point can be calculated using standard vector mathematics and standard 'pin-hole camera' geometric principles.

Once the two rays have been found, the equation for the plane can be found by computing the vector cross product of the two vectors. This is performed for each vertical line and is stored in a file in the computer. This file is retrieved whenever a measurement is made.

The next step is to determine the equation of the ray formed by each point in the imaged lines. This is performed for each line point in each line found projected onto the corneal surface. This produces a ray for each line point in the line. The ray representing the point in the line and the plane of the line are solved simultaneously to determine the point of intersection. This is done using standard ray/plane intersection vector mathematics, the methods of which are outlined in standard analytical geometry textbooks.

Programs for determining the two equations and for simultaneously solving the two equations are readily available in the computer industry. The final result or output is a two dimensional array of elevation information for the front surface of the cornea which, in fact, is the topography of the front surface of the cornea.

The subroutine of FIG. 8 shows the several steps involved in computing the elevational information, as described hereinabove. The first step as indicated at 252 and 254 is to find the reference line of the projection space in the image. For each vertical grid line, the equation for the plane formed by the projected grid line is looked up as indicated at 256, 258, 260 and 262. Then, as indicated at 264, 266, 268, and 270 for each point in the vertical grid line, the equation for the ray formed by the point on the line in the image is computed.

The next step as indicated at 272 and 274 is to compute the simultaneous solution of both the ray and the plane equations in order to obtain the elevation at that point. The next step is to inquire as to whether the elevations for all the points in the grid line have been found as indicated at 276 and 278. If "no," the subroutine as indicated at 280 returns to 266 which forms an inner loop which produces this result for each point in the vertical grid line. If the answer is "yes," the next inquiry as indicated at 282 and 284 is whether the elevation for all the grid lines has been found. If "no," the subroutine as indicated at 286 returns to 258 forming the main outer loop for this subroutine. If "yes," the subroutine returns to the main program of FIG. 4 as indicated at 288 and 290.

Figure 9:
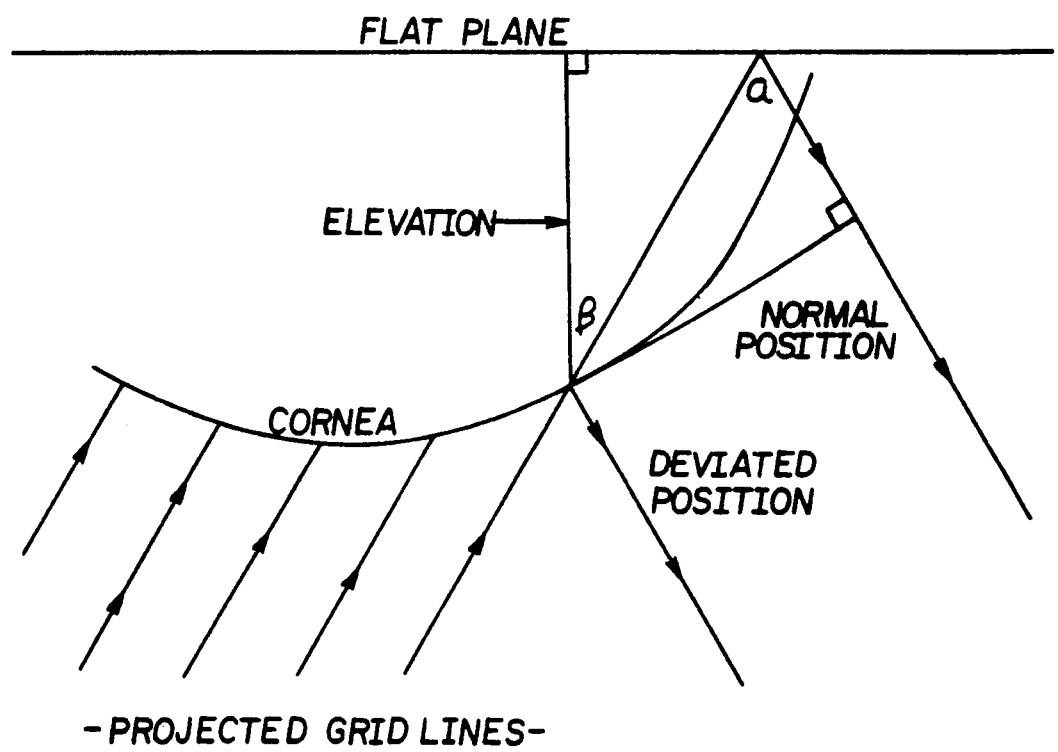
FIG. 9 is a schematic diagram showing grid lines displaced on the cornea from an assumed normal position and a trigonometric solution for elevation employed by the present invention.

Referring now to FIG. 9, there is illustrated the projected grid lines onto the cornea, and a normal positioning and a deviated positioning for the lines.

The greater the elevation of the cornea, i.e., the closer it comes to the projection and imaging lens 12 in FIG. 3, the greater a grid line deviates toward the projection lens side, or to the left in referring to FIG. 9. The matrix point elevations that are calculated from the grid line in the immediately preceding sentence are also moved proportionately to the left.

This establishes the relationship between the topography of the cornea and its effect on the movement of the projected lines. If a line is projected onto a surface and the surface is moved away from the lens 12 in FIG. 3, the line would appear to move to the right in the image. A series of vertical lines would appear close together when the surface upon which they are projected is moved close to lens 12, and become farther apart as the surface is moved away from lens 12.

The relationship between line movement and elevation change is denoted by Equation No. 2 which is derived from FIG. 9:

$$z = \cos\beta \times h / \sin\alpha$$

where:
$\alpha$ = angle between the imaging pathway and the projection pathway,
$\beta$ = half of angle
h = the change in the line position on the cornea, and
z = the elevation change.

As stated hereinbefore, a two-dimensional array of elevation information is obtained by the flow diagram of the subroutine of FIG. 8. This matrix can then be stored for future use or processed for further image analysis, including computing the curvature information of the cornea.

The subroutine as indicated at 72 and 74 of FIG. 4 entitled "COMP CUR" performs the function for obtaining the curvature information. In this subroutine, the elevation information is converted into curvature information by any of the well-known methods for fitting curves to data. Preferably in the invention, the fitting of a curve to data is done by a simplex algorithm method, which is set forth in a standard math textbook. The simplex algorithm may preferably be a computer program easily available in the computer industry.

Reference for fitting curves to data by the simplex algorithm is made to an article entitled "Fitting Curves to Data, The Simplex Algorithm Is the Answer," by M. S. Caceci and Wm. P. Cacheris, Byte Magazine, May, 1984. The computer of processing unit 44 displays a cross sectional view of the cornea along any axis by plotting the elevation points of the matrix along any particular line. The radius of curvature is calculated using the same method.

Curvatures can be determined for any axis either for the average across the full cornea or for a small portion of it. The final step is to write out the values and to return this subroutine to the main program of FIG. 4 in order to produce the desired displays similar to that shown in FIGS. 10-13.

c) Displaying the Results

Figure 10:
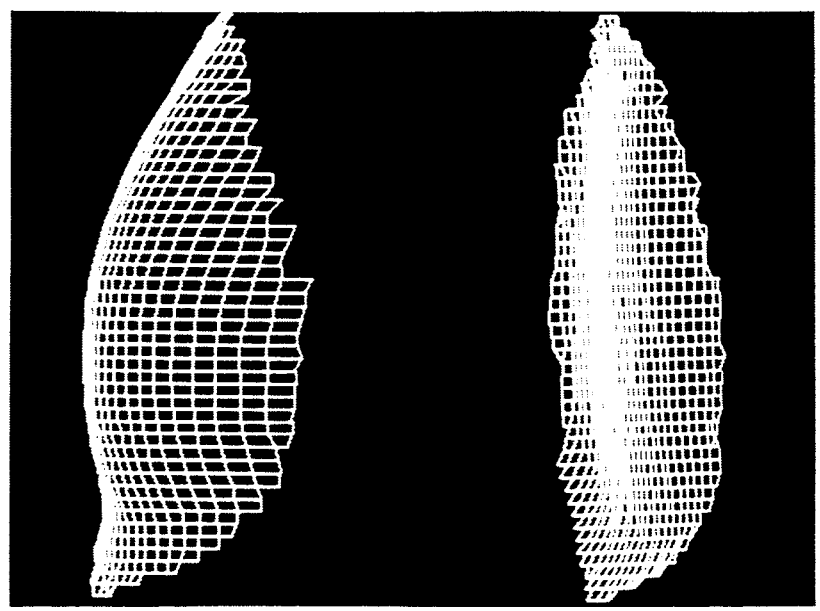
FIG. 10 is an illustration showing on the left hand side an orthogonal view of a normal cornea, and on the right hand side the same cornea with the common curve removed which are derived by the display methods used in the present invention.

Using the matrix file formed in the subroutine of FIG. 8, and by calculating the curvature, an image of the cornea can be represented in several forms, some of which are demonstrated in FIGS. 10, 11, 12, and 13. Standard graphics processing techniques which are known in the computer industry can be used to rotate the cornea around the X or the Y axis. The left portion of FIG. 10 shows an orthogonal view of a normal cornea rotated 80 degrees to the right to view the shape of the cornea across the bridge of the nose. The right portion of FIG. 10 shows the same cornea from the same angle, but the common curve of the cornea has been subtracted out to accentuate distortions from a spherical shape.

Figure 11:
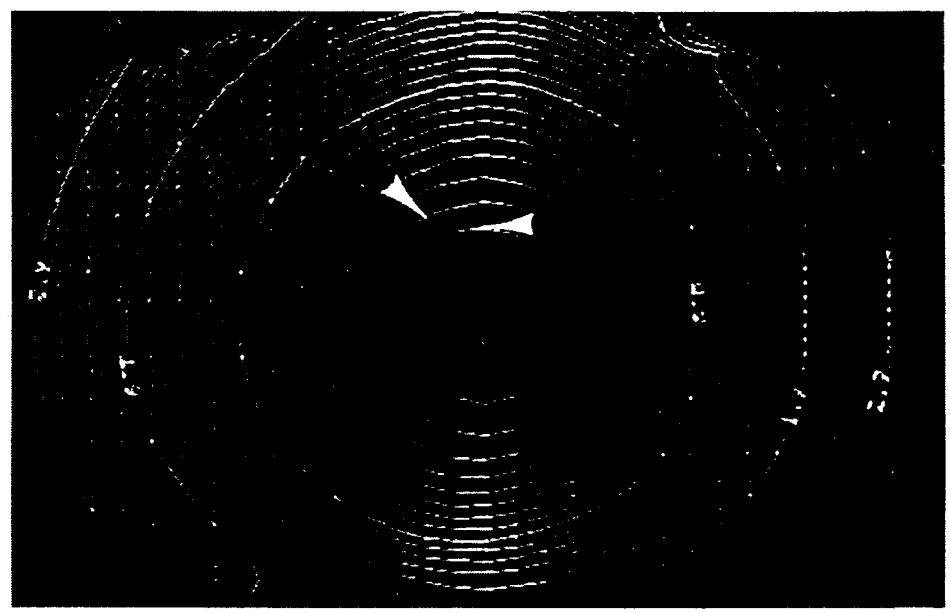
FIGS. 11, 12, and 13 are illustrations of contour plots of the cornea derived by the display methods employed in the present invention.
Figure 12:
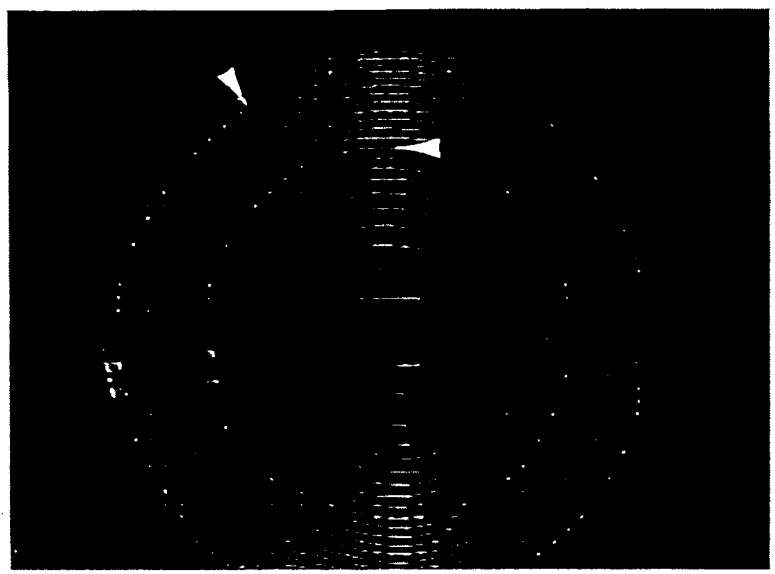
Figure 13:
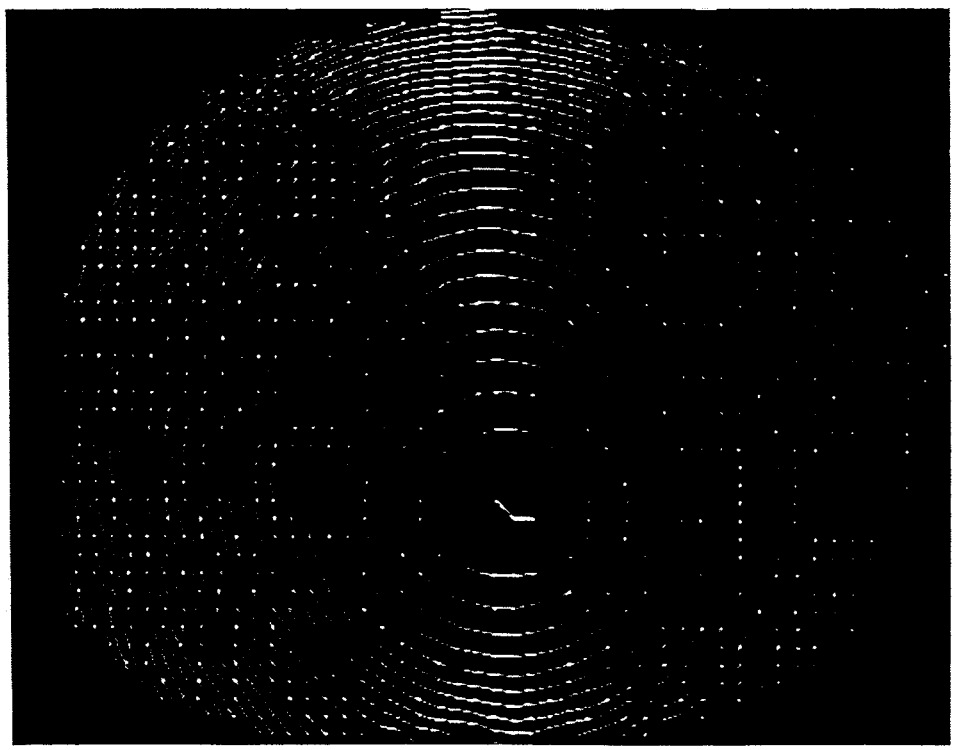

Contour plots of the cornea are also shown in FIGS. 11, 12, and 13. In FIG. 11, each line on the plot represents an area of equal height. In FIG. 11, each line represents an elevation change of 0.1 millimeters. The image of FIG. 11 is magnified 2.5 times to obtain the data for FIG. 12. Each contour line in FIG. 12 represents 0.0125 millimeters in elevation. In view of the higher magnification rate of FIG. 12, only the central 3 millimeters of the cornea is represented. FIGS. 11 and 12 illustrate that the topography of a portion of the cornea represented therein is substantially curved.

FIG. 13 illustrates a full cornea of a patient with astigmatism, where the circles of the contour plot illustrate a substantially flatter topography for the cornea in the horizontal plane.

The system of the present invention comprising the apparatus 10 of FIG. 3 and the main program of FIG. 4 was calibrated using four steel balls of varying diameters as a standard for measuring curvature. The balls were sprayed with paint to provide a non-reflective surface and then measured with a micrometer.

Using the projected grid 36 each ball was photographed a total of four times. The images were processed to find a radius of curvature. The average error of the sixteen measurements was 0.060 millimeters with a range of +0.11 to −0.16 millimeters. For the larger diameter balls, the system of the present invention tended to overestimate the true curvature, while for the smallest diameter ball, the system tended to underestimate the true curvature of the ball. For each of the four balls, the measurements were approximately 0.10 millimeters or less. This calibration technique for obtaining a measurement for curvature is familiar to those skilled in the art.

The accuracy of the method of the invention is dependent on several variables. These variables are: the resolution of video camera 32; the magnification of variable magnification turret 14; the angle $\alpha$ between the projected image and the viewing optics; and the number of projected lines of grid 36. As the magnification of the corneal image increases, or the resolution of the video camera 32 increases, the change in depth represented by each pixel is reduced, thereby increasing the accuracy of the measured displacement of the lines of grid 36.

The following paragraphs have reference to Equation No. 2 where $z = (\cos \beta \times h)/\sin \alpha$ of FIG. 9.

If the magnification were increased, then the number of lines projected onto the measured surface would increase per unit area. In other words, each line covers a smaller area and movement of these lines covers a smaller area of the measured surface. Therefore, the ability to measure h becomes more sensitive and, in turn, the ability to measure elevation change becomes more sensitive.

If the resolution of the computer's imaging system is to be increased, the computer would then measure the change in the line position more precisely and, thus measure the elevation more precisely. The sensitivity between the movement of the line and the change in elevation does not change.

If $\alpha$, the angle between the imaging pathway and the projection pathway is increased, the sensitivity between the movement of the line and the change in elevation would increase, making the elevation detection more sensitive. This can be shown mathematically by determining what the quantity $\cos \beta / \sin \alpha$ would be if the angle $\alpha$ is increased.

If $\alpha$ is decreased, $\cos \beta / \sin \alpha$ increases. Thus, the same h equals a larger z, i.e., the same line displacement equals more elevational change. The ability to increase the angle is limited by the curvature of the cornea. If the angle is too large, the imaging side of the cornea will be completely shadowed by the cornea itself, and no lines will be projected onto that side of the cornea. With normal corneal curvature of 7.0 mm taken into account, the angle can be increased up to about 40 degrees with little or no problems in the efficiency of the system of the invention.

The accuracy of the measurement of the topography of the cornea is proportional to the angle of separation between the projected image and the viewing or imaging optics. As discussed hereinbefore, the viewing or imaging optics are the set of optics in apparatus 10 through which the video camera 32 views the cornea 16. The projection optics are the set of optics in apparatus 10 through which the lines are projected onto the cornea 16 or onto a measured surface. As the angle of separation between grid 36 and video camera 32 increases, so does the sine of the angle, which angle is used to determine the elevation of the surface of the cornea, making the depth represented by a one-pixel change in displacement of the grid lines smaller as already discussed herein.

Increasing the angle of separation between grid 36 and video camera 32 results in a greater number of the projected grid lines falling on the side of the cornea where projection system 34 and grid 36 are located. This tends to diminish the accuracy of the system on the total cornea. This effect is exaggerated for demonstration purposes in FIG. 9. Due to this it is not clear at this time whether a substantial change in the angle of separation is beneficial.

Increasing the number of lines projected onto the cornea could easily be done by changing the grid 36 of projection system 34 of FIG. 3. Doubling the number of the grid lines would result in an increase in the number of elevation points in the formed matrix. For example, the 2500 points of the example given hereinabove would be increased to approximately 10,000 elevation points across the corneal surface.

A Second Preferred Embodiment

Figure 14:
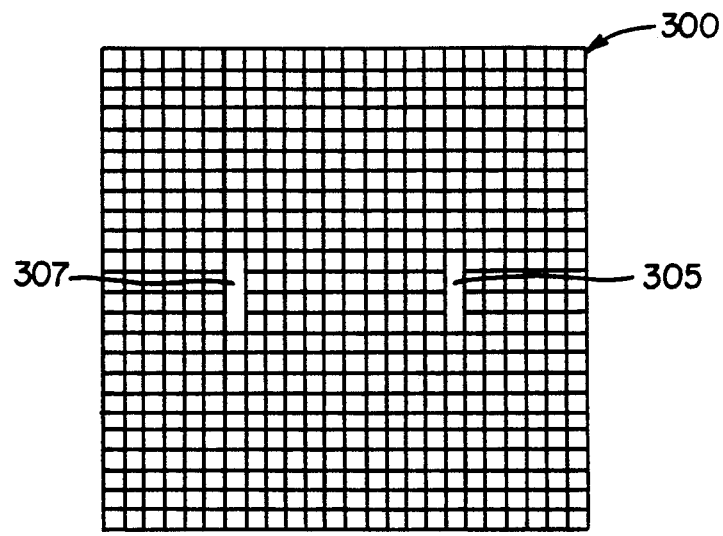
FIG. 14 illustrates a grid pattern for a second preferred embodiment of the invention.

FIGS. 14-36 essentially represent a second preferred embodiment of the invention. FIG. 14 illustrates an example of a design and construction of a projection grid 300 with intersecting generally horizontal and perpendicular lines. This grid 300 is preferred in this second embodiment instead of the Rhonchi ruling grid of FIG. 2 which grid has generally vertical lines.

Figure 15:
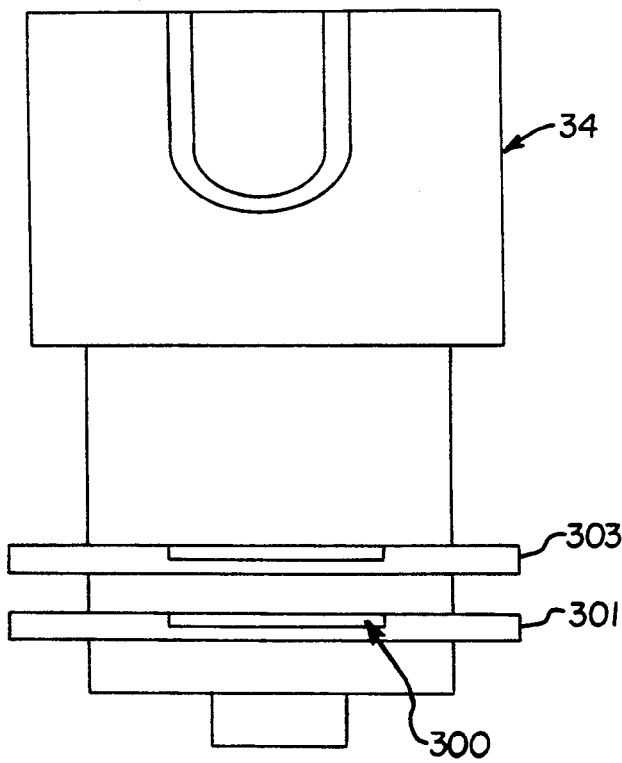
FIG. 15 illustrates in plan view a flash illumination system of the device of FIG. 3 used in the first and second embodiments of the invention.
Figure 16:
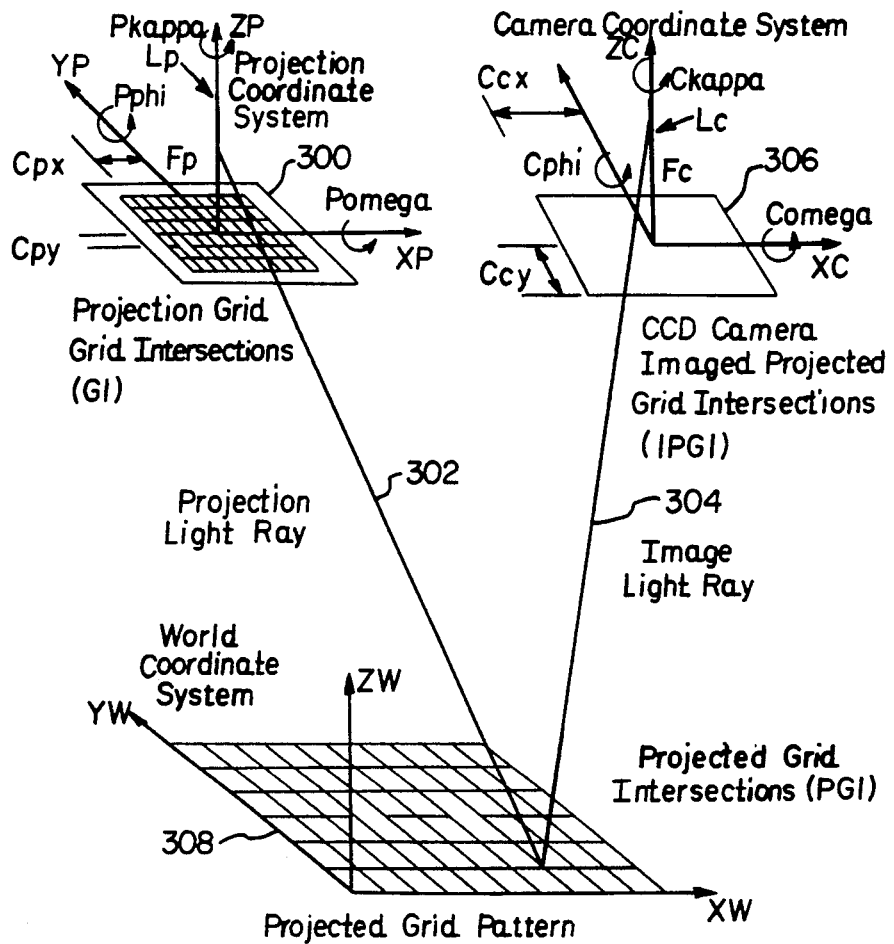
FIG. 16 illustrates in schematic form an analytical model of the second embodiment of the present invention.
Figure 17:
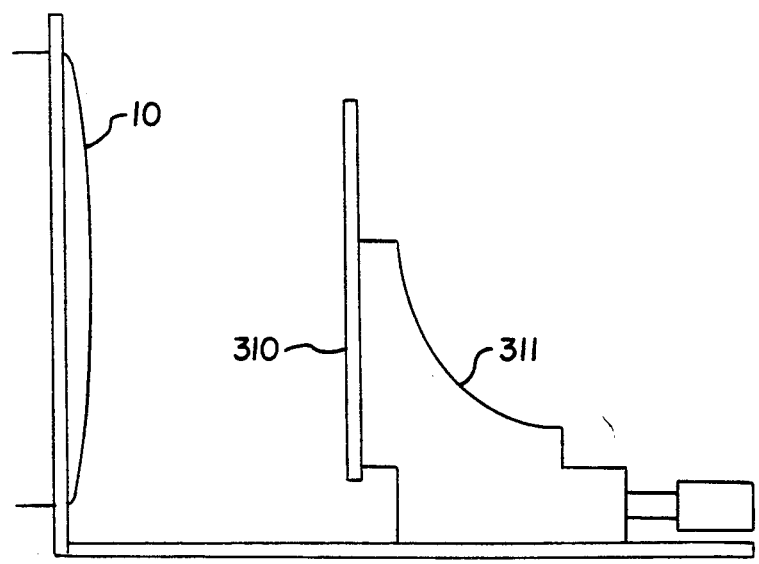
FIG. 17 illustrates a schematic elevational view of a calibration plate for particular use in the second embodiment.

FIGS. 15 and 17 are components involved in the operation of this embodiment and FIG. 16 is an analytical model of this second preferred embodiment of the invention.

The associated flow charts for the software and method for determining the topography of a cornea for this second embodiment are shown in FIGS. 18 to 36. The apparatus 10 of FIG. 3 is preferably used with this second embodiment.

The flash unit 34 or projection system for this second embodiment is shown in FIG. 15 with the projection grid 300, a projection grid holder 301, and a filter holder 303. A structured light pattern from grid 300 of FIGS. 14 and 15 is projected by projection system of FIGS. 3 and 15 onto the cornea 16 of FIG. 3, and an overlaying light pattern and the cornea 16 are imaged by video camera 32 of FIG. 3. This structured light pattern which appears on the surface of the cornea 16 provide the actual points to be analyzed by the image processing unit 44 in FIG. 3.

The flow charts for analyzing these actual points are shown in FIGS. 18-36, and a representation thereof is shown in FIG. 16. Referring particularly to FIG. 16, the method of this embodiment involves determining the intrinsic and extrinsic orientation parameters of the projection system and the position of the projected feature in the projection system, and using these factors to calculate a light ray 302 produced by the projection system and to intersect this projection light ray 302 with an image light ray 304 to determine the position of the projected feature on the cornea 16.

With reference to FIGS. 2, 3, and 14 when any type of lines, such as the vertical lines of FIG. 2 or the intersecting lines of FIG. 14 are projected onto the cornea 16, they tend to be distorted by the surface of the cornea and by the optics of the projection system 34 and camera system 32 of FIG. 3. As a result, in some instances it may be preferable to use the grid 300 of FIG. 14 for obtaining a more accurate representation of the topography of a cornea. This type of grid with intersecting horizontal and vertical lines exhibits details on the cornea in two dimensions so that the distorted positions of the lines can be detected in a two dimensional x-y plane.

As stated hereinbefore, in using this embodiment of the invention, grid 300 of FIG. 14 is projected by the projection system 34 of FIG. 16 onto the cornea and, as illustrated in an analytical model of FIG. 16, an image of the projected grid pattern indicated at 308 is captured by the camera system 32 (FIG. 3) as indicated at 306 and analyzed automatically through the use of the image processing techniques of processor unit 44, shown only in FIG. 3.

In referring particularly to FIG. 16 and in analyzing the grid 300, the points of interest in the grid pattern are the intersections of the vertical and horizontal lines and are generally referred to in FIG. 16 as grid intersections (GI). The grid intersections formed on the cornea by the projection system 34 of FIG. 3 in the projected grid pattern 308 are referred to as projected grid intersections (PGI), and the grid intersections on the imaged projected grid pattern 306 are referred to as imaged projected grid intersections (IPGIs).

The process of this embodiment involves the detection of the locations for each of the points of the projected grid intersections (GI) and the imaged projected grid intersections (IPGI) to determine the projected grid intersections (PGI) formed on the cornea. This procedure involves, therefore, the process of projecting the grid pattern; capturing the image of the projected pattern; detecting the IPGI points and computing their associated GI points. This data coupled with the calibrated intrinsic and extrinsic orientation parameters of the camera system and the projection system, as discussed hereinbefore, are used to construct a model for determining the contour of the cornea. The cornea is covered with a coating such as a fluorescein solution for creating an opaque non-transparent, light diffusing surface, resulting in the projected grid pattern being imaged on the surface of the cornea.

Still referring particularly to FIG. 16, an approach in the above procedure is to find as many of the IPGI points in the image as possible. Once these IPGI points are detected, their location relative to a known reference GI point is calculated. This latter step is accomplished by noting the proximity of the IPGI points to a known reference GI point. Each detected IPGI point then has associated with it a location in the image or in the camera system represented by the imaged grid pattern of numeral 306 and a location in the projection system represented by the grid pattern of the grid indicated by 300 in FIG. 16.

Referring to FIG. 14, the projection grid 300 may measure approximately 26.6 millimeters in width and 26.6 millimeters in length. The line width is approximately 0.017 millimeters, and the line center spacing is approximately 0.20 millimeters. The line spacing is chosen to allow the optimum detection of the grid intersection in the image (IPGI). The line spacing is large enough so as to be detected by the imaging system, and to provide sufficient coverage of the area of the cornea being measured.

The detected imaged projected grid intersections (IPGI) are referenced back to the actual grid intersection in the projection grid of FIG. 14, more about which will be discussed hereinafter. The two vertical bars shown at reference numerals 305 and 307 are used as reference bars to refer the detected IPGIs back to the actual IPGIs of the grid of FIG. 14. The length of bars 305, 307 is approximately 0.8 mm, and the distance from bar 305 to bar 307 is approximately 4.8 mm when considered from the outer ends of bars 305 and 307. Each detected IPGI's position is determined relative to the imaged reference bar 305, 307 located to the left of that detected IPGI. This is performed during the detection of the IPGIs. This relative position of the detected IPGIs simultaneously determines the position of the actual IPGI relative to the actual reference bar in the projection grid 300 of FIG. 14.

The location of each IPGI point is in terms of pixels in the computer frame buffer. The location of the GI point is in terms of rows and columns and is relative to a known reference GI point. The position of each of these GI and IPGI points is considered in terms of a Cartesian coordinate system. The first step is to convert the coordinates for the GI and IPGI into millimeters, and the second step is to convert these GI points into a projection coordinate system and the IPGI points into a camera coordinate system as legended in FIG. 16.

This conversion procedure is outlined in the flow chart of FIG. 33, particularly in steps 668 and 672, more about which will be discussed hereinafter. At this time, the GI and IPGI points are known in the projection and camera coordinate systems. The intrinsic and extrinsic parameters for the orientation of these components in space were previously calibrated. The above obtained data for the GI and IPGI points are used to compute the positions of the PGI points in the world coordinate system indicated at 308 in FIG. 16.

Still referring to FIG. 16, the camera coordinate system 306 has axes labeled XC; YC; and ZC. This coordinate system is defined by the location and orientation of the camera system 32 of FIG. 3. The projection coordinate system indicated at 300 has axes labeled XP; YP; and ZP. This coordinate system is defined by the location and orientation of the projection system grid 300 and the projection system 34 of FIGS. 3 and 15. The world coordinate system indicated at 308 in FIG. 16 has axes labeled XW, YW, ZW, which coordinate system is defined by the position of a calibration plate 310 of FIG. 17 during the calibration process. This calibration plate 310, of FIG. 17 is slideable.

Preferably, calibration plate 310 of FIG. 17 is made up of a 2 inch square, ⅛th inch thick piece of white ceramic. A pattern is deposited on one side of the plate by a photographic evaporation process. The pattern is the same as that of the projection grid 300 of FIG. 14. By using the same pattern as the projection grid 300, the same software that is used to find the projected grid intersections can be used to find the grid intersections on the calibration plate 310. This plate 310 is mounted on a linear translation stage 311 which is attached to the front of a slit-lamp or an operating microscope shown in FIG. 17 at numeral 10. This translation stage 311 allows accurate positioning of the plate 310 about the slit-lamp or operating microscope 10.

In reference to FIG. 16, the intrinsic parameters for the camera system 32 of FIG. 3 are 1) the principal point indicated in FIG. 16 as Ccx, Ccy; 2) the effective focal length indicated as Fc in FIG. 16; 3) the camera lens radial distortion coefficients represented in the software as Kc1, Kc2, and Kc3; and 4) the camera lens tangential distortion coefficients represented in the software as Pc1, Pc2.

In still referring to FIG. 16, the intrinsic parameters for the projection system 34 of FIG. 3 are 1) the principal point indicated in FIG. 16 as Cpx, Cpy; 2) the effective focal length indicated by Fp in FIG. 16; 3) the projection lens radial distortion coefficients represented in the software by Kp1 Kp2, Kp3; and 4) the projection lens tangential distortion coefficients represented in the software as Pp1, Pp2. The distortion coefficients are not shown in the figures, particularly FIG. 16, since they represent coefficients of a mathematical equation which describes the distortion in a lens of a microscope, i.e. they do not represent discrete measurements.

The extrinsic parameters of the camera system 32 are labeled as Lc which indicate the perspective center (Xc, Yc, Zc) for the camera system; and C omega, C phi, and C kappa which indicate the angles of orientation for the camera system 32. For the projection system 34, the extrinsic parameters are indicated as Lp, representing the perspective center (Xp, Yp, Zp); and P omega, P phi, and P kappa, representing the angles of orientation for the projection system 34.

In FIG. 16, the points Lp and Lc define the location of the camera and projection systems relative to the world coordinate system 308. The light rays 302, 304 (FIG. 16) which are intersected to determine surface positions emanate from these two positions Lp and Lc.

The intrinsic and extrinsic parameters are determined through a calibration procedure which is illustrated in the flow charts of FIGS. 18 to 22. Once these parameters are determined, the GI and IPGI points are located, and the intersection points for the projection light ray 302, and the image light ray 304, through a triangulation procedure, (which is to be discussed hereinafter) are determined. These intersection points of light rays 302 and 304 represent the PGI points of 308 in the world coordinate system in FIG. 16.

Since the shape of a specific cornea is not known and will vary from patient to patient, several PGI points are obtained. These points will be distributed irregularly over the surface of the cornea resulting in a varying density of data points across the cornea. This therefore requires the conversion of this irregular format to a workable or meaningful format. This transformation of irregular surface corneal data to a workable cornea data involves interpolation of the elevation (in terms of the Z coordinate values) for evenly spaced X-Y coordinate points. The software or subroutine as a representation of the results of this software of the main computer program of the invention for this procedure is shown in FIGS. 23 to 36.

The interpolation scheme selected depends on the shape of the surface in the immediate vicinity of the PGI (FIG. 16) point which is to be interpolated. If the shape of the surface of the local area is determined to be flat, a bilinear interpolation is used utilizing the information provided by the four surrounding PGI data points. If the shape of the surface of the local area is determined to be other than flat, an analytical function such as a "least squares approach" can be used utilizing a small number of subset surrounding PGI data points. The derived interpolated value can then be calculated by solving this fitting equation for a predetermined number of evenly spaced X-Y coordinate values.

In the case of the present invention, especially this second embodiment, the shape of the surface of an area of the cornea being examined is assumed to resemble that of a normal cornea. The "new" data point is calculated by the interpolation scheme which assumes this normal curvature shape. The final data output consists of a set of evenly spaced elevation coordinate or the Z coordinate of the world coordinate system (Reference No. 308 of FIG. 16); the X-Y coordinates for the Z-coordinate for the world coordinate system; and only the X-Y coordinates of the first point in the elevation matrix. The spacing values and the first point value in the world coordinate system allow easy calculation of any Z-coordinate for any X-Y coordinates in the world coordinate system of reference number 308 of FIG. 16, more of which will be further discussed.

A further discussion of the flow charts of FIGS. 18 to 36 will now be given. The grid 300 with intersecting vertical and horizontal lines similar to that of FIG. 14 is projected onto the cornea. Before any measurements of the cornea can be performed, the system is subjected to a calibration procedure to provide accurate values for the intrinsic and extrinsic parameters for the orientation in space of the projection and camera systems 34, 32 respectively as discussed hereinbefore.

Figure 18:
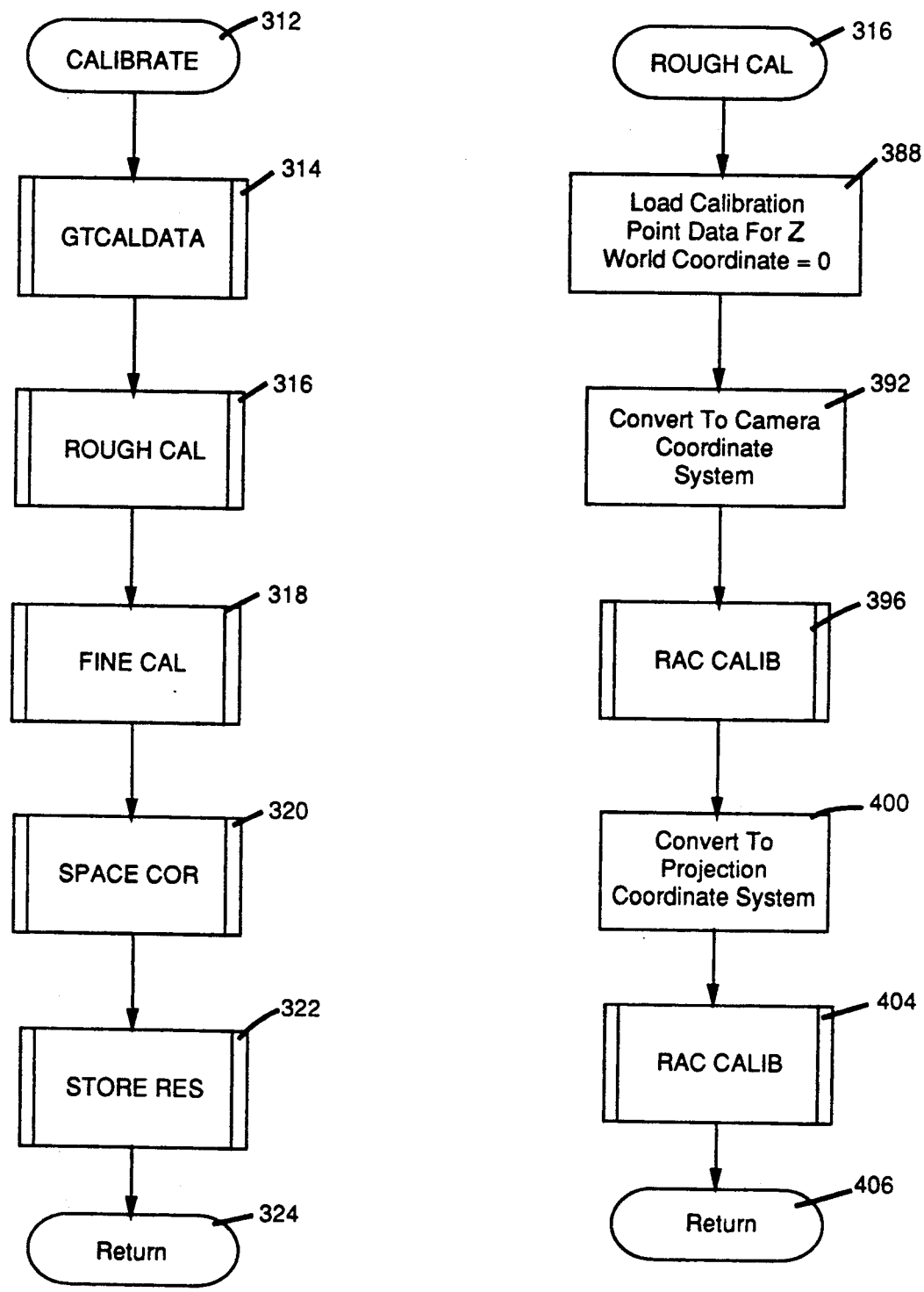

The calibration procedure of FIG. 18 uses calibration control points, which are points having known world coordinate values and observed grid and camera coordinate values.

In FIGS. 18 to 36, the arrows indicate the direction of flow for the information within the computer.

In referring to the flow chart of FIG. 18, the calibration function or procedure is indicated by reference number 312. For the calibration procedure the first step is to gather the calibration data needed to calibrate the system as indicated by GT CALDATA at reference number 314. A rough calibration of the system is performed as indicated by ROUGH CAL and reference number 316. This rough calibration is done by utilizing the RAC technique, more about which is discussed hereinafter. A fine calibration of the system is performed by using a Bundle Model Adjustment Technique as indicated by FINE CAL and reference number 318. A final calibration accounting for systematic error is performed by subroutine SPACE COR as indicated by reference number 320. This involves computing the parameters of a space correction polynomial. The calibration information is stored in STORE RES as indicated by reference number 322. This subroutine archives the calibration results for later retrieval during the feature measurement of the cornea. Once the steps indicated by reference number 322 is performed, the subprogram of FIG. 18 returns to the main program as indicated by the return symbol 324.

Still referring to FIG. 18, the step entitled "GTCALDATA," at reference number 314, represents the step of gathering the calibration data needed to calibrate the system basically. This data consists of information for an array of calibration points. The information for each point consists of X,Y,Z coordinates for the intersection points of the projection grid 300 (GI); the imaged projected grid 306 (IPGI), and the projected grid 308 (PGI). As mentioned hereinbefore, this information is obtained and constructed from images of selected known surfaces which were calibrated previously. The shape of the cornea being examined can be assumed to resemble the shape of a normal cornea. In this case, the cornea is considered to have a known shape and an accurate equation can be chosen to represent the surface of the examined cornea and the data points can be fitted to the equation using a standard least square approach. If the shape of the cornea is not known in advance, the data for an irregular surface can be transformed into data for a regular surface by interpolating the Z-coordinate values for evenly spaced X-Y coordinate pairs. The above calibration procedure is preferably performed using standard photogrammatic methods known to those skilled in the art.

Figure 19:
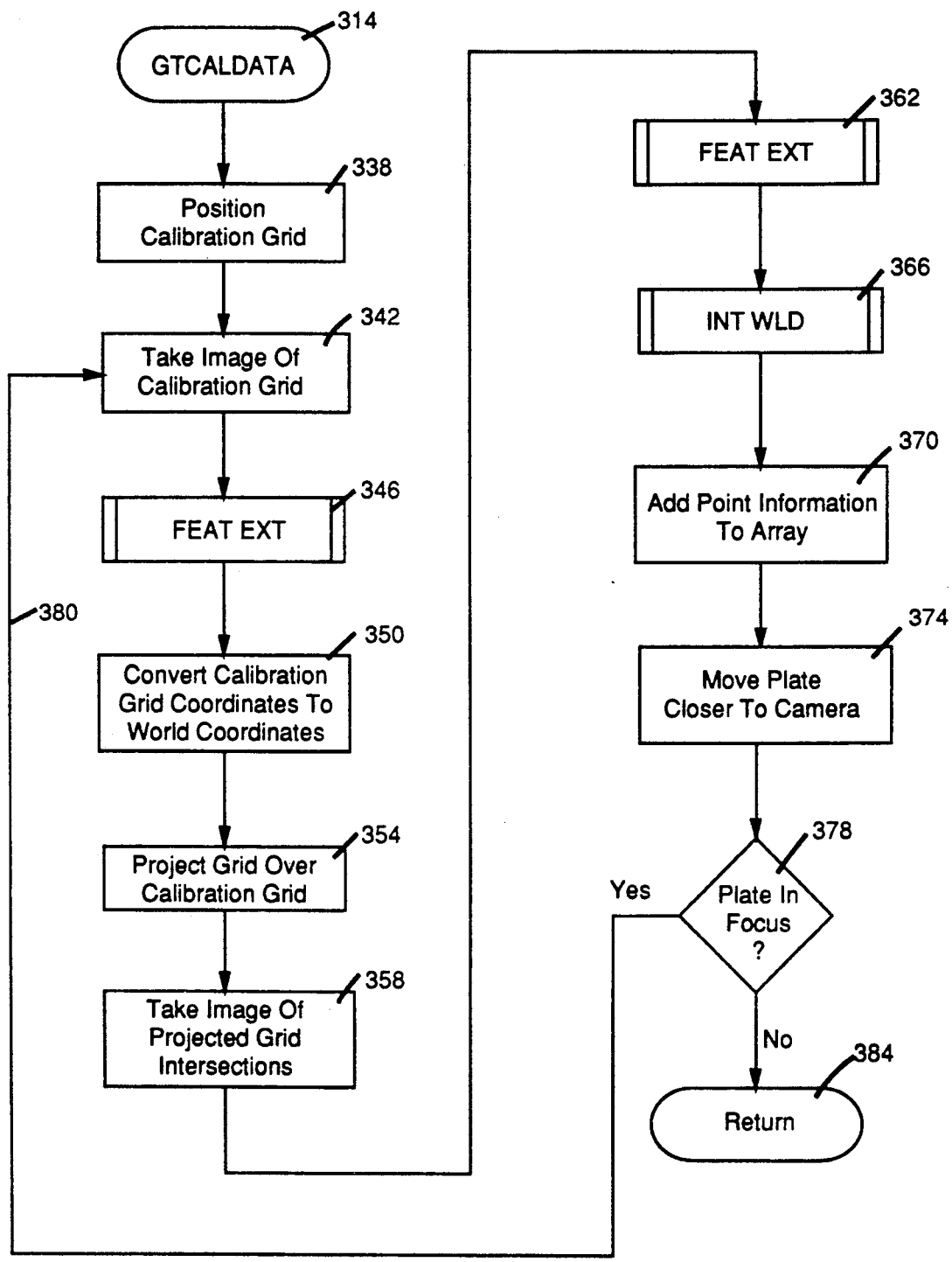

FIG. 19 illustrates the subroutine for gathering the calibration data of step 314 in FIG. 18. The first step as indicated at reference number 338 is to position the calibration plate 310 of FIG. 17 as far as possible away from the objective lens system 12 of the microscope 10 of FIG. 3, while still maintaining the calibration plate 310 in focus. This calibration plate 310 should be positioned such that the reference lines in the grid appear in a vertical direction and substantially symmetrical about the center of the image.

The next step is indicated by reference number 342 which indicates that the image of the calibration plate 310 is to be taken. This image is captured with the projection system 34 being inoperative so that only the imprinted pattern of the calibration plate appears in the image. This captured image is retained in the frame buffer for subsequent processing.

The imaged calibration grid intersections are extracted from the image represented at step 342 by using a feature extraction routine as indicated by FEAT EXT at reference number 346. This subroutine at 346 determines the camera and grid coordinates of the imaged calibration grid intersections. This routine can be used since the calibration grid pattern is constructed similar to the projected grid pattern 308 of FIG. 14. The obtained data consists of camera coordinates for all the detected imaged intersections of the calibration grid and the grid coordinates of corresponding calibration grid intersections.

The next step in FIG. 19 is to convert the calibration grid coordinates to world coordinates indicated at 350. The X-Y world coordinates are computed by multiplying each calibration grid coordinate by the spacing between the calibration grid intersections. This value is specified during manufacturing of the calibration grid. The Z coordinate value of an X-Y pair is assigned a value which is equal to the distance that the calibration grid had been moved away from the optical lens system 12 of device 10 since the calibration data gathering procedure began.

Once the step at 350 in FIG. 19 is performed, the actual grid being used in the examination process is superimposed over the calibration grid as by reference number 354 in FIG. 19. The projection system 34 of FIG. 15 is turned on and operated to perform this step at 354. The calibration grid is coated with a fluorescent material to simulate the fluorescent effect produced by the cornea during examination. The resulting pattern is the projected grid intersections (PGI) of the world coordinate system 308 of FIG. 14. It is important that this step at 354 be performed with the calibration grid in a fixed position. The next step at 358 involves turning on the projection system 34 of FIG. 15 and taking a flash illuminated image of the projected grid intersections (PGI) on the surface of the calibration grid.

Reference number 362 indicates a FEAT EXT subroutine. This routine determines the camera and grid coordinates of the imaged projected grid intersections (IPGI) The camera coordinates of the detected imaged calibration grid intersections are determined in step 346, and this information in step 346 together with the information from step 362 is used in step 366, more about which is discussed hereinafter.

The next routine is indicated by reference number 366 entitled "INT WLD". This routine interpolates the coordinates of the projected grid 300 on the calibration plate 310. This routine calculates the X-Y world coordinates (308) for the projected grid intersections (PGI). This is performed by solving an eight parameter affine transformation using as input the X-Y world coordinates of the closest four surrounding calibration grid intersections and the associated camera coordinates of the imaged calibration grid intersections. The affine transformation solution is then used to compute the X-Y world coordinates of the projected grid intersection (PGI) using as input the camera coordinate of the imaged projected grid intersection (IPGI) of FIG. 16.

The Z-coordinate of the world system of the PGI is determined by the position of the calibration grid 310 of FIG. 17 when the image of the PGIs was taken. The final output consists of a camera coordinate set of each imaged PGI, the world coordinate set of the PGI, and the grid coordinate set of the grid intersection (GI) used in forming the projected grid intersection (PGI).

As reference number 370 indicates, the next step is to add the point information found in the previous step to an array. This process adds the calibration control point which was just calculated to a file for use in the calibration procedure.

In the next step of reference number 374, the calibration plate 310 of FIG. 17 is manually moved by operator approximately 0.5 millimeters closer to the objective lens system 12 of device 10. In particularly referring to FIG. 17, calibration plate 310 is slidable toward and away from the objective lens (only shown in FIG. 3). This movement of plate 310 which has the intersecting horizontal and vertical lines as that of the grid 300 FIG. 15 is done to allow for the extraction of calibration data at different elevations on Z coordinates for the world coordinate system 308 of FIG. 16.

The new calibration grid position is used as the Z coordinate value of the world coordinate system 308 of FIG. 16 for all projected grid intersections (PGI) detected in the next image of the projected grid intersections PGI in the world coordinate system.

The next step of FIG. 19 as indicated at reference number 378 asks the operator whether plate 310 of FIG. 17 is still in focus. If the answer is "yes," then the routine returns to step 342 as indicated by reference number 380. This complete procedure is repeated until the calibration plate 310 of FIG. 17 is no longer in focus. This is done in view of the need to acquire calibration point data which completely covers the field of view and the depth of field of the optical system 12 for its current magnification setting. If "no", the routine returns to the sub-program of FIG. 18 as indicated by return step 384. Still referring to FIG. 18, after gathering the data the next step as indicated by reference number 316 in FIG. 18 is to make a rough calibration of the intrinsic and extrinsic parameters of the entire system.

The steps for this routine 316 entitled ROUGH CAL are further shown in FIG. 20. This calibration routine 316 uses a technique referred to as the Radial Alignment Constraint technique (RAC), which is well-known in the art. This method uses a subset of all the calibration control points in order to determine a rough approximation of the intrinsic and extrinsic parameters. Assumptions about the optical system are made in order to provide a fast approximate solution to the calibration problem.

The first step indicated at 388 of this ROUGH CAL routine 316 of FIG. 20 is to load all the calibration point data for which the Z coordinate of the world system equals zero. The next step indicated at reference number 392 is to convert the results of the preceding step to the camera coordinate system 306 (FIG. 16). This procedure of step 392 converts the pixel coordinates of the imaged projected grid intersections (IPGI) onto the camera coordinates. The pixel coordinates are first multiplied by the pixel scale factor. The X-dimensional scale factor is equal to the horizontal CCD dimension divided by the number of horizontal CCD elements (FIG. 16). The Y-dimensional scale factor equals the vertical CCD dimension divided by the number of vertical pixels in the frame buffer. CCD stands for charge-coupled device, and is a standard type of video camera.

In view of the variation in video scanning rates between the CCD and a frame grabber, the X-dimensional scale factor is also multiplied by the ratio of the horizontal CCD scan frequency to the horizontal frame grabber scan frequency. These scan frequencies are obtained by connecting a conventional frequency counter to the clocks of the CCD and the frame buffer.

As is known in the art, a frame grabber is the computer hardware responsible for capturing a video image from the CCD video camera, digitizing it, and storing it in the computer memory. This digitized image is the data the image processing software works on. The frame grabber used in the invention may be an off-the-shelf item with features similar to the several kinds of frame grabbers.

The scanning rate refers to the rate at which the camera or the frame grabber grabs the image. The higher the resolution of the system, the higher the scan rate. Since the camera and the frame grabber do not have the exact same resolution their scan rates are different. This difference in scan rate can produce a systematic error if not compensated for.

After the X and Y pixel dimensions are converted to millimeter coordinates by their respective scale factors, they are converted to the camera coordinates by subtracting the principal point coordinates (Ccx, Ccy) of the camera system (FIG. 16).

The next step of this ROUGH CAL calibration procedure is indicated by reference number 396 entitled RAC CALIB. This calibration procedure refers to the Radial Alignment Constraint (RAC) technique and is performed on the camera subsystem. This method uses a simplified model to represent the camera system 32 and projection system 34 in order to quickly determine rough approximations for the extrinsic and intrinsic parameters of the camera system 32. The input to this step 396 consists of the camera 32 and the world coordinates 308 of the imaged projected grid intersections 306 shown in FIG. 16. The output consists of the focal length Fc of the camera, the position of the camera (Lc) and the orientation angles $C_{omega}$, $C_{Phi}$, and $C_{kappa}$ of the camera (FIG. 16). These values are then refined in the FINE CAL routine 318 of FIG. 21.

The next step of the 316 routine of FIG. 20 is indicated at reference number 400 which is to convert the grid coordinates of the detected imaged projected grid intersections (IPGI) of FIG. 16 into the coordinate system of projection system 34. The X-Y coordinates are multiplied by the grid scale factor in millimeters which is determined by the design of the grid being used during examination as exemplified in FIG. 14.

These coordinates in millimeters are converted to the projection coordinate system 300 of FIG. 16 by subtracting the principal point coordinates Cpx, Cpy of the projection grid. The final step of the subroutine "ROUGH CAL" is indicated by RAC CALIB and performs the RAC calibration procedure to find rough approximations for the parameters of the projection system. This is illustrated at reference number 404 of FIG. 20. This routine uses the grid and world coordinates of the projected grid intersections (PGI) as input, and produces the focal length Fp of the projection system, and the orientation angle $P_{omega}$, $P_{hi}$ and $P_{kappa}$ (FIG. 16), of the projection system. Refinements of these parameters are performed in the fine calibration (FINE CAL) routine 318 of FIG. 21, upon the return step 406 of FIG. 20 to the flow chart FIG. 18.

Figure 21:
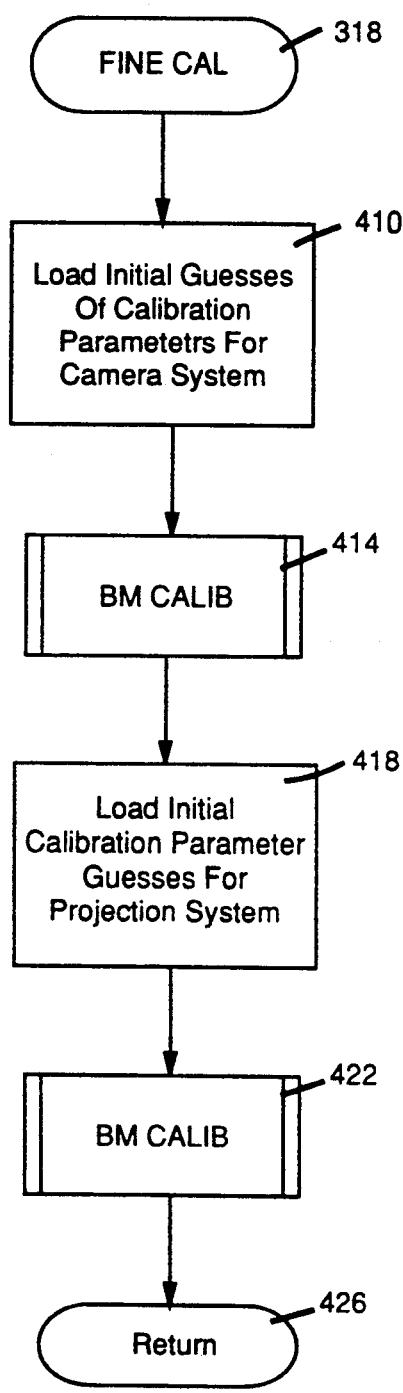

Referring to FIG. 21, the FINE CAL routine 318 performs steps indicated at reference numbers 410, 414, 418, 422 and 426. Step 410 loads the initial approximations of the calibration parameters for the camera system. Step 414 is a BM CALIB subroutine which performs the Bundle Model Adjustment calibration for the camera subsystem. Step 418 loads the initial guesses for the calibration parameters for the projection system. The BM CALIB subroutine 422 performs the Bundle Model Adjustment calibration for the projection subsystem. Reference numbers 410 and 418, respectively, indicate that initial approximations for the calibration parameters for the camera system and the projection system are loaded into the computer system in the sequence as illustrated. The equations used in step 410 are as follows:

X0, Y0 = Ccx, Ccy (frame buffer center)
C = Fc
$X_c, Y_c, Z_c$ = Lc
Omega, Phi, Kappa = C omega, C Phi, C Kappa $K_1, K_2, K_3 = 0$
$P_1, P_2 = 0$ The equations used in Step 418 are as follows:
X0, Y0 = Cpx, Cpy (Center of projection grid)
C = Fp
$X_c, Y_c, Z_c$ = Lp
Omega, Phi, Kappa = P omega, P Phi, P Kappa $K_1, K_2, K_3 = 0$
$P_1, P_2 = 0$ These approximations which appear on the left of the above equations are set equal to the parameters for the camera and projection systems which appear on the right of these equations. The symbols to the right of the equal sign are defined hereinbefore. Following the initial approximations step is a step which performs the refinements of the calibration parameters for the camera and projection systems using a successive approximation technique. As stated hereinbefore, this technique is referred to as the "Bundle Model Adjustment" (BMA) and is a standard camera calibration technique well known to those skilled in the art and disclosed in many photogrammetry textbooks.

When choosing the "initial approximations" to be solved in the solution, parameters which have a strong correlation to one another are avoided in that a unique solution may not be obtained. The uniqueness of the calibrations lies in the choice of parameters which are solved in the algorithm and the limits or controls placed on the selected parameters as they change during this adjustment stage.

Preferably, the center point XO, YO of both the camera coordinate system and the grid coordinate system of the hereinabove equations are held relatively constant in this adjustment period. The input to the BM CALIB routine of step 414 of FIG. 21 consists of the camera and world coordinates for the control points found in the preceding calibration procedure of step 396 of FIG. 20, and the input to the BM CALIB routine of step 422 of FIG. 21 consists of the grid and world coordinates of the control points found in the preceding calibration procedure of step 404 of FIG. 20.

The Bundle Model Adjustment (BMA) technique of routine 422 continues to adjust the parameters for the camera and projection systems until the resulting model predicts the world coordinates of the control points to be within an average error of less than .005 millimeters. As indicated at reference number 426, completion of this routine returns this routine program to the program of FIG. 15.

Figure 22:
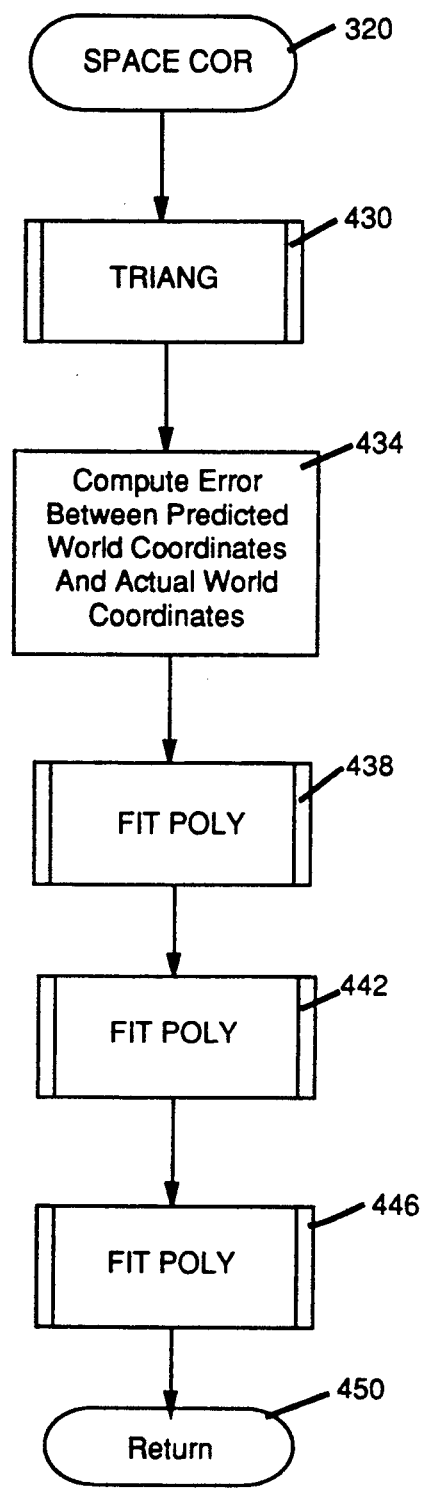

The next routine is SPACE COR indicated at reference number 320 in FIGS. 18 and 22. This routine 320 computes the parameters for a space correction polynomial, and performs a final calibration step accounting for any systemmatic errors which were not accounted for by the rough and fine calibration procedures. In the second embodiment of this invention, the polynomial is a second order general polynomial with three variables (X, Y, Z) for a total of nine third order terms. The terms are: $x^3, y^3, z^3, x^3y, x^3z, y^3x, y^3z, z^3x$, and $z^{3y}$, making a complete equation of thirtysix (36) terms, referred to as a thirty-six term third order polynomial.

The first subroutine 430 in FIG. 22 is called TRIANG, and involves the computation of predicted world coordinates of the calibration point data using a stereo-triangulation method. Stereo-triangulation is a photogrammetric procedure well-known to those skilled in the art, and discussed in many photogrammetric textbooks. This step 430 uses as input the camera and grid coordinate system and the refined calibration information for the camera and projection systems obtained in the FINE CAL routine 318 of FIG. 21.

In this step 430 the projected grid intersections (PGI) of the world coordinate system 308 of FIG. 16 are used as the calibration control points. The output is the calculated world coordinates of the calibration control points. Step 434 of FIG. 22 computes the error existing between the predicted world coordinates and the actual world coordinates. The world coordinates of the calibration control points are determined in the TRIANG routine 430 of FIG. 22 and the actual world coordinates are obtained in the GTCALDATA routine 314 of FIG. 19. This difference is computed for each X, Y, Z dimension. This difference represents both the systematic and the random errors present in the system.

The next three subroutines are FIT POLY routines indicated by reference numbers 438, 442, and 446.

Referring particularly to the FIT POLY of reference number 438 in FIG. 22, this routine 438 fits the thirty-six (36) term second degree polynomial to the x-dimension of the results obtained in step 434 by determining the coefficients using a least square approach. The solution provides a mathematical model which represents the systematic error left in the system after the FINE CAL routine 318 of FIG. 21. This information is used to correct for this systematic error during the topographical measurement of the cornea. The input to this routine 438 consists of the calculated X-dimension and the known X-dimension of the world coordinates for all the calibration control points. The output consists of thirty-six floating point polynomial coefficients which is used to correct for the error in the calculation of the X-dimension in the world coordinate system of the cornea.

The hereinabove discussion referring in particular to FIGS. 18 to 22 explains the process for calibrating the system for a predetermined microscope and magnification setting.

The FIT POLY routines 442 and 446 of FIG. 22 operate in a manner similar to that of the FIT POLY routine 438 to correct for errors in the Y and Z dimensions for the world coordinate system. That is, the subroutine 442 fits a thirty-six parameter polynomial to errors for predicting the Y-world coordinate, and subroutine 446 fits a thirty-six parameter polynomial to errors for predicting the Z-world coordinate. Step 450 of FIG. 22 indicates a return to the calibration routine 312 of FIG. 18.

As indicated by reference number 322 of FIG. 18 the next step in the main calibration routine is STORE RES which stores the calibration information. This information is stored under a code indicating the microscope and its magnification settings used in the calibration procedure. This information is later retrieved automatically by the computer system when the operator of the system tells the system that this particular microscope and its magnification setting is in use.

Reference number 324 of FIG. 18 indicates a return to the main computer program (not shown).

FIGS. 23 through 36 disclose the actual measurement procedure for the cornea under examination.

Figure 23:
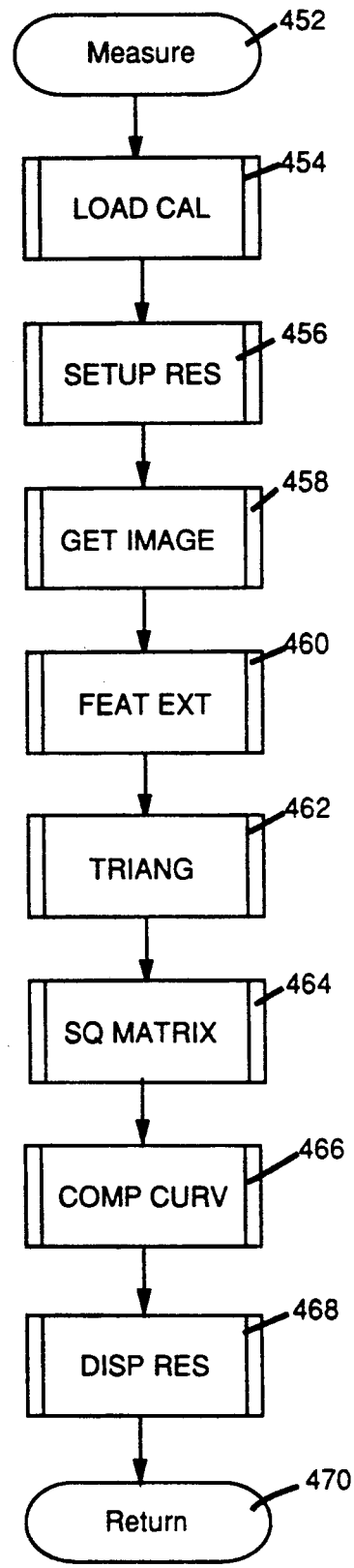
FIGS. 23-25 27, 29, 31, and 33-35 illustrate logic flow diagrams for a measurement procedure for the second embodiment.

FIG. 23 illustrates a sub-program 452 for the measurement procedure which is part of the main program (not shown). In FIG. 23, the LOAD CAL subroutine 454 loads all the calibration information previously stored for the particular microscope and its magnification setting in use.

The SETUP RES routine 456 in FIG. 23 sets up the system resources which are needed. This routine allocates and initializes the resources of the computer system needed to perform the measurement procedure.

The GET IMAGE subroutine 458 captures a cornea image with a projected grid pattern, or displays a previously captured image and allows the operator to obtain an image of the cornea with a superimposed grid pattern projected thereon. The image is captured with the flash exposure of the projection system 34 and is digitized by the computer frame grabber into the frame grabber memory. The image can be saved on a hard, floppy, or optical disk for retrieval at a later time. This routine 458 also allows the operator to retrieve previously stored images.

The FEAT EXT routine 460 determines the camera grid coordinates of the imaged projected grid intersections. This routine performs the image processing which detects the projected grid intersections (PGI) in the image. This routine 460 produces an output consisting of the grid coordinates (GI) and the camera coordinate of each detected imaged projection grid intersection (IPGI).

This FEAT EXT routine 460 is further discussed with reference to FIGS. 24 to 33, and consists of several subroutines indicated at reference numbers 472, 474, 476, 478 and 480, shown in these FIGS. 24 to 33.

This FEAT EXT routine 460 in FIG. 23 stands for "feature extraction algorithm," and is discussed more fully hereinafter.

A similar "FEAT EXT" algorithm is used in the calibration procedure of steps 346 and 362 of FIG. 19 to determine the camera and grid coordinates of the imaged calibration grid intersections. The FEAT EXT routine can be used in the GTCALDATA routine because the pattern on the calibration plate is made to resemble the grid pattern projected onto a flat surface. The only changes to the original FEAT EXT routine are the control parameters given to the routine.

In still referring to FIG. 23, the next routine after routine 460 is the TRIANG routine 462. A triangulation procedure is performed on the detected grid intersection data in order to compute world coordinates of projected grid intersections. The routine at 464 entitled SQ MATRIX produces a uniformly spaced square matrix of elevations.

The subroutine at 466 entitled COMP CURV computes the curvature across the meridian by fitting curves to the elevation data. The routine at reference number 468 entitled DISP RES displays the results on a graphic monitor, and the return step at reference number 470 returns the program to the main program.

Figure 24:
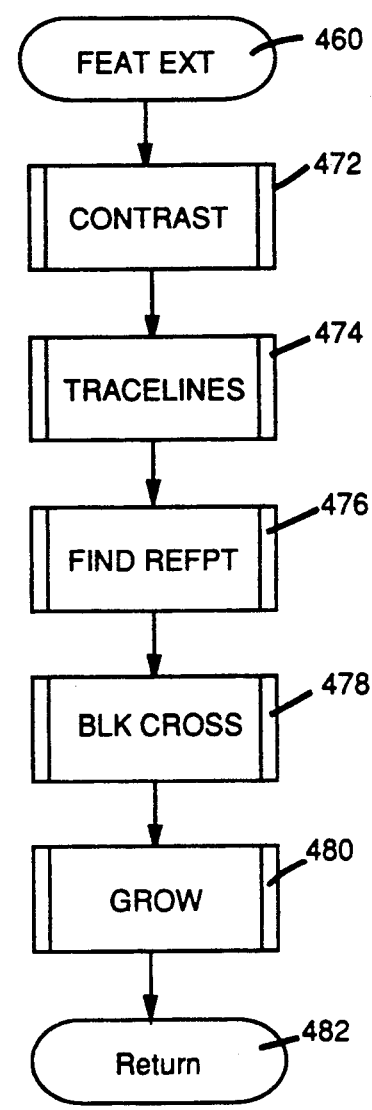

The FEAT EXT routine 460 of FIG. 23 is further detailed in FIG. 24. It consists of subroutines 472-480. The CONTRAST subroutine 472 finds the central areas of white squares in each image line. The TRACELINES routine 474 finds the center pixel of the white squares. The FIND REFPT routine 476 finalizes the search for one of the two reference lines in the image. The BLK CROSS routine 478 determines the camera coordinates of the imaged projected grid intersections (IPGI). The GROW routine 480 links the imaged projected grid intersections (IPGI) to determine the corresponding grid intersections (GI). The return step at 482 returns this part of the program to the next step of the MEASURE routine of FIG. 23 (more of which is discussed hereinafter.)

Figure 25:
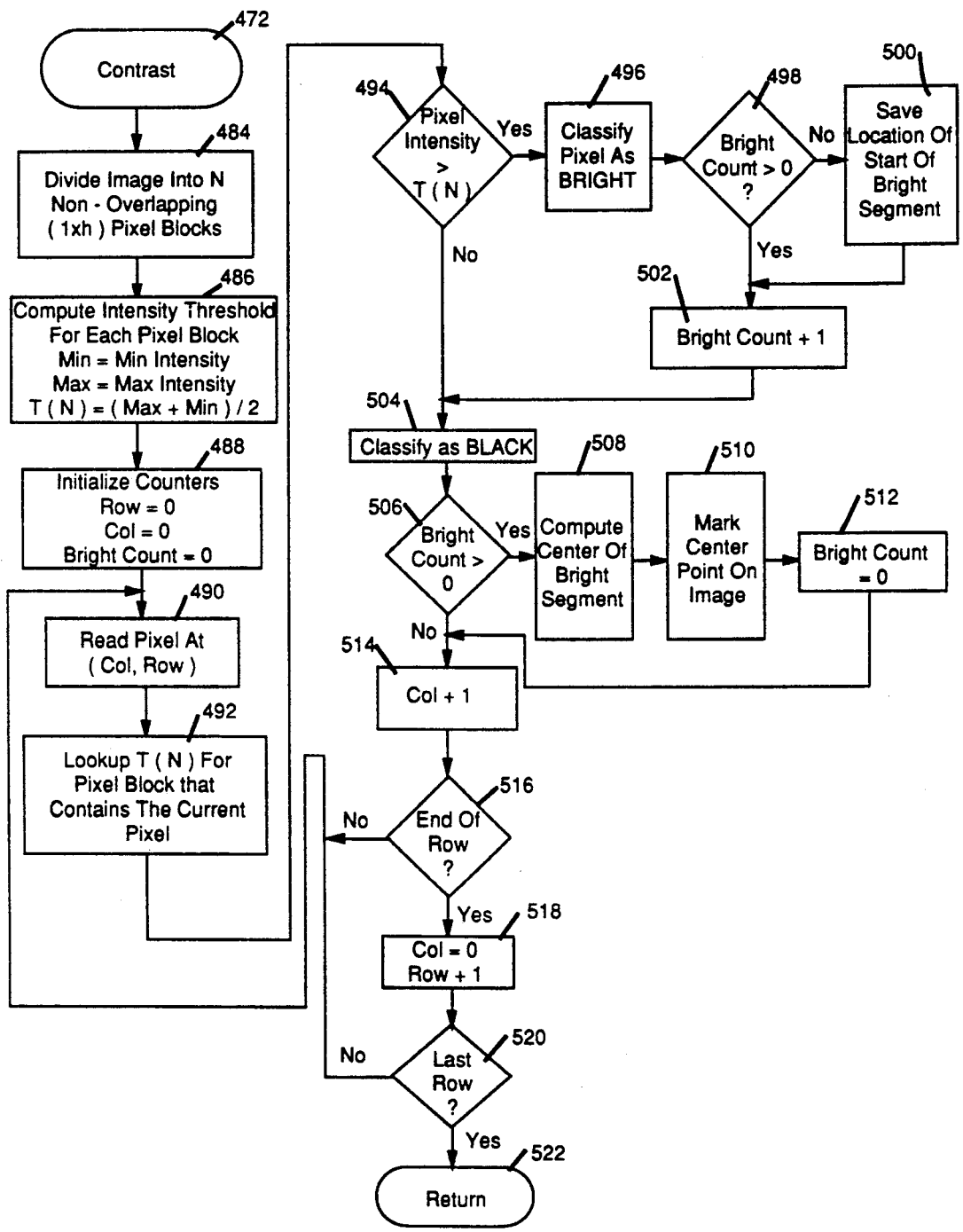

Referring in particular to FIGS. 24 and 25, the CONTRAST routine 472, which is the first subroutine of the FEAT EXT routine 460 searches each line of the image of the projected grid intersections for a pixel which is horizontally and centrally located in each of the white squares formed on the surface of the cornea. This is done by comparing the intensity of every pixel to a threshold calculated from a window of pixels located around the pixel in question. The flow chart for the CONTRAST routine 472 is illustrated in FIG. 25, and a graphical explanation of this step 472 is illustrated in FIG. 26, entitled title "CONTRAST ALGORITHM."

In reference to FIG. 26a, an idealized input image of a grid with horizontal and vertical intersections is shown at reference number 485, and a superimposed output image containing the data found in this CONTRAST subroutine 472 is shown at reference number 487. This output image 487 represents the vertical segments through the white squares.

As FIG. 25 indicates in step 484, each white block of input grid 485 of FIG. 26a is divided into N ($h \times 1$) number of non-overlapping square areas representing pixel blocks The letter "N" represents the regions and the letter "T" represents threshold. FIG. 26b shows a block divided into several smaller blocks, where the first block is labelled T1 and the last is labelled $T_n$. This represents the input image of 485 in FIG. 26a being divided into N ($h \times 1$) regions and T (threshold) computed for each region.

Referring again to FIG. 25, the next step in reference number 486 computes the intensity threshold or limit for each pixel block, where min=mininum intensity; max=maximum intensity; and $T(N)=(max+min)/2$. Each of these pixel blocks are identified as $T_l$ through $T_n$, and is shown in representation form at reference number 489 in FIG. 26b, as discussed hereinbefore.

The remaining steps indicated by reference numbers 488 through 520 essentially initialize the counter (reference number 488), reads the pixels by row and column (reference number 490), and determines the intensity of each pixel and characterizes the intensity as being bright (B) or dark (D) (reference numbers 492-516). These steps 488-520 also includes: computing of T values for a selected row in the window being analyzed; determining the greatest value for T in the selected row, which represents the center of the "bright" segment; and marking the center point for this bright segment as shown at reference number 510.

In Step 488, the counters for row, column, and bright count are initialized and given a zero value. This step 488 begins the loop starting from reference numbers 490 through 520. Step 490 reads the pixels by row and column (COL). Reference number 492 looks up T(N) for a pixel block that contains the current pixel. Step 494 asks whether the pixel intensity is greater than T(N). If the answer is "yes", then the program proceeds to the next step 496 which is indicated to the right in FIG. 25 where the pixel is classified as being "bright." Step 498 asks whether the bright count is greater than zero. If the answer is "no", the program proceeds to step 500 which instructs the location of the start of the bright segment to be saved. From step 500, the program proceeds to step 502. If the answer to the question in step 498 is "yes", then the program proceeds to step 502 where the "bright count" is incremented by 1.

This step 502 proceeds to step 504. If the question in step 494 is "no", then the program proceeds to step 504, thereby, eliminating steps 496 to 502.

The input in step 504 classifies the pixel as being "black." Step 506 asks if the bright count is greater than zero. If "yes", the program proceeds to step 508 where the center of the bright segment is computed. Step 510, as stated hereinbefore, marks the center point on the image, and step 512 sets the bright count back to zero after step 512. If the answer in step 506 is "no", then the program proceeds to step 514, where the column (COL) is incremented by 1.

Step 516 asks if the location is the end of the row If "no", the program goes through the loop again starting at step 490. If the answer to step 516 is "yes", the program sets the column to zero and increments the row by 1. The last step 520 asks if the row is the last row. If "no", the program goes back to the loop at step 490, and if "yes", the program, by return step 522, returns to the FEAT EXT subroutine 460 of FIG. 24.

An example of some of the above steps is shown in the bottom portion of FIG. 26c. The first row, Row 1, shows a series of numbers 50, 40, 45, 100, 107, 110, 106, 99, 43, 42, and 56. If the results of T(N) computed in step 486 (FIG. 25) is T=75, the T values for the selected row which are greater than T=75 are considered to be bright and are indicated by a "B". Those T values less than T=75 are considered to be dark and are indicated by a "D". The second row, Row 2, contains Bs, and Ds, and the third row, Row 3, contains black dots and an "X".

Row 1 is a sample of intensities along a row. Row 2 classifies the pixels based on T. A "B" represents a bright pixel, i.e. greater than T. A "D" represents a dark pixel, i.e. less than T. The "X" in Row 3 represents a midpoint of the run of bright (B) pixels in Row 2. The dots represent all other representations of intensities.

The latter step represents the pixel which is determined to be in the horizontal center of a white square, and is, in effect, marked with blue graphics in the frame grapper of the computer processor. The processing of the CONTRAST routine 486 produces an image with a number of blue dots denoting pixels which are located along the horizontal of the white squares. The clearest white squares will appear as having jagged blue columns passing through their center as exemplified in the output image of number 487 in FIG. 26a.

Referring again to the FEAT EXT routine reference 460 of FIG. 24, the next routine in the process is the TRACELINES routine 474. The flow chart for this routine 474 is illustrated in FIG. 27, and an illustration of the results of the steps is shown in FIG. 28.

Figure 27:
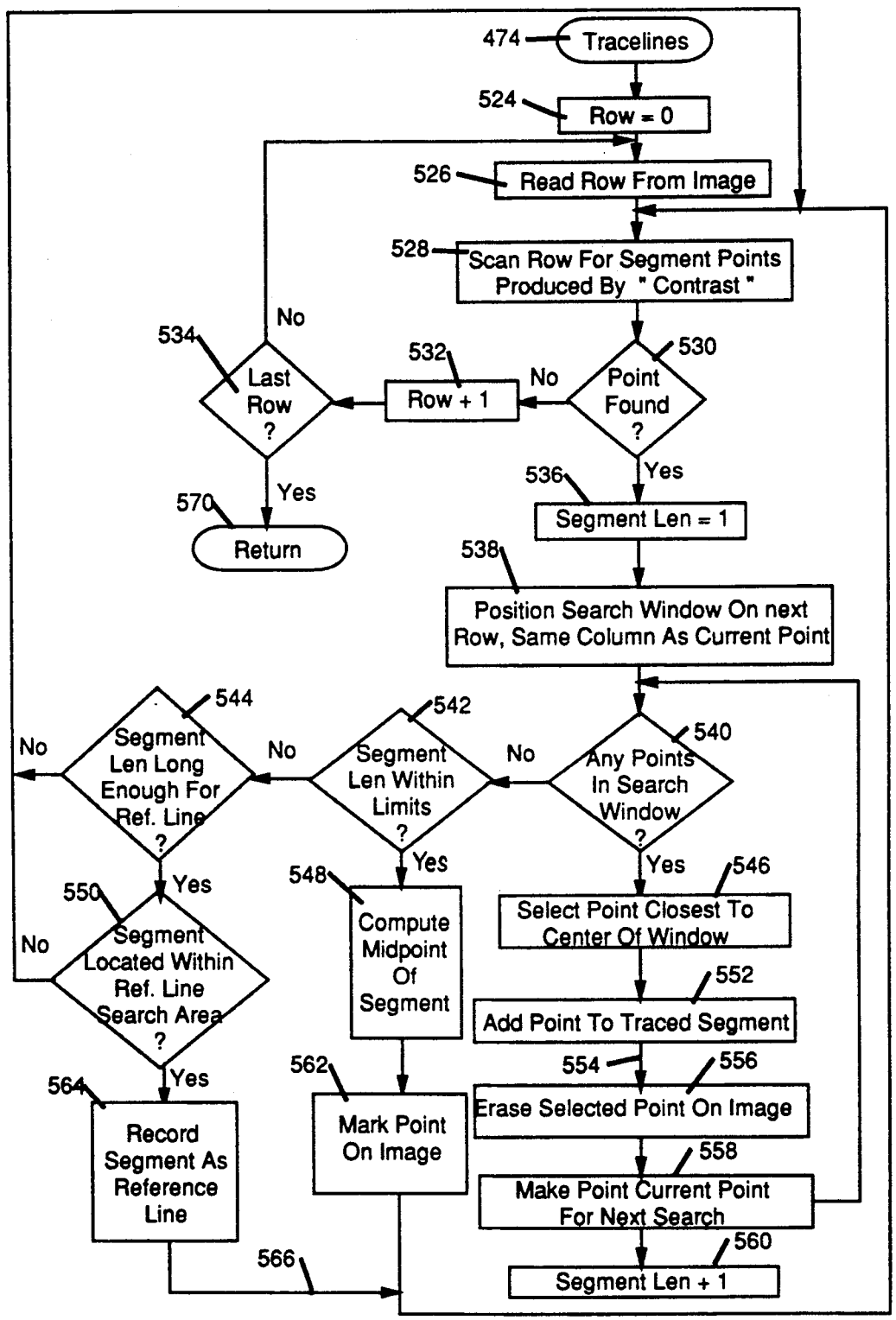
Figure 28:
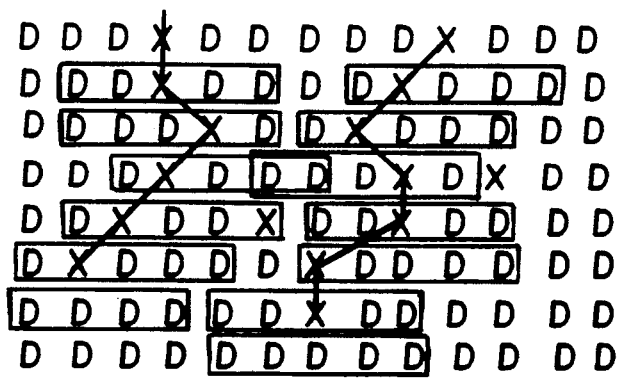

Referring particularly to FIG. 27, this routine 474 finds the center of the white squares in the image of the projected grid intersections. This is done by linking the horizontal centers of the white squares found in the CONTRAST routine 472 to form vertical columns. The several steps involved for this process are indicated at reference numbers 524–540 and 546–560. The formed vertical columns are then checked for the desired length (Len) and straightness as indicated at reference number 542 in FIG. 27. When the proper length and straightness is checked, as indicated at reference number 542, then as indicated at reference numbers 548 and 562 the midpoint of the vertical column is found and marked on the image in green, representing the center of a white square. The green dot represents the center of the white square.

This TRACELINES routine 474 also searches for the reference line when testing for the length of the formed vertical column as indicated at reference numbers 544, 550, and 564.

Finding the reference line is the first step in finding the reference point. If the vertical column is long enough to be the reference line as indicated at reference number 544 and is located within the specified reference line search area indicated at reference number 550 of the image, its location is recorded as indicated at reference number 564 and is used later in determining the location of the reference point as indicated along loop lines 566 and 568 of the flow chart of FIG. 27.

Now for a detailed description of the flow chart of FIG. 27. In step 524, row is set to zero. In step 526, the row in step 524 is read from the image. In step 528, the row is scanned for segment points produced by the contrast subroutine 472 of FIG. 25. Step 530 asks if a point has been found. If "no" the row is incremented by one in step 532 Step 534 asks if the row is the last row. If "yes" then the program by return step 570 returns to the FEAT EXT routine 460 of FIG. 24. If the answer to step 534 is "no" then the program loops back to step 526.

If the answer to step 530 is "yes", step 536 sets the segment length (SEGMENT LEN) to one. Step 538 positions the search window on the next row and in the same column as the current point being analyzed. Step 540 asks if any points are in the search window. If "no" the program proceeds to step 542 to ask the next question, which is whether the line segment being analyzed is within the limits. If the answer to step 542 is "no", then the program proceeds to step 544 and asks if the segment length is long enough to be the reference line. If "no", the program loops back to step 528. If "yes" then step 550 asks if the segment is located within the reference line search area. If "no", then the program loops back to step 528. If the answer to step 550 is "yes", then step 564 records the segment as a reference line. From step 564 along reference line 566, the program loops back to step 528.

Referring again to step 542, if the answer is "yes", step 548 computes the midpoint of the segment. Step 562 follows step 548 and marks the point on the image. This mark represents the center of a white square. From step 562, the program loops back to step 528.

Referring again to step 540, if the answer is "yes", then step 546 selects the point closest to the center of the window. Step 552 follows step 546, and adds the point to the traced segment. The next step as indicated along reference line 554 is step 556 which erases the selected point on the image. Step 558 makes the point the current point to be used for the next search. Step 560 increments the segment length (SEGMENT LEN) by one, and proceeds to do the loop or loops of this tracelines subroutine 474 starting with step 538 midway in FIG. 27.

The results of the flow chart of FIG. 27 is shown in FIG. 28 entitled "TRACELINES ALGORITHM" where the X in each row represents the point produced in the CONTRAST routine 472. The rectangle represents the area which is searched for linking the X points, and the jagged lines running in a vertical direction connect the X's in each row.

The return step 570 of FIG. 27 returns the program to the FIND REFPT routine 476 of the FEAT EXT routine of FIG. 24. This FIND REFPT routine 476 stands for "find the reference point," and performs the final step for finding the reference line of the "TRACE-LINES" algorithm of FIG. 27.

Figure 29:
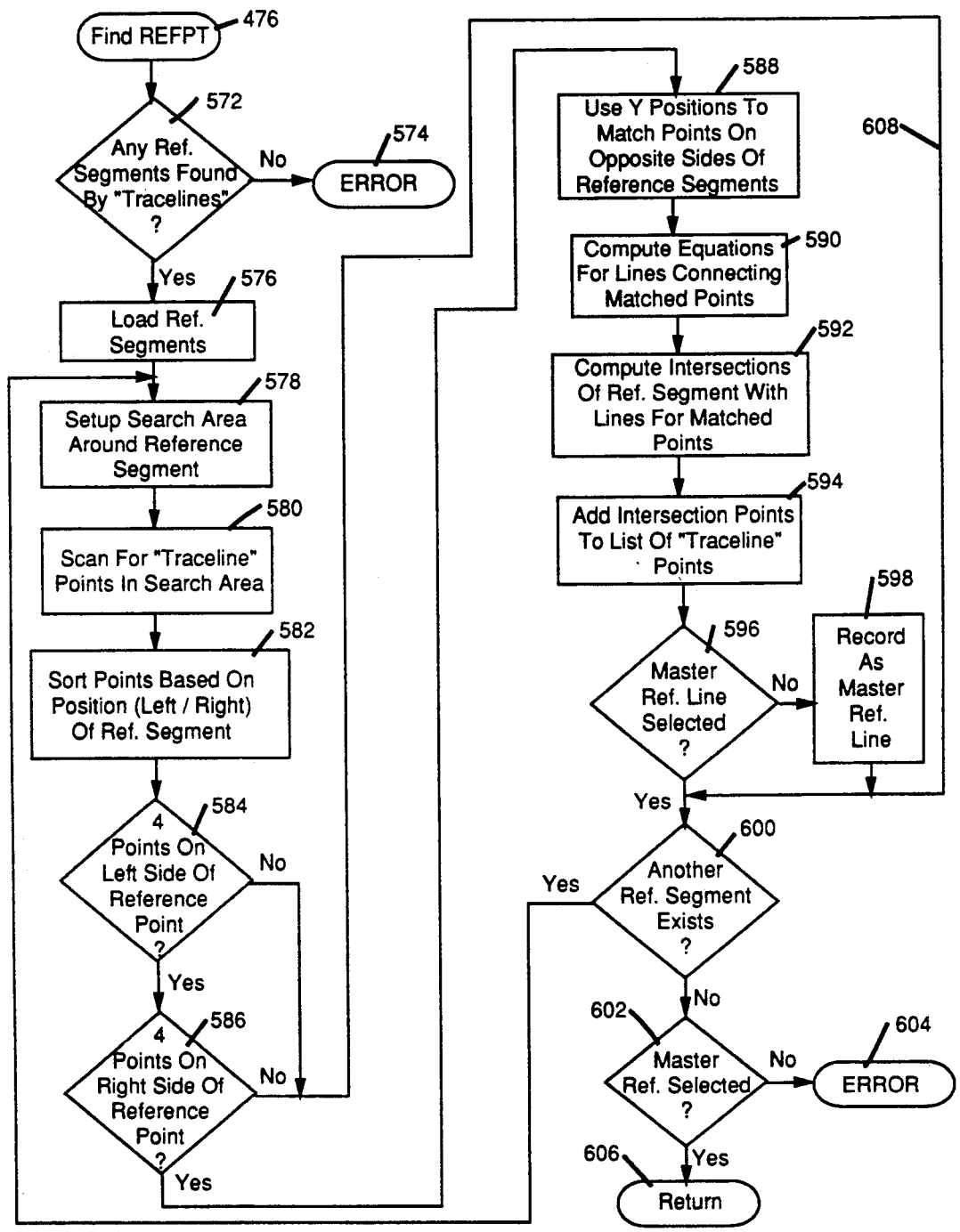
Figure 30:
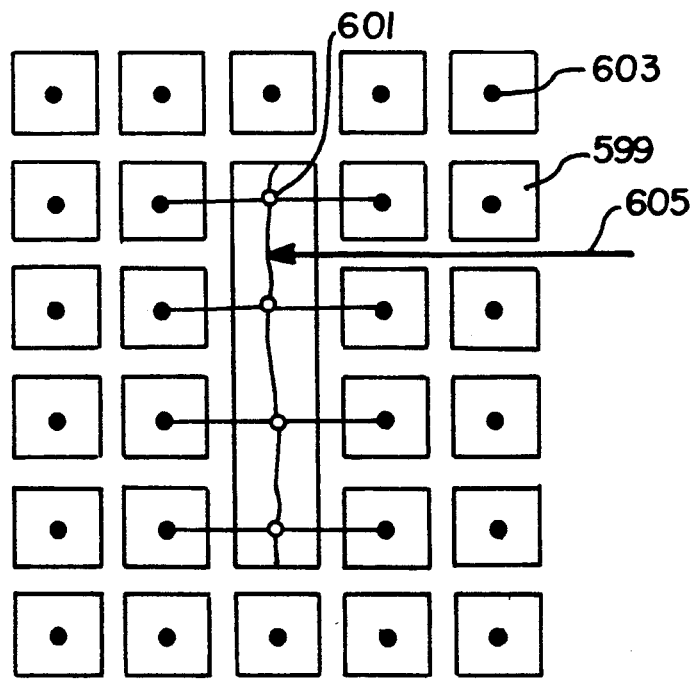

The flow chart for this routine 476 in FIG. 24 appears in FIG. 29, and a representation of this FIND REFPT routine 476 is shown in FIG. 30.

Referring particularly to FIG. 29, the first step 572 for routine 476 is to find whether any reference segments are found by the TRACELINES routine 474. If the answer is "no", then there is an error, as indicated at 574. This is reported to the operator. At this time, the image is determined to be unprocessable and the operator is instructed to capture another image. This TRACELINES routine 474 is performed again. If "yes", this routine 476 continues with reference numbers 576, 578, 580, and 582.

This FIND REFPT routine 476 in FIG. 29 checks for previously detected white square centers located near any previously detected reference lines. In order for a reference line to be successfully found, four white square centers bordering in a vertical direction must be found on each side of at least one of the two reference lines formed in the image. Finding these four points on either side of a reference line is shown at reference numbers 584 and 586. If the answer is "no" for steps 584 and 586, this routine 476 concludes that another reference segment exists as indicated at step 600 as shown along the direction line of reference number 608, and repeats the steps of reference numbers 584 and 586 until the answer is "yes".

When the required eight centers for the white squares are found, these centers representing the reference line are computed by computing the horizontal midpoint between each horizontal pair of the vertically bordering white square centers. The steps for performing this is shown at reference numbers 588, 590, 592, 596, 598, and 600 of FIG. 29, and is shown graphically in FIG. 30. The last few steps at reference numbers 602 and 604 asks the question as to whether a master reference line was found. If the answer is "no", then an error is determined to exist in the program. This error is reported to the operator and the operator is instructed to acquire another image. A master reference line is determined to be found when the reference line being examined passes all tests.

Now to explain the flow chart of FIG. 29 in more detail. As already discussed, step 572 asks if any reference segments were found by the tracelines algorithm of FIG. 27. If "yes", step 576 loads the reference segments into the program. Step 578 sets up a search area around the reference segment. Step 580 scans for the "TRACELINE" points in the search area. Step 582 sorts the points based on its position, i.e., if it is left or right of the reference segment.

Step 584 asks if there are four points on the left side of the reference point. If "yes", then step 588 uses the Y-positions to match the points on the opposite sides of the reference segment.

Step 590 computes the equations for the lines connecting the matched points. Step 592 computes the intersections of the reference segment with the lines for the matched points. Step 594 adds the intersection points to the list of "traceline" points. Step 596 asks if a master reference line has been selected. If "yes" the program goes to step 600 and asks if a reference segment exists. If "yes" the algorithm loops back to step 578.

Referring again to step 586 which is almost midway in FIG. 29, if the answer is "no", the program goes to step 600.

Referring again to step 596 near the bottom of FIG. 27, if the answer is "no", the program proceeds to step 598. The master reference line in step 596 is recorded as the master reference line. From step 598, the program goes to step 600. If the answer in step 600 is "no", then the question is asked if the master reference lne has been selected. If "no", then step 604 indicates an error.

FIG. 30 illustrates a representation of the FIND REF PT routine 476 of FIG. 29, and is entitled "FIND REF PT ALGORITHM." The blocks, one of which is indicated at 599, are the white squares. The white circles, one of which is indicated at reference number 601, are the intersection of the reference line and the line connecting the matching points on opposite sides of the reference line. The black dots, one of which is indicated at reference number 603, represent the center of the white squares as determined by the traceline algorithm of FIG. 27. The reference line found by this algorithm of FIG. 30 is indicated at reference number 605.

If the answer to step 602 in FIG. 29 is "yes", then routine 476, through return step indicated at 606, returns to the FEAT EXT routine of FIG. 24 to perform the next routine at reference number 478.

Figure 31:
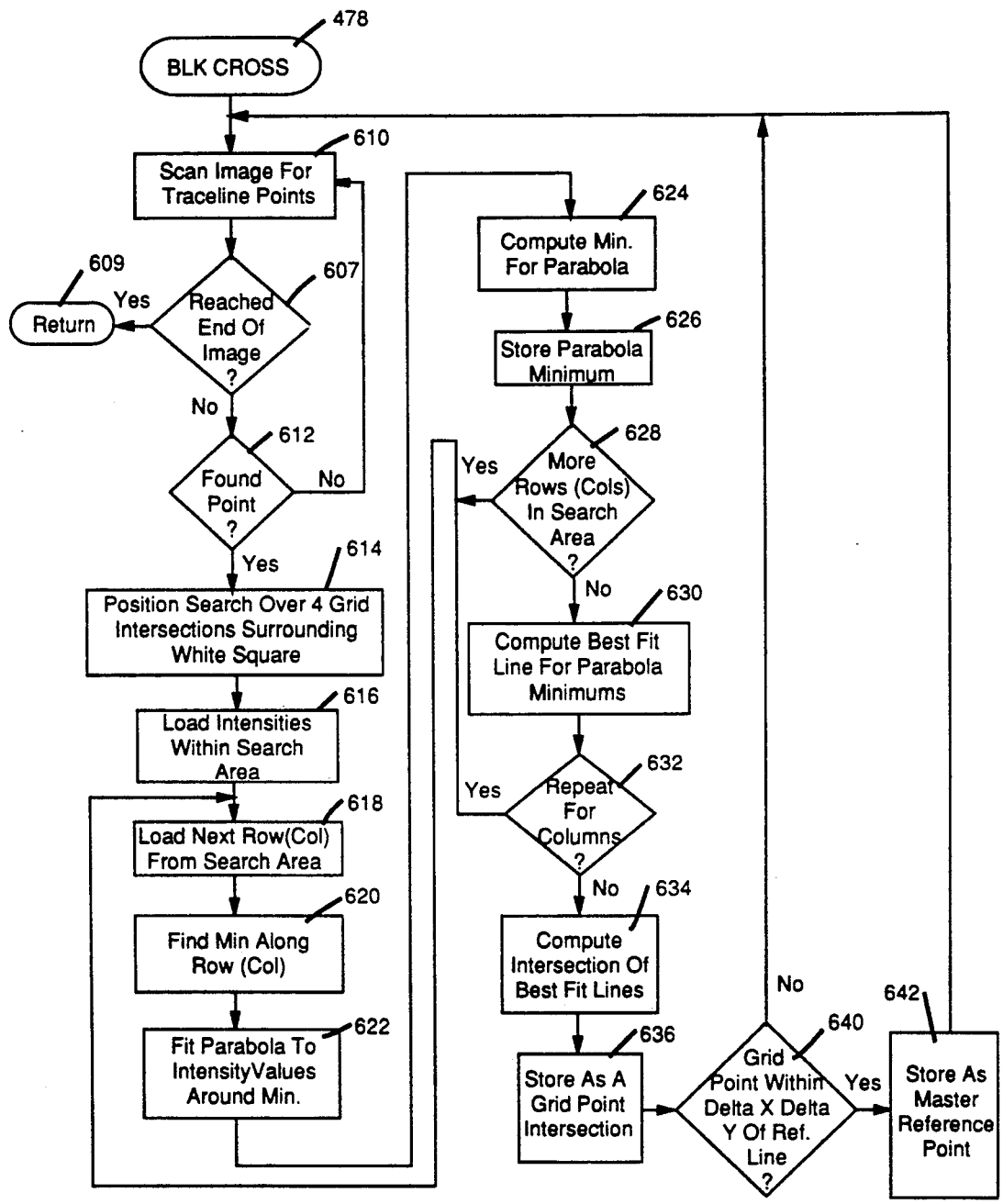

The flow chart for this BLK CROSS routine 478 of FIG. 24 is shown in FIG. 31. A graphic representation for the several steps performed by this BLK CROSS routine 478 is shown in FIGS. 32a, 32b and 32c. FIG. 32a illustrates the positioning of a search area for grid intersections. FIG. 32b and 32c illustrate the computing of a grid intersection to subpixel accuracy. FIG. 32b illustrates rows and columns of numbers which represent pixel intensities from the grid intersection search area. FIG. 32c illustrates the fitting of a parabola for subpixel accuracy. In FIG. 32c, the vertical line represents "intensity" and the horizontal axis represents intensity values ranging from $-1$ to $+1$. The parabola minimum is indicated by number 44 by arrow 633.

The BLK CROSS routine 478 of FIG. 31 determines the camera coordinates of the imaged projected grid intersections (IPGI) indicated at reference number 306 in FIG. 16. Through the various steps at reference numbers 610-642 of FIG. 31, this BLK CROSS routine 478 finds the imaged grid projection intersections (IPGI) according to subpixel accuracy. This is best shown in FIGS. 32b and 32c, and by steps at reference numbers 610, 612, and 614 of FIG. 31.

The computing process of the imaged grid intersections to subpixel accuracy is done by searching for the intensity changes for the pixels, which changes are represented by dark lines within a square search area as shown for example at reference number 611 of FIG. 32a. This square search area is positioned at each four corners as shown at reference numbers 611, 613, 615, and 617 in FIG. 32a of the center of a detected white square indicated at reference number 619 in FIG. 32a. The center of the search area for the grid intersection is located at a preset distance from the center of the white square. This center is represented by the "X" in FIG. 32a. This step or steps are particularly indicated at reference number 614 in the flow chart of FIG. 31.

This algorithm at reference number 478 of FIG. 31 searches each row of pixels within the search area 611, 613, 615, 617 of FIG. 32a for the pixel with the lowest intensity value as shown in steps 616, 618, 620 of FIG. 31. This minimum intensity for each row is represented by the black outlined blocks, one of which is indicated at reference number 619 in FIG. 32b.

Once every row is searched, the low intensity pixels are linked to form a substantial vertical line indicated at reference number 621 in FIG. 32b, which line 621 is a "best fit" line. Steps at reference numbers 622, 624, and 626 of the BLK CROSS routine 478 of the flow chart of FIG. 31 forms a parabola from the values of the minimum intensities for each row as shown in step 628 of FIG. 31. The results of this step 628 of FIG. 31 are as shown in FIG. 32c for a minimum row intensity value. An example of a minimum intensity value is shown at block reference number 623 in FIG. 32b for an intensity value of 44 shown in FIG. 32c.

The best fit line shown at 621 in FIG. 32b is computed in the step at reference number 630 of FIG. 31.

The algorithm of FIG. 31 repeats the steps at reference numbers 618, 620, 622, 624, 626, 628, and 630 to search each column of pixels within the search area 611, 613, 615, 617 (FIG. 32a) for the pixel with the lowest intensity value to form a substantial horizontal line as indicated for example at 625 in FIG. 32b, which line 625 is a "best fit" line. The minimum intensity values in each column is represented by the gray outlined blocks, one of which is indicated at reference number 627 in FIG. 32b. In this FIG. 32b, the black circle at reference number 629 represent the subpixel positions along the columns, and the black dots at reference number 631 represent the subpixel positions along the rows.

The intersection of the formed vertical and horizontal lines is found by the step at reference number 634 of FIG. 31 and is stored in the step at reference number 636 of FIG. 31 as the camera coordinate of the imaged grid intersection.

This routine 478 of FIG. 31 also checks the location of each imaged grid intersection relative to the previously found reference line found in the FIND REFPT routine 476 of FIG. 29 to see whether it is the reference point This step is shown at reference number 640 in FIG. 31. When the answer is "yes", and the reference point is found, its location is stored for future use as the master reference point as shown in step 642 in FIG. 31.

Now for a more detailed description of the flow chart of FIG. 31. Step 610 scans the image for the "traceline" points, which are the centers of the white squares. Step 607 asks if the end of image has been reached. If "yes," the routine returns to the routine of FIG. 24. If "no", the program proceeds to step 612. Step 612 asks if a point has been found. If "no", the routine goes back to Step 610. If "yes" the program continues to step 614. Using a priori knowledge, about the size of the grid of FIG. 14, the search windows are positioned over the four grid intersections surrounding the white square. Step 616 loads the intensities within the search area. Step 618 loads the next row (column) from the search area. Step 620 finds the minimum intensity along the row (column Step 622 fits the parabola to intensity values around the minimum intensity values around the minimum intensity value. Step 624 computes the minimum intensity for the parabola. Step 626 stores the minimum intensity value for the parabola. Step 628 asks if any additional rows (columns) are in the search area. If "yes", the program goes back to Step 618. If "no", the program proceeds to step 630, and computes the best fit line for the parabola minimum intensity value. Step 632 asks if steps 618-630 should be repeated for the columns. If "yes", the program goes to step 618. If "no", the program goes to step 634, and computes the intersection of the best fit lines. Step 636 stores the best fit line as a grid point intersection. Step 640 asks if the grid point is within delta x and delta y of the reference line. If "no", the program goes back to step 610. If the answer is "yes" to step 640, the program proceeds to step 642, and stores the output from step 640 as a master reference point. From step 642, the program goes back to step 610.

This BLK CROSS routine 478 returns to the FEAT EXT routine 460 of FIG. 24 to perform the next GROW routine 480

This GROW routine 480 determines the grid coordinate of each imaged grid intersection. The flow chart for this routine 480 is shown in FIG. 33. This is done by determining the proximity for each imaged grid intersection to the imaged reference point grid intersection. A technique called "region growing" is used where a search starts from the imaged reference point grid intersection for four connecting neighboring imaged grid intersections. Both an input and output grid array are formed by this technique.

Figure 33:
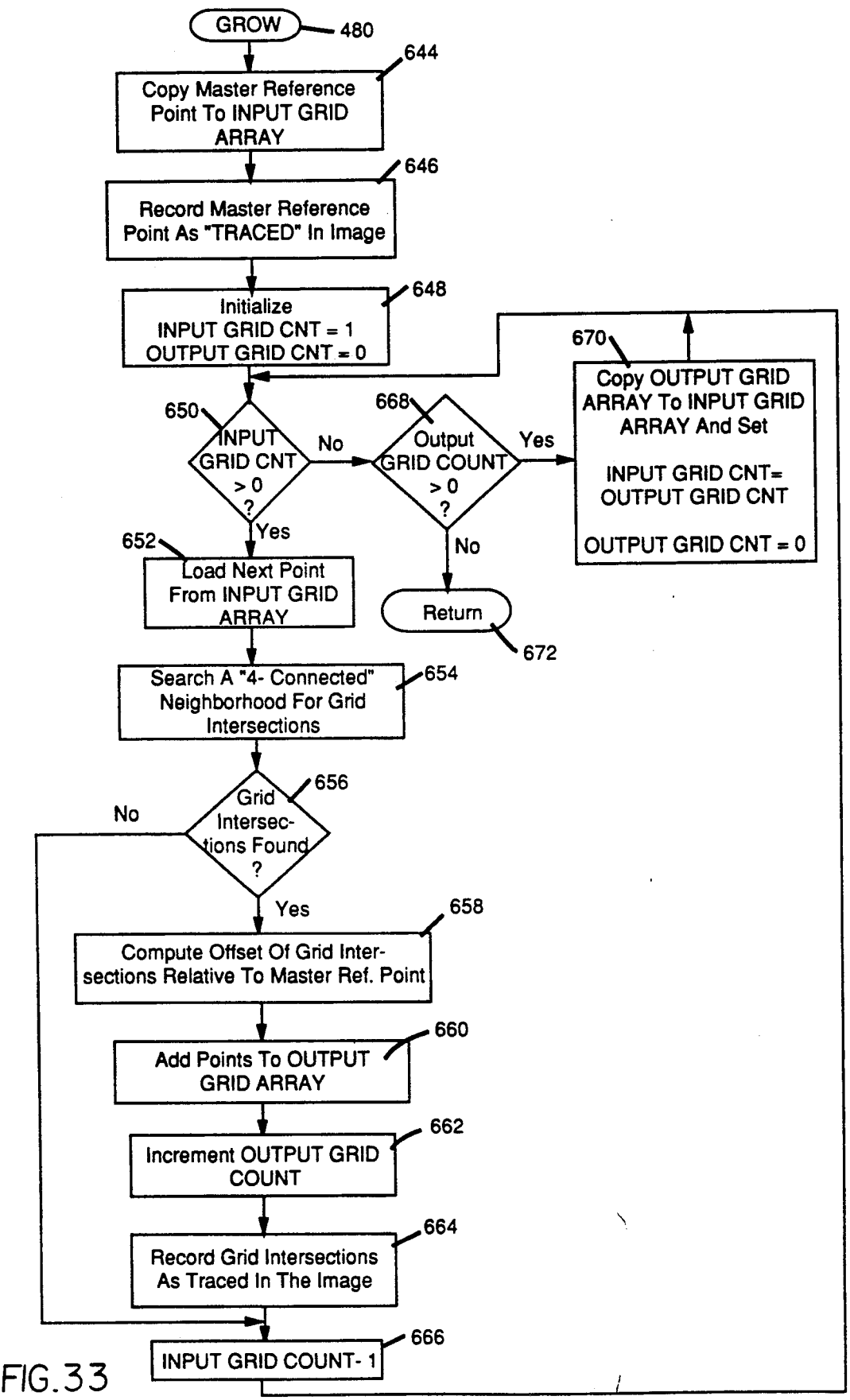

The several steps involved in this technique for forming the input and output arrays are indicated at reference numbers 644-670 in FIG. 33, which uses the master reference point indicated at reference number 644, and found in the BLK CROSS routine 478 of FIG. 31.

The final output array consists of a matrix of camera coordinates of the imaged grid intersections. The row and column indices of the matrix correspond to the grid coordinates.

When the output grid counter equals zero as indicated at reference number 668 in FIG. 33, the GROW routine 480 returns to step 672 in FIG. 33 and to the FEAT EXT routine 460 in FIG. 24, which in turn, by step 482 returns to the MEASURE routine 452 of FIG. 23.

Now to give a more detailed description of the flow chart of FIG. 33, and the GROW algorithm at reference number 480. Step 644 copies the master reference point found in the BLK CROSS routine 478 into an INPUT GRID ARRAY. Step 646 records the master reference point as TRACED in the image. Step 648 initializes the center of the input grid as one (input grid CNT=1), and the center of the output grid as zero (output grid CNT=0). Step 650 asks if the input grid center is greater than zero. If "yes" the next step is to load the next point from the INPUT GRID ARRAY as indicated by reference line 652. Step 654 makes a search for four-connected neighboring grid intersections. The next step 656 asks if a grid intersection is found. If "no" the program advances to step 666. If "yes" the next step is step 658. This step 658 computes the offset of grid intersections relative to a master reference point. Step 660 adds the points to an output grid array. Step 662 increments the output grid count. Step 664 records the grid intersections as traced in the image. Step 666 follows step 664 and subtracts one from the input grid count. From step 666, the program goes back to step 650.

If the answer to step 650 is "no", the program proceeds to step 668, and asks if the output grid count is greater than zero. If the answer to step 668 is "no", the program returns to the FEAT EXT routine 460 of FIG. 24. If the answer is "yes" to step 668, the next step is 670 where the output grid array is copied into the input grid array and the input grid center is set equal to the output grid center. The output grid center is set to zero.

Figure 34:
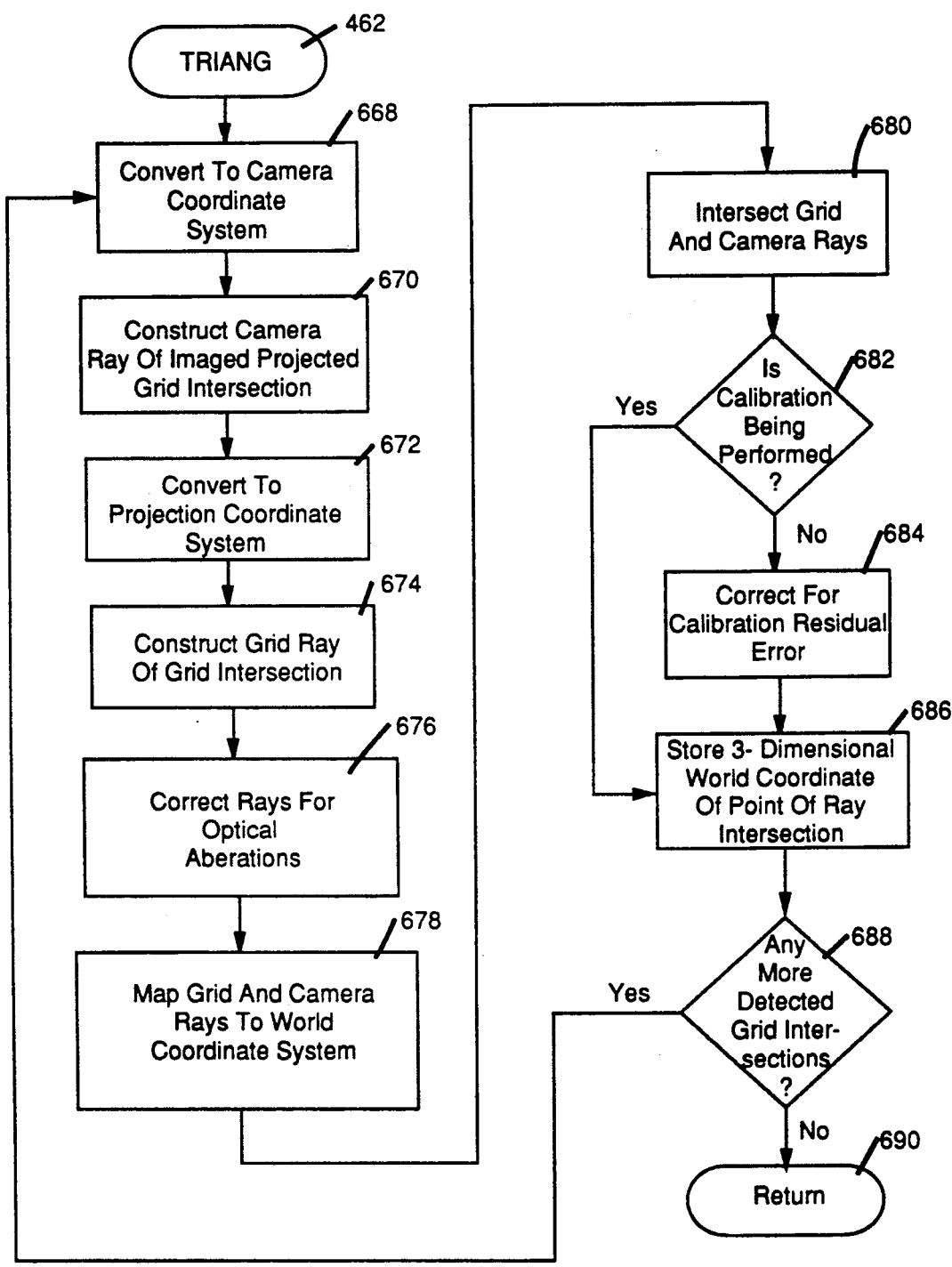

Referring now to FIGS. 23 and 34, the next routine after the FEAT EXT routine 460 is the TRIANG routine 462.

This TRIANG routine 462 of FIG. 23 computes the world coordinates of all the projected grid intersections detected in the image of the projected grid intersections in the previously FEAT EXT routine 460.

The procedure for this TRIANG routine 462 utilizes the photogrammetric stereo-triangulation technique, which is a standard procedure well-known to those skilled in the art of stereophotogrammetry. The input data consists of the camera coordinates of the imaged projected grid intersections found in the FEAT EXT routine 460 of FIG. 24, the grid coordinates of the grid intersections used to produce the projected grid intersections of the GET IMAGE routine 458 of FIG. 23, and the calibration information found in the CALIBRATE routine 312 of FIG. 18.

The output of this CALIBRATE routine 462 of FIG. 34 consists of a two dimensional matrix of the three dimensional world coordinate values. The two dimensions of the matrix correspond to the two dimensions of the projected grid. Each world coordinate value represents the coordinate position of the projected grid intersection on the surface of the cornea being examined.

The flow chart for the TRIANG routine 462 in the measure program is shown in FIG. 34. A triangulation procedure is used to compute the world coordinates of all the projected grid intersections detected in the image of the projected grid intersections.

The input data consists of camera coordinates of the image projected grid intersections (IPGI), the grid coordinates of the grid intersections used to produce the projected grid intersections (PGI), and the calibration information. The output consists of a two-dimensional matrix of the three dimensional world coordinate values. The two dimensions of the matrix correspond to the x-y dimensions of the projection grid. Each world coordinate value represents the coordinate position of the projected grid intersection on the surface of the cornea.

In referring to FIG. 34, the first step indicated at reference number 668 converts the pixel coordinate of the imaged projected grid intersection to the camera coordinates. The pixel coordinate is first multiplied by the millimeter/pixel scale factors. The x-dimension scale factor equals the horizontal CCD dimension (FIG. 16) divided by the number of horizontal CCD elements (charged-coupled device).

The y-dimension scale factor equals the vertical CCD dimension divided by the number of vertical frame buffer pixels.

In view of the difference between the video scanning rates for the CCD and the frame grabber, the x-dimension scale factor is also multiplied by the ratio of the CCD horizontal scan frequency to the frame grabber horizontal scan frequency. These scan frequencies are obtained by using a conventional frequency counter connected to the clocks of the CCD and frame grabber.

After the x-y pixel dimensions are converted to millimeter coordinates by their respective scale factors, they are converted to the camera coordinates by subtraction of the camera principal point coordinates (Ccx, Ccy).

This procedure was explained hereinbefore at step 392 in FIG. 20.

The next step at step 670 of FIG. 34 constructs a camera ray of imaged projected grid intersection (IPGI).

This procedure at reference number 670 converts the camera coordinates of an imaged projected grid intersection into a three-dimensional vector or ray. This ray emanates from the camera location determined during calibration, and passes through the imaged projected grid intersection. The ray is computed by adding the calibrated camera focal length as the Z-coordinate to the camera coordinates of the imaged projected grid intersection to form a three-dimensional ray. This three-dimensional value denotes the direction of the ray which forms the image of the projected grid intersection when the ray intersects the camera CCD plane. This ray is represented in a coordinate system whose origin is defined by the camera location.

The next step at reference number 672 of FIG. 34 converts the grid coordinates of the grid intersections corresponding to the detected imaged projected grid intersections to the projection coordinate system.

The x and y grid coordinates are first multiplied by the millimeter/grid scale factor determined by the design of the grid pattern (FIG. 14). The millimeter coordinate is then converted to the projection coordinate system by subtracting the principal point coordinate of the projection grid (Cpx, Cpy) therefrom.

The next step of this subroutine is defined by the step at reference number 674 of FIG. 34. This procedure converts a grid coordinate of a grid intersection to a three-dimensional vector or ray. This ray forms the projected grid intersection on the surface of the cornea. This ray is constructed similarly to that for the camera ray except that the input consists of the grid coordinate of the grid intersection and the focal length (Fp) of the projection system.

The next procedure at step 676 is to correct the rays for optical aberrations for the slit-lamp, the operating microscope 10, and/or the optical system 12 of the device of FIG. 3. The correction information is determined during calibration and is applied to the x and y components of the distortion coefficients of the camera and projection rays, Kc1, Kc2, Kc3, Pc1, Pc2, Kp1, Kp2, Kp3, Pp1, Pp2. As mentioned hereinabove, these distortion coefficients are not shown in FIG. 16, but are represented in the software.

The step at reference number 678 of FIG. 34 maps the grid and camera rays to the world coordinate system, defined during the calibration procedure. This is done by multiplying the grid ray by the inverse of the projection rotation matrix and the camera ray by the inverse of the camera rotation matrix. These matrices are constructed from the rotation angles of the locations of camera and projection system which were determined during the calibration procedure of FIG. 18. The conversion of these rotational angles of the location of the camera and projection system to a rotation matrix is a standard photogrammetric procedure outlined in several photogrammetry publications.

The next procedure for this subroutine of FIG. 34 is indicated at reference number 680. This step performs the actual elevation computation. This is done by determining the point of intersection of the camera rays with the grid rays. This procedure is also a standard photogrammetric procedure outlined in several publications. The output consists of a three-dimensional point in world coordinates which represents the position of the projected grid intersection (PGI).

The next step is indicated at reference number 682, and asks whether a calibration is being performed. If a calibration is not being performed, the subroutine proceeds to the procedure indicated at reference number 684 to correct for the calibration residual error, which may remain after the Bundle Model Adjustment technique of step 318 of FIG. 21. This is performed by solving a polynomial equation for each of the three dimensions of the calculated projected grid intersection (PGI) world coordinates. The polynomial is the same thirty-six term third order polynomial discussed hereinbefore. The inputs for each of the three equations consist of the three dimensions of the calculated PGI world coordinate and the coefficients of the calibrated polynomial for that dimension. The output is a correction for that dimension of the PGI world coordinate.

If a calibration is being performed in the step of reference number 682, then routine 462 proceeds to step 686. The residual error correction of step 684 is not performed if calibration is being done since the TRIANG routine 430 in the routine 320 of FIG. 22 has been called to produce the residual error that is used to compute the correction.

The procedure of step 686 stores the calculated and corrected three-dimensional values of the world coordinates of the projected grid intersection (PGI) into a two dimensional array. The array indices are the same as the grid coordinates of the projection grid (PGI).

The next step at reference number 688 of FIG. 34 asks whether any more grid intersections are detected. If "yes", the routine goes back to the step of reference number 668. If "no", the routine, by return step 690 returns to MEASURE routine 452 of FIG. 23 to perform the next step at reference number 464 entitled SQ MATRIX.

This TRIANG routine 462 of FIG. 34 is similar to the TRIANG routine 430 at FIG. 23. The routine 462 acts differently for both callers as indicated at 682 in FIG. 34.

The next routine following TRIANG 462 in FIG. 23 is entitled "SQ MATRIX" and is indicated at reference number 464. A flow chart for a "MAKESQ" (make square) algorithm for this SQ MATRIX routine 464 is shown in FIG. 35, and the results are represented in FIGS. 36a and 36b.

Figure 36A:
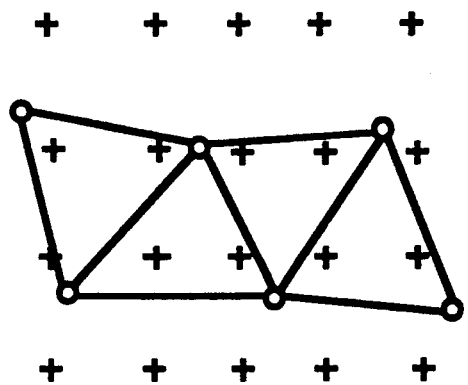

FIG. 36a represents a division of the input grid into triangles. The circles represent irregularly spaced input grid. The plus signs represent evenly spaced output grid.

Figure 36B:
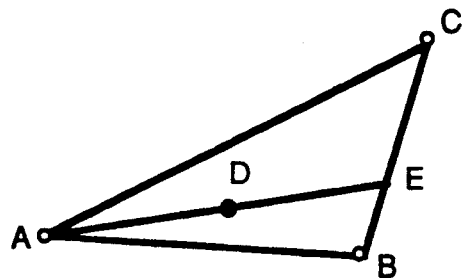

FIG. 36b represents the determination of whether a point is inside a triangle. Points A, B, and C form a triangle of irregularly spaced input points. Point "D" is a plus sign and represents a point on an evenly spaced output grid. Point "E" represents the intersection of line A-D with line B-C. The bottom of FIG. 36a sets forth two conditions for "D" being in the triangle formed by points A, B, and C, more about which is discussed hereinafter.

Figure 35:
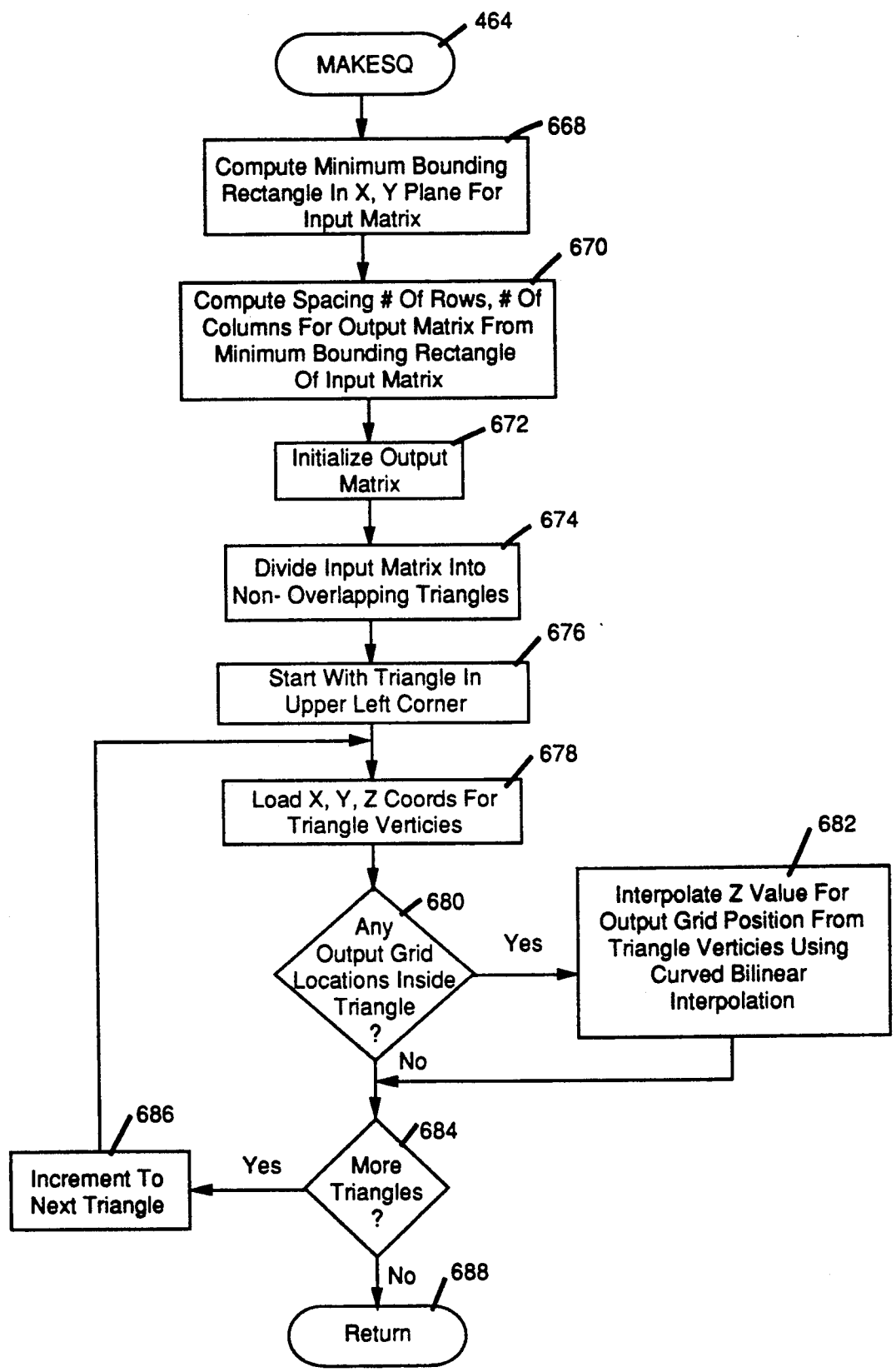

This SQ MATRIX routine 464 in FIG. 35 produces a two dimensional matrix of one dimensional elevation points which are the Z-coordinate values which are uniformly spaced in the X and Y dimensions. The input for SQ MATRIX routine 464 is a two-dimensional matrix of three dimensional world coordinate values. The three-dimensional world coordinate values will have a varying X and Y distance between neighboring points, and the routine will interpolate elevation values at evenly spaced X and Y intervals.

Referring to the flow chart in FIG. 35, the first step of reference number 668 is to compute the minimum bounding rectangle in the x-y plane for the input matrix found in the TRIANG routine 462 of FIGS. 23 and 34 performed immediately prior to this SQ MATRIX routine 464. The next step of reference number 670 in FIG. 35 is to compute the spacing, the number of rows, and the number of columns for the output matrix from the minimum bounding rectangle of the input matrix.

The step of reference number 670 proceeds to step 672 which initializes the output matrix. Step 674 divides the input matrix into non-overlapping triangles. Step 676 starts with the triangle in the upper left corner. A representation for this function is shown in FIG. 36a where the plus signs represents evenly spaced output grid values and the zeros represent the irregularly spaced input grid values.

Steps at reference numbers 678, 680, 682, 684 and 686 form a loop within a larger loop. Step 678 loads the x, y, and z coordinates for the triangle verticles. Step 680 asks if any output grid locations are inside the triangle. If "yes", then step 682 interpolates the Z-value for the output grid position from the triangle verticles using curved bilinear interpolation. If "no", step 684 asks if more triangles exist. If "yes", the program goes back through the larger loop to step 678. If "no", then this routine is returned to the next routine of FIG. 23. Steps 678-686 involve the determination of whether a point, for instance, point "D" represented in FIG. 36b by a plus on an evenly spaced output grid is within the triangle formed by the irregularly spaced input points. As mentioned hereinbefore, two conditions are necessary to determine whether point "D" is inside the triangle formed by ABC. These two conditions are: 1) if point D is between points A and E along the AE line and 2) if point E is between points B and C along the BC line.

The final output for this MAKESQ routine 464 consists of the interpolated elevation values (step at reference number 682 in FIG. 35); the x-y coordinate values of the first point in the input matrix; and the computed x-y spacings. This MAKESQ subroutine 464 of FIG. 35, as indicated at reference number 688 returns to the MEASURE routine in FIG. 23.

The output from MAKESQ routine 464 is used to perform the steps indicated at reference numbers 466 and 468 in the MEASURE routine 452 in FIG. 23.

A subroutine at reference number 466 entitled COMP CURV of FIG. 23 computes the curvature across the meridians of cornea by fitting curves to the elevation data of the previous routine 464. A number of meridians are formed by the intersections of the horizontal and vertical lines of the grid in FIG. 14 projected onto the cornea 16 (FIG. 3).

This routine 466 of FIG. 23 computes the average curvature of a cross sectional profile of the computed topography of the cornea.

This is done by computing the equation of a circle which best fits the cross sectional elevational data. The mathematical algorithm used for this step may preferably be a standard least squares approach outlined in many publications relating to corneal topography. The cross section areas or meridians may be chosen with varying lengths, angular rotations, and/or, transverse locations obtained from the corneal topography data.

The final step in the MEASURE routine 452 is the DISP RES routine 468 of FIG. 23, which displays the results on the graphic monitor of the system of FIG. 3.

The results could be stored for later analysis. This data could be stored on any computer storage medium including hard disk, floppy disk, optical disk, or magnetic tape.

These results are obtained, of course, from the measurements made in the above-discussed steps of the cornea under examination. The elevation data may be displayed by a color coded topographical map, and the meridian curvatures are, preferably, displayed in tabular form. These curvature values may preferably be displayed in units of millimeters of curvatures or is diopted units of refractive power. The discrepancy between the computed curve and the actual topographical profile data used to compute the curve preferably can be displayed graphically.

Astigmatism values preferably can be computed and displayed by computing the difference in the curvature value for at least two selected meridians, which are separated by at least 90 degrees. The two axis of astigmatism preferably can be displayed by determining the rotational angles of the two meridians with the largest difference in the curvature value.

The MEASURE routine 452 of FIG. 23 is returned to the main program (not shown) by the return step indicated at reference number 470 in FIG. 23.

Some important aspects of the computer system of the invention are as follows. The angle of separation between the projection system and the camera system is determined by the optics of the slit-lamp or the operating microscope of the system of FIG. 3. The accuracy with which this system can detect surface features is directly related to the magnitude of this angle. For this second embodiment, this angle for accuracy is preferably approximately 30 degrees. The slit-lamp, however, has an angular separation of approximately 13.8 degrees.

If the system of FIG. 3 were designed around a set of specialized optics so that the angle of separation can be increased, then the accuracy of the system can also be increased.

The calibration procedure does not depend on the optical system 12 of FIG. 3 of the invention, and therefore, the system of FIG. 3 can be used with an optical configuration requiring no particular setup.

Another approach for increasing the accuracy of the system of FIG. 3 by increasing the angle of separation of the slit-lamp or operating microscope is to attach an appropriate objective lens to the front objective of the microscope of FIG. 3. As may be understood to those in the art, the focal length of the objective lens, in part, determines the angle of separation. The longer the focal length of the objective loss, the smaller the angle. Decreasing the focal length of the objective lens results in an increase in the angle of separation. This, however, requires the patient to be positioned closer to the instrument in order to capture the image, which situation may not be allowable in a surgical environment.

This second embodiment of the invention is preferably used on patients with slight abnormalities of the cornea. If the patient has severe abnormalities, such as scarring immediately following surgery, a slightly different procedure would be used. This different procedure would involve a different projection pattern than used in the procedure with slight cornea abnormalities. The projection pattern in this instance would be the inverse or photographic negative of the original projection pattern discussed for slight cornea abnormalities. The result would be a projected grid pattern consisting of light lines and dark squares instead of dark lines and light squares. The software would essentially be the same as discussed hereinabove for slight cornea abnormalities, with only slight modifications. These modifications would not effect the flow of control exhibited in the flow charts.

The display results for this second embodiment are similar to those shown in FIGS. 11-13 for the first embodiment, including the results of FIG. 10.

It has been found that occasionally the fluorescein stain disperses too rapidly, making it somewhat impossible to produce an image on the cornea. To overcome this problem, it has been found that when fluorescein is mixed with a solution of methylcellulose and artificial tears that this mixture persists long enough for the system of the invention to produce and to obtain an image of the corneal surface.

In following the teachings of the invention, particularly the first embodiment, quantitative measurements of curvature appear to be accurate to within about 0.10 millimeters over a wide range of curvatures for about 4.6 to 8.0 millimeters. However, the deviation is greatest at both extremes of this range. For an average sized eye, with a radius of curvature of about 7.0 millimeters, it has been found by use of the invention that the accuracy is about 0.04 millimeter which is equivalent to approximately 0.3 diopters.

Preferably, the invention utilizes the optics of a Zeiss microscope with a slit lamp (FIG. 3) for projection of the grid and for the acquisition of the projected image. The video camera 32 and the projection system 34 mounted on elbows 28, 30 are used with a beam splitter 20, 22.

From the elevational information obtained by the software of the invention, curvature information of the cornea is obtained. It is to be appreciated to those skilled in the art that from the elevational information, the diopter power of the cornea can also be obtained.

The components of the invention including elbows 28, 30 adapt easily to a Zeiss or Topcon microscope. This adaptation enhances its use in an operating room in that images on the cornea are easily and quickly attainable intraoperatively without cumbersome attachments.

Also, in the invention particularly the first embodiment, the obtained data for the corneal surface is quickly processed and the results are instantly available. For instance, the projection system operates in approximately 1/1000th of a second, and the recording system operates in approximately 1/30 of a second. In an operating room, the entire process for producing an image and obtaining the results of an image may be accomplished within about one to three minutes by the invention, whereas present techniques for obtaining the topography of a cornea may take as much as twenty to thirty minutes.

It will be appreciated, therefore, that the present invention provides an effective, quick, and efficient means and method for more accurately determining the topography of a cornea of a patient in either an operating room, in an examination room or in a clinic by using rasterstereographical principles combined with an image processing unit which automatically digitizes the gridlines of a projected image through computer software. This is accomplished by causing a grid to be actually projected onto the cornea instead of the grid being reflected off the cornea which is a transparent nondiffusing member.

The system, the method, and the apparatus of the invention may be employed to derive information of the cornea of any species of the animal kingdom. Furthermore, the present invention may be used to more accurately determine the topography of any object which is transparent, nondiffusing, such as a cornea, or which is not transparent and diffusing, such as external body portions, and in some instances mandible portion where dentistry surgery is concerned. In the latter instance, it is not necessary to use the filters 38, 40, and 42, nor the fluorescein solution.

Whereas particular embodiments of the invention has been described above for purposes of illustration, it will be evident to those skilled in the art that numerous variations of the details may be made without departing from the invention as defined in the appended claims.

We claim:

1. A computerized method for determining the topography of the cornea of an eye being examined through a system performing a rasterstereography technique comprising
    determining the intrinsic and extrinsic parameters of a camera system and a projection system including the position of a projection grid relative to the projection system through a calibration procedure,
    projecting a projection grid pattern of said grid having intersecting substantially vertical and horizontal lines onto the cornea with the projection system,
    coating the surface of the cornea with a topical solution resulting in the eye having a substantially non transparent, light diffusing surface for creating an overlaying grid pattern on the cornea,
    obtaining an image of the projected grid pattern which overlays the surface of the cornea by a video camera system,
    determining the location of grid intersection (GI) point of the projection grid and the location of an imaged projection grid intersection (IPGI) point in the image, mathematically constructing a first light ray from the data obtained for the determination of the location of said grid intersection (GI) point, and a second light ray from the data obtained for the determination of the location of the imaged projection grid intersection (IPGI) point,
    determining the location of a projected grid intersection (PGI) point on the surface of the cornea by intersecting said first light ray for said grid intersection (GI) point with said second light ray for said imaged projection grid intersection (IPGI) point, and
    from the data obtained in determining the position of the projected grid intersection (PGI) point, determining the topography of the cornea.

2. The computerized method of claim 1, including representing two dimensions from the intersections of the vertical and horizontal lines of the grid pattern, and
    extracting surface measurements of the cornea from this two-dimensional representation through image processing techniques.

3. The computerized method of claim 2, including in the step of determining the location of the imaged projection grid intersection IPGI point, performing this operation for several IPGI points, and
    detecting a substantial number of IPGI points and calculating their location relative to a known reference grid intersection (GI) point by determining their proximity relative to the image of a known reference grid intersection.

4. The computerized method of claim 3, including designating the location of the IPGI point in terms of pixel in the computer frame buffer.

5. The computerized method of claim 4, including designating the location of the GI points in terms of rows and columns.

6. The computerized method of claim 5, including converting the coordinates of the IPGI point and the GI point into millimeters units.

7. The computerized method of claim 6, including converting the millimeter units of the IPGI points into coordinates for a coordinate system of the camera system.

8. The computerized method of claim 7, including converting the millimeter units of the GI points into coordinates for a coordinate system of the projection system.

9. The computerized method of claim 8, including using the coordinates of each of the GI points in the coordinate system of the projection system and the coordinates of each of the respective IPGI points in the coordinate system of the camera system to compute actual coordinates for their respective projected grid intersection (PGI) point for a coordinate system of a world system.

10. The computerized method of claim 9, including providing said coordinate system for said camera system with x, y, z dimensional axes defined by the location and orientation of the camera system.

11. The computerized method of claim 10, including providing said coordinate system for said projection system with x, y, z dimensional axes defined by the location and orientation of the projection system including the projection grid.

12. The computerized method of claim 11, including during said calibration procedure establishing reference world coordinate system for interpolating said actual coordinates for said each projected grid intersection (PGI) point.

13. The computerized method of claim 12, including in said establishing of said reference world system, using a calibration plate defining an x, y, z dimensional axes based on the position of the calibration plate.

14. The computerized method of claim 13, including in said calibration procedure,
    obtaining data representative of calibration control points of the system based on said calibration plate,
    performing a rough approximation of the system by a radial alignment constraint method using a subset of said calibration control points
    performing a fine calibration of the system by a bundle model adjustment method using a complete set of said calibration control points, and
    performing a final calibration of the system by a space correction procedure to correct for residual errors in the system.

15. The computerized method of claim 14, including in said final calibration of the system, using a general second order polynomial equation of three variable with the addition of nine third order terms, and
    solving said second order polynomial equation for each dimension of said reference world coordinate system.

16. The computerized method of claim 1, including in the step of determining the intrinsic parameters of the camera system, defining the intrinsic parameters to include the principal point of the camera system; the effective focal length of the camera system; the camera lens radial distortion coefficient; and the camera lens tangential distortion coefficients.

17. The computerized method of claim 1, including in the step of determining the intrinsic parameters of the projection system, defining the intrinsic parameters to include the principal point of the projection system; the effective focal length of the projection system; the projection lens radial distortion coefficients; and the projection tangential distortion coefficients.

18. The computerized method of claim 1, including defining the extrinsic parameters to include the position and orientation of the projection system and camera system relative to a world system, and including in the steps of determining the extrinsic parameters of the camera system, defining the extrinsic parameters to include the perspective center and the orientation angles of the camera system.

19. The computerized method of claim 1, including defining the extrinsic parameters to include the position and orientation of the projection system and the camera system relative to a world system, and including in said step of determining the extrinsic parameters of the projection system, defining the extrinsic parameters to include the perspective center and the orientation angles of the projection system.

20. The computerized method of claim 1, including in the step of determining the location of said projected grid intersection (PGI) point performing said operation for a plurality of said PGI points and using a triangulation procedure for said determination.

21. The computerized method of claim 20, including after the step of determining the location of a plurality of projected grid intersection (PGI) points by using the triangulation procedure, correcting any residual error by a "space correction" procedure.

22. The computerized method of claim 1, including obtaining a set of data points which are distributed in an irregular format with areas of varying density across the surface of the cornea, and selectively converting the irregular format of said set of surface data points into a regular format representation of surface data points by using a plurality of evenly spaced set of data which accurately represents the surface of the cornea.

23. The computerized method of claim 22, including in the step of converting the irregular format of said set of surface data into a regular format of said surface data, interpolating a Z-coordinate value which is representation of an elevational value for said evenly spaced set of data having x and y coordinates.

24. The computerized method of claim 23, including in said interpolation step, for a relatively flat surface, using a curved bilinear interpolation scheme for the nearest four data points surrounding the point to be interpolated, for a relatively non-flat surface, fitting the data points around the point to be interpolated to an analytical function using a least squares approach, and calculating a new interpolated value by solving the fitted equation for each said evenly spaced set of data having x-y coordinates to produce an output consisting of a Z world coordinate for each said evenly spaced set of data having x-y coordinates, x and y spacing for an each Z world coordinate, and the x and y world coordinates for each Z world coordinate, whereby said Z world coordinate represents an elevation value for an elevation matrix.

25. The computerized method of claim 24, including computing the curvature of a plurality of meridians across the surface of a cornea by fitting curves to the elevation data from said elevation matrix, and displaying the results in the step curvature of a plurality of meridians in a desirable form.

26. Computerized apparatus for determining the topography of the cornea of an eye being examined through a system performing a rasterstereography technique comprising means for determining the intrinsic and extrinsic parameters of a camera system and a projection system including the position of a projection grid relative to the projection system through a calibration procedure, means for projecting a projection grid pattern of said grid having intersecting substantially vertical and horizontal lines onto the cornea with said projection system, said surface of said cornea being coated with a topical solution resulting in the eye having a substantially non-transparent, light diffusing surface for creating an overlaying said grid pattern on said cornea, means for obtaining an image of said projected grid pattern which overlays the surface of the cornea by a video camera system, means for determining the location of grid intersection (GI) point of said projection grid and the location of an imaged projection grid intersection (IPGI) point in said image, means for mathematically constructing a first light ray from the data obtained from said means for said determination of the location of said grid intersection (GI) point, and a second light ray from the data obtained from said means for said determination of the location of said the imaged projection grid intersection (IPGI) point, means for determining the location of a projected grid intersection (PGI) point on the surface of said cornea including means for intersecting said first light ray for said grid intersection (GI) point with said second light ray for said imaged projection grid intersection (IPGI) point, and means for determining the topography of said cornea from the data obtained by said means for determining the position of the projected grid intersection (PGI) point.

27. The computerized apparatus of claim 26, including means for representing two dimensions from an intersection of the vertical and horizontal lines of the grid pattern, and means for extracting surface measurements of the cornea from this two-dimensional representation through image processing techniques.

28. The computerized apparatus of claim 27, including in said means for determining the location of the imaged project grid intersection IPGI point, means for performing this operation for several IPGI points, and means for detecting a substantial number of IPGI points and calculating their location relative to a known reference grid intersection (GI) point by determining their proximity relative to the image of a known reference grid intersection.

29. The computerized apparatus of claim 28, including means for designating the location of said IPGI point in terms of pixel in a computer frame buffer.

30. The computerized apparatus of claim 29, including
means for designating the location of said GI points in terms of rows and columns.

31. The computerized apparatus of claim 30, including
means for converting the coordinates of said IPGI points and said GI point into millimeters units.

32. The computerized apparatus of claim 31, including
means for converting said millimeter units of said IPGI points into coordinates for a coordinate system of said camera system.

33. The computerized apparatus of claim 32, including
means for converting said millimeter units of said GI points into coordinates for a coordinate system of said projection system.

34. The computerized apparatus of claim 33, including
means for using the coordinates of each of said GI points in the coordinate system of said projection system and the coordinates of each of the respective IPGI points in the coordinate system of said camera system to compute actual coordinates for their respective projected grid intersection (PGI) point for a coordinate system of a world system.

35. The computerized apparatus of claim 34, including
means for providing said coordinate system for said camera system with x, y, z dimensional axes defined by the location and orientation of the camera system.

36. The computerized apparatus of claim 35, including
means for providing said coordinate system for said projection system with x, y, z dimensional axes defined by the location and orientation of the projection system including the projection grid.

37. The computerized apparatus of claim 36, including in said means for performing a calibration procedure, means for establishing a reference world coordinate system for interpolating said actual coordinates for said each projected grid intersection (PGI) point.

38. The computerized apparatus of claim 37, including in said means for establishing said reference world system,
a calibration plate defining an x, y, z dimensional axes based on the position of said calibration late.

39. The computerized apparatus of claim 38, including in said means for performing said calibration procedure,
means for obtaining data representative of calibration control points of said system based on said calibration plate,
means for performing a rough approximation of said system by a radial alignment constraint method including means for using a subset of said calibration control points,
means for performing a fine calibration of said system by a bundle model adjustment method including means for using a complete set of said calibration control points, and
means for performing a final calibration of said system by a space correction procedure to correct for residual errors in said system.

40. The computerized apparatus of claim 39, including said means for performing in said final calibration of said system, means for using a general second order polynomial equation of three variables with the addition of nine third order terms, and
means for solving said second order polynomial equation for each dimension of said reference world coordinate system.

41. The computerized apparatus of claim 26, including in said means for determining the intrinsic parameters of the camera system,
means for defining the intrinsic parameters to include the principal point of the camera system; the effective focal length of the camera system; the camera lens radial distortion coefficient; and the camera lens tangential distortion coefficients.

42. The computerized apparatus of claim 26, including in said means for determining the intrinsic parameters of the projection system,
means for defining the intrinsic parameters to include the principal point of the projection system; the effective focal length of the projection system; the projection lens radial distortion coefficients; and the projection tangential distortion coefficients.

43. The computerized apparatus of claim 26, including in said means for defining said extrinsic parameters to include means for defining the position and orientation of the projection system and camera system relative to a world system, and
including in the said means for determining the extrinsic parameters of the camera system, means for defining the extrinsic parameters to include the perspective center and the orientation angles of the camera system.

44. The computerized apparatus of claim 26, including in means for defining said extrinsic parameters means for defining the position and orientation of the projection system and the camera system relative to a world system, and
including in said means for determining the extrinsic parameters of the projection system, means for defining the extrinsic parameters to include the perspective center and the orientation angles of the projection system.

45. The computerized apparatus of claim 26, including in said means for determining the location of said projected grid intersection (PGI) point, means for performing said determination for a plurality of said PGI points and means for using a triangulation procedure for said determination.

46. The computerized apparatus to claim 45, including in said means for using said triangulation procedure, means for correcting any residual error by a "space correction" procedure.

47. The computerized apparatus of claim 26, including means for obtaining a set of data points which are distributed in an irregular format with areas of varying density across the surface of the cornea, and
means for selectively converting the irregular format of said set of surface data points into a regular format representation of surface data points by using a plurality of evenly spaced set of data which accurately represents the surface of the cornea.

48. The computerized apparatus of claim 47, including in said means for converting said irregular format of said set of surface data into said regular format of said surface data, mean for interpolating a Z-coordinate value which is representation of an elevation value for said evenly spaced set of data having x and y coordinates.

49. The computerized apparatus of claim 48, including in said means for said interpolation,
- for a relatively flat surface, means for using a curved bilinear interpolation scheme for the nearest four data points surrounding the point to be interpolated,
- for a relatively non-flat surface, means for fitting the data points around the point to be interpolated to an analytical function using a least squares approach, and
- means for calculating a new interpolated value by solving the fitted equation for each said evenly spaced set of data having x-y coordinates to produce an output consisting of a Z world coordinate for each said evenly spaced set of data having x-y coordinates, x and y spacing for an each Z world coordinate, and the x and y world coordinates for each Z world coordinate, whereby said Z world coordinate represents an elevation value for an elevation matrix.

50. The computerized apparatus of claim 49, including
- means for computing the curvature of a plurality of meridians across the surface of a cornea by fitting curves to the elevation data from said elevation matrix, and
- means for displaying the results in the step of computing the curvature of a plurality of meridians in the desirable form.

* * * * *

UNITED STATES PATENT AND TRADEMARK OFFICE
CERTIFICATE OF CORRECTION

PATENT NO. :  5,159,361

DATED :  October 27, 1992

INVENTOR(S) :  JAMES L. CAMBIER et al.

It is certified that error appears in the above-identified patent and that said Letters Patent is hereby corrected as shown below:

Column 8, line 24, a period --.-- should be inserted after "lenses".

Column 12, line 44, a period --.-- should be inserted after --cornea--.

Column 12, line 51, "en" should read --entitled--.

Column 13, line 59, a period --.-- should be inserted after "118".

Column 26, line 35, a period --.-- should be inserted after "(IPGI)".

Column 32, line 30, a period --.-- should be inserted after "blocks".

Column 33, line 17, a period --.-- should be inserted after "row".

Column 34, line 24, a period --.-- should be inserted after "532".

UNITED STATES PATENT AND TRADEMARK OFFICE
CERTIFICATE OF CORRECTION

PATENT NO. : 5,159,361
DATED : October 27, 1992
INVENTOR(S) : JAMES L. CAMBIER et al.

It is certified that error appears in the above-identified patent and that said Letters Patent are hereby corrected as shown below:

Column 37, line 41, a period --.-- should be inserted after "point".

Column 37, line 59, "(column" should be --(column).--

Column 38, line 13, a period --.-- should be inserted after "480".

Claim 12, column 46, line 38, --a-- should be inserted after "establishing".

Claim 25, column 48, line 7, --of computing the-- should be inserted after "step".

Claim 38, column 49, line 51, "late" should be --plate--.

Signed and Sealed this

Twenty-eight Day of February, 1995

Attest:

BRUCE LEHMAN

Attesting Officer     Commissioner of Patents and Trademarks